US007229962B2

(12) United States Patent
Chung et al.

(10) Patent No.: US 7,229,962 B2
(45) Date of Patent: Jun. 12, 2007

(54) TETRAVALENT ETANERCEPT

(75) Inventors: Yong-Hoon Chung, Seoul (KR);
Ji-Woong Han, Seoul (KR); Hye-Ja Lee, Seoul (KR); Eun-Yong Choi, Inchun-si (KR); Jin-Mi Kim, Seoul (KR)

(73) Assignee: Medexgen Co., Ltd., Seoul (KR)

( * ) Notice: Subject to any disclaimer, the term of this patent is extended or adjusted under 35 U.S.C. 154(b) by 587 days.

(21) Appl. No.: 10/363,427

(22) PCT Filed: Jul. 26, 2002

(86) PCT No.: PCT/KR02/01427

§ 371 (c)(1),
(2), (4) Date: Feb. 28, 2003

(87) PCT Pub. No.: WO03/010202

PCT Pub. Date: Feb. 6, 2003

(65) Prior Publication Data

US 2003/0195338 A1 Oct. 16, 2003

(30) Foreign Application Priority Data

Jul. 26, 2001 (KR) ............................... 2001-45028

(51) Int. Cl.
*C07K 14/715* (2006.01)
*A61K 38/16* (2006.01)
(52) U.S. Cl. ........................... 514/2; 530/350; 530/402
(58) Field of Classification Search ..................... None
See application file for complete search history.

(56) References Cited

U.S. PATENT DOCUMENTS

| 4,946,778 | A | | 8/1990 | Ladner et al. |
| 5,073,627 | A | * | 12/1991 | Curtis et al. ................. 530/351 |
| 5,349,053 | A | | 9/1994 | Landolfi |
| 5,428,130 | A | | 6/1995 | Capon et al. |
| 5,434,131 | A | | 7/1995 | Linsley et al. |
| 5,447,851 | A | | 9/1995 | Beutler et al. |
| 5,521,288 | A | | 5/1996 | Linsley et al. |
| 5,656,272 | A | | 8/1997 | Le et al. |
| 5,844,095 | A | | 12/1998 | Linsley et al. |
| 5,861,151 | A | | 1/1999 | Aruffo et al. |
| 5,977,318 | A | | 11/1999 | Linsley et al. |
| 6,046,310 | A | | 4/2000 | Queen et al. |
| 6,090,914 | A | | 7/2000 | Linsley et al. |
| 6,100,383 | A | | 8/2000 | Gallatin et al. |
| 6,132,992 | A | | 10/2000 | Ledbetter et al. |
| 6,165,476 | A | | 12/2000 | Strom et al. |
| 6,210,661 | B1 | | 4/2001 | Enssle et al. |
| 6,225,117 | B1 | | 5/2001 | Gately et al. |
| 6,225,448 | B1 | | 5/2001 | Tao et al. |

2001/0053539 A1 12/2001 Lauffer et al.

FOREIGN PATENT DOCUMENTS

| EP | 0464533 A1 | 1/1992 |
| EP | 0770628 | 5/1997 |
| EP | 1148065 | 10/2001 |
| EP | 1148065 A1 | 10/2001 |
| JP | 5-247094 | 9/1993 |
| JP | 6-508989 | 10/1994 |
| JP | 7-502413 | 3/1995 |
| JP | 7-504203 | 5/1996 |
| JP | 9-504030 | 4/1997 |
| WO | 92/16221 | 10/1992 |
| WO | 93/00431 | 1/1993 |
| WO | 93/13210 | 7/1993 |
| WO | 93/16184 | 8/1993 |
| WO | 94/06476 | 3/1994 |
| WO | 95/11303 | 4/1995 |
| WO | 95/34326 | 12/1995 |
| WO | 96/23067 | 8/1996 |
| WO | 96/31229 | 10/1996 |
| WO | 97/03682 | 2/1997 |
| WO | 98/31820 | 7/1998 |
| WO | WO 98/21820 | 7/1998 |
| WO | 99/02552 | 1/1999 |
| WO | 99/35260 | 7/1999 |
| WO | 01/77324 | 10/2001 |
| WO | PCT/KR02/01427 | 12/2002 |

OTHER PUBLICATIONS

Toby Cornish et al., "Globular Domains of Agrin are Functional Units That Collaborate to Induce Acetylcholine Receptor Clustering", Journal of Cell Science, vol. 112, pp. 1213-1223 (1999).
J. Exp. Med. vol. 177, No. 5 (1993) pp. 1439-1450.
J. Immunol. Methods vol. 223, No. 2 (1999) pp. 171-183.
FEBS Lett. vol. 360, No. 1 (1995) pp. 43-46.

(Continued)

*Primary Examiner*—Prema Mertz
(74) *Attorney, Agent, or Firm*—Greenblum & Bernstein, P.L.C.

(57) ABSTRACT

Disclosed are concatameric proteins comprising two soluble domains, in which the C-terminus of a soluble domain of a biologically active protein is linked to the N-terminus of an identical soluble domain or a distinct soluble domain of a biologically active protein. Also, the present invention discloses dimeric proteins formed by formation of intermolecular disulfide bonds at the hinge region of two monomeric proteins formed by linkage of a concatamer of two identical soluble extracellular regions of proteins involving immune response to an Fc fragment of an immunoglobulin molecule, their glycosylated proteins, DNA constructs encoding the monomeric proteins, recombinant expression plasmids containing the DNA construct, host cells transformed or transfected with the recombinant expression plasmids, and a method of preparing the dimeric proteins by culturing the host cells. Further, the present invention discloses pharmaceutical or diagnostic compositions comprising the dimeric protein or its glycosylated form.

3 Claims, 23 Drawing Sheets

OTHER PUBLICATIONS

English Language Machine Translation JP 5-247094.

F. Sanger et al., "DNA Sequencing with Chain-Terminating Inhibitors", Proc. Natl. Acad. Sci. USA, vol. 74, No. 12, pp. 5463-5467 (1977).

Daniel J. Capon et al., "Designing CD4 Immunoadhesins for AIDS Therapy", Nature, vol. 337, pp. 525-531 (1989).

Werner LESSLAUER et al., "Recombinant Soluble Tumor Necrosis Factor Receptor Proteins Protect Mice From Lipopolysaccharide-Induced Lethality", Eur. J. Immunol., vol. 21, pp. 2883-2886 (1991).

Avi Ashkenazi et al., "Protection Against Endotoxic Shock by a Tumor Necrosis Factor Receptor Immunoadhesin", Proc. Natl. Acad. Sci. USA, vol. 88, pp. 10535-10539 (1991).

Karsten Peppel et al., "A Tumor Necrosis Factor (TNF) Receptor-IgG Heavy Chain Chimetric Protein as a Bivalent Anatagonist of TNF Activity", J. Exp. Med., vol. 174, pp. 1483-1489 (1991).

Kendall M. Mohler et al., "Soluble Tumor Necrosis Factor (TNF) Receptors Are Effective Therapeutic Agents in Lethal Endotoxemia and Function Simultaneously as Both TNF Carriers and TNF Antagonists", The Journal of Immunology, vol. 151, pp. 1548-1561 (1993).

Bernard J. Scallon et al., "Functional Comparisons of Different Tumor Necrosis Factor Receptor/IgG Fusion Proteins", Cytokine, vol. 7, No. 8, pp. 759-770 (1995).

Katherine Harper et al., "CTLA-4 and CD28 Activated Lymphocyte Molecules are Closely Related in Both Mouse and Human as to Sequence, Message Expression, Gene Structure, and Chromosomal Location", the Journal of Immunology, vol. 147, pp. 1037-1044 (1991).

Jean-Francois Brunet et al., "A New Member of the Immunoglobulin Superfamily -CTLA-4", Nature, vol. 328, pp. 267-270 (1987).

Peter S. Linsley et al., "CTLA-4 Is a Second Receptor for the B Cell Activation Antigen B7", J. Exp. Med., vol. 174, pp. 561-569 (1991).

Akira Yamada et al., "Long-Term Acceptance of Major Histrocompatibility complex-Mismatched Cardiac Allograft Induced by a Low Dose of CTLA4lgM Plus FK506", Microbiol. Immunol., vol. 40, No. 7, pp. 513-518 (1996).

Louis A. Tartaglia et al., "Two TNF Receptors", Immunology Today, vol. 13, No. 5, pp. 151-153 (1992).

B. Beutler, "Chapter 20: Cachectin/Tumor Necrosis Factor and Lymphotoxin", Peptide Growth Factor II, Springer-Verlag, Berlin, pp. 39-70 (1990).

Michael J. Eck et al., "The Structure of Human Lymphotoxin (Tumor Necrosis Factor-$\beta$) at 1.9-Å Resolution, the Journal of Biological Chemistry", vol. 267, No. 4, pp. 2119-2122 (1992).

Craig A. Smith et al., "A Receptor for Tumor Necrosis Factor Defines an Unusual Family of Cellular and Viral Proteins", Science, vol. 248, pp. 1019-1023 (1990).

Hansruedi Loetscher et al., "Molecular Cloning and Expression of the Human 55 kd Tumor Necrosis Factor Receptor", Cell, vol. 61, pp. 351-359 (1990).

Thomas J. Schall et al., "Molecular Cloning and Expression of a Receptor for Human Tumor Necrosis Factor", Cell, vol. 61, pp. 361-370 (1990).

Sambrook et al., "Molecular Cloning", Cold Spring Harbor Laboratory Press, pp. 1.25-1.31, 1.6301.69, and 7.26-7.29, (1989).

Chamow Steven M. and Ashkenazi Avi., "Immunoadhesins: principles and applications", TIBTECH, vol. 14, pp. 52-60 (1996).

Jostock Thomas et al., "Soluble gp130 is the natural inhibitor of soluble interleukin-6 receptor transsignaling responses", Eur. J. Biochem, vol. 268, pp. 160-167 (2001).

* cited by examiner

TETRAVALENT ETANERCEPT

TECHNICAL FIELD

The present invention relates to concatameric proteins, and more specifically, concatamerized structure of biologically active protein domains where C-terminal end of extracellular soluble domain of biologically active protein is fused to N-terminal end of the same or other extracellular soluble domain of biologically active protein, and dimerization of two concatamers by coupling to hinge region of Fc fragment of immunoglobulin, and glycosylated forms of the concatameric proteins.

BACKGROUND ART

The activity of cytokine is associated with pathologic severity of inflammatory and/or immune response to various antigenic stimulations. Many antigen specific antibodies and soluble receptors which could recognize cytokines are currently in use to inhibit the function of cytokines for the therapeutic purposes (WO 93/016184, WO 96/02576, WO 96/023067, WO 1997/03682, and U.S. Pat. Nos. 5,434,131, 5,656,272, 5,977,318, 6,210,661, 6,225,117). Antibodies and soluble receptors inhibit cytokine signal transduction by disturbing interaction between cytokines and their receptors on cell surface.

Soluble receptors used as functional inhibitors of cytokine that fused to heavy chains of human immunoglobulins were disclosed by Capon et al. (Nature 337:5254, 1989), and thereafter many patents were disclosed inventions related to fusion proteins of soluble receptors and immunoglobulins (U.S. Pat. Nos. 5,521,288, 5,844,095, 6,046,310, 6,090,914, 6,100,383, 6,225,448).

Generally, fusion proteins of soluble receptors and immunoglobulins have following advantages (Capon et al., Nature 337:5254, 1989)

1. Increase in total avidity to ligand by forming bivalency via dimerization.
2. Increase in blood half-life of proteins, that is, increase in molecular stability
3. Activation of effecter cells by Fc fragment of immunoglobulin heavy chain
4. Convenience of purification by using affinity column, e.g. using protein A Most fusion proteins of receptor extracellular domain and immunoglobulin heavy chain are composed of heavy chain without CH1 domain, which result in dimers not binding to light chains. This structure is more desirable for the function of proteins and receptors involving immune response. For example, TNFR(WO92/16221, WO95/34326)-immunoglobulin fusion proteins disclosed in WO94/06476 and U.S. Pat. No. 5,447,851 have been used for the inhibition of TNF-mediated inflammation. It is well known that TNFR-immunoglobulin fusion proteins have a higher affinity than original monomeric molecules (Lesslauer et al., Eur. J. Immunol. 21:2883, 1991; Ashkenazi et al., Proc. Natl. Acad. Sci. 88:10535, 1991; Peppe et al., J. Exp. Med. 174:1483, 1991; Mohler et al., J. Immunol. 151:1548, 1993).

For the improved inhibition of TNF mediated response, one can increase efficacy by multimerizing soluble extracellular domains of TNFR, CD2, and CTLA-4. For example, when fusion proteins of TNFR's extracellular domains bound with immunoglobulin heavy chain(heavy chain fusion protein) and with light chain(light chain fusion protein) respectively are coexpressed in the same cell, one can produce fusion proteins as a tetrameric form by linking heavy chain to heavy and light chains. This tetramer showed much more increased efficacy than monomeric or dimeric forms as presented by Scallon et al. (Cytokine 7:759, 1995).

However, this method had many difficulties for commercialization such as simultaneous expression of two different fusion genes in the same cell line, remarkably lower production yields of multimeric form; and difficulty in purifying multimeric high molecular weight forms. For these reasons, immunoglobulin fusion proteins currently in use are only heavy chain fused form.

Therefore, there is considerable demand for the development of methods of producing multimeric protein therapeutics with high yield and efficient purification procedures.

DISCLOSURE OF INVENTION

The present inventors have manufactured concatameric proteins by fusing the C-terminal end of soluble domain of biologically active protein to the N-terminal end of soluble domain of the same or other biologically active protein by using DNA recombination techniques. Also, the present inventors have dimerized this concatamers by linking it to the hinge region of Fc fragment of immunoglobulin and added more glycosylations by using DNA mutagenesis techniques. And the present inventors have found that concatamerized protein dimers and their glycosylated forms show increased efficacy and stability compared to conventional monomeric fusion proteins.

Therefore, in one aspect, the present invention provides concatameric proteins where C-terminal end of soluble domain of biologically active proteins is fused to N-terminal end of soluble domain of the same or other biologically active proteins.

In another aspect, the present invention provides dimeric proteins formed by disulfide bond at hinge region of two monomeric proteins whose concatamerized part is fused to hinge region of Fc fragment of immunoglobulin.

Also in another aspect, the present invention provides DNA constructs that encode monomeric fusion proteins whose concatamerized domain is fused to hinge region of Fc fragment of immunoglobulins.

Also in another aspect, the present invention provides DNA plasmids comprising a DNA construct that encodes monomeric fusion protein whose concatamerized part is fused to hinge region of Fc fragment of immunoglobulin.

Also in another aspect, the present invention provides host cells transfected or transformed with recombinant DNA plasmids including a DNA construct that encodes monomeric fusion protein whose concatamerized part is fused to hinge region of Fc fragment of immunoglobulin.

Also in another aspect, the present invention provides a method for culturing the host cells, which were transfected or transformed with recombinant DNA plasmids including a DNA construct that encodes monomeric fusion protein whose concatamerized part is fused to hinge region of Fc fragment of immunoglobulin, under culture condition for expression of DNA constructs encoding concatameric fusion protein coupled to hinge region of Fc fragment of immunoglobulin, and manufacturing dimeric concatamers formed by disulfide bond at hinge region of two monomeric concatamers described as above including the process of purification of the proteins described as above from cell culture.

Also in another aspect, the present invention provides a method for culturing the host cells, which were transfected or transformed with recombinant DNA plasmids including a DNA construct that encodes monomeric fusion protein whose concatamerized part of immunomudulatory function is fused to hinge region of Fc fragment of immunoglobulin and is inserted with glycosylation motifs, under the best condition which is suitable for expression of DNA constructs that encode monomeric fusion protein whose concatamerized part of immune function is fused to hinge region of Fc fragment of immunoglobulin, and for manufacturing glycosylated dimers formed by disulfide bond at hinge region of two monomeric proteins described as above including the process of purification of the glycosylated proteins described as above from cell culture.

Also in another aspect, the present invention provides DNA primers for inserting glycosylation motif into the DNA constructs that encode monomeric fusion proteins whose concatamerized part is fused to hinge region of Fc fragment of immunoglobulins.

Also in another aspect, the present invention provides the glycosylated dimers formed by disulfide bond at hinge region of two monomeric proteins whose concatamerized part involving immune response is fused to hinge region of Fc fragment of immunoglobulins.

Also in another aspect, the present invention provides the pharmaceutical compositions comprising dimers formed by disulfide bond at hinge region of two monomeric proteins whose concatamerized part involving immune response is fused to hinge region of Fc fragment of immunoglobulins in a pharmaceutically effective amount and in a pharmaceutically acceptable carrier.

Also in another aspect, the present invention provides the pharmaceutical compositions comprising glycosylated dimers formed by disulfide bond at hinge region of two monomeric proteins whose concatamerized part involving immune response is fused to hinge region of Fc fragment of immunoglobulins in a pharmaceutically effective amount and in a pharmaceutically acceptable carrier.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
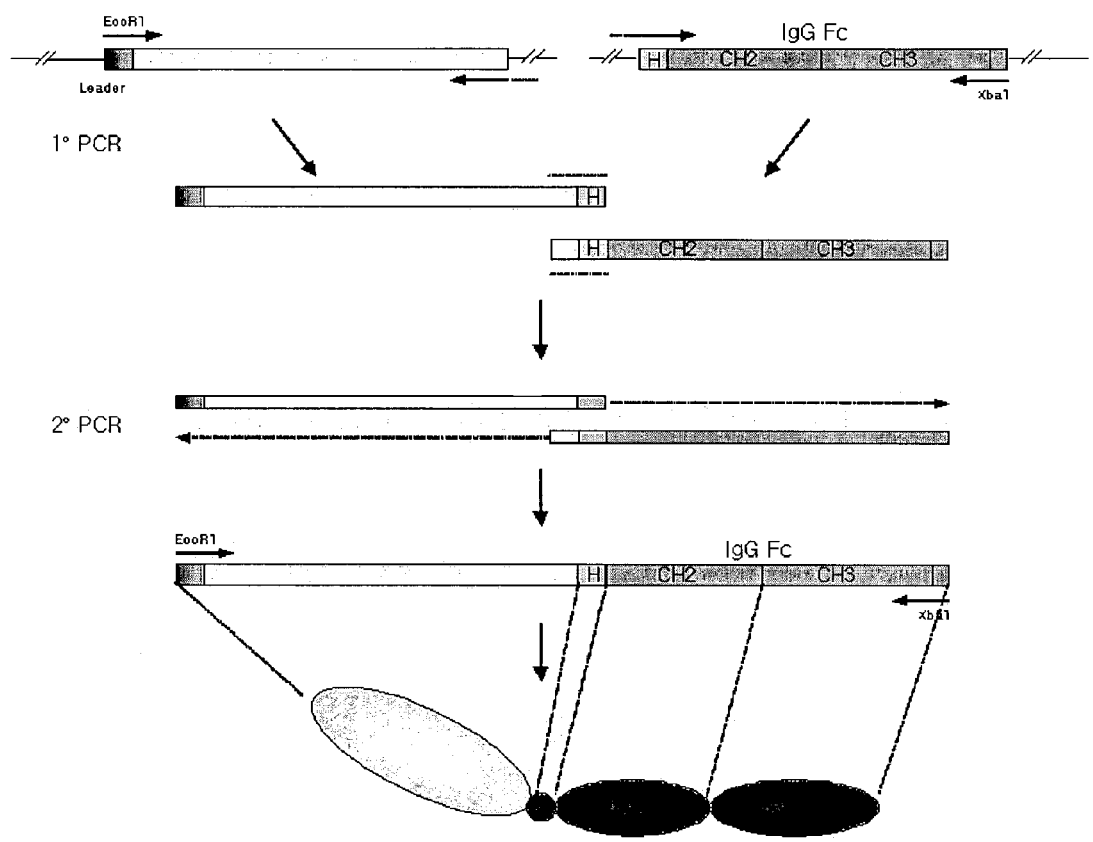
FIG. 1 is a schematic view showing a process of preparing a DNA construct encoding a conventional simple fusion monomeric protein through polymerase chain reaction (PCR)

The present invention is generally directed to concatameric proteins, and more particularly, to immunoadhesion molecules. Immunoadhesion molecules are typically formed by fusion of the Fc fragment of immunoglobulin (Ig) to a ligand-binding region of a receptor or an adhesion molecule, and thus have a structure similar to that of an antibody. The typical immunoadhesion molecules known in the art have a structure of an antibody in which the variable region is substituted with a ligand-binding region of a receptor while retaining the Fc fragment. A wide variety of immunoadhesion molecules are suggested in the literature. However, immunoadhesion molecules according to the present invention have different structure with the conventional immunoadhesion molecules, and there is also no prior art predicting or describing preparation of the immunoadhesion molecules according to the present invention.

Definition of Terms

For full understanding of the characteristic structure of the immunoadhesion molecules according to the present invention, exact definitions of the terms used in the present invention are given as follows. In general, all of the technical and scientific terms being not additionally defined in the present invention have meanings commonly used in the art. However, although having meanings commonly used in the art, the following terms are defined to give a clearer understanding of their meanings and make the scope of the present invention clear, as follows.

The term "immunoglobulin", as used herein, refers to protein molecules being produced in B cells and serving as antigen receptors specifically recognizing a wide variety of antigens. The molecules have a Y-shaped structure consisting of two identical light chains (L chains) and two identical heavy chains (H chains), in which the four chains are held together by a number of disulfide bonds, including the disulfide bridge between the H chains at the hinge region. The L and H chains comprise variable and constant regions. The L chain variable region associates with the H chain variable region, thus producing two identical antigen-binding regions. According to features of the constant regions of H chains, immunoglobulins (Ig) are classified into five isotypes, A (IgA), D (IgD), E (IgE), G (IgG) and M (IgM). Each subtype possesses unique structural and biological properties. For example, IgG has slightly different Fc structure, compared with other isotypes. In addition, IgG and IgA have a number of subtypes. For example, the human IgG isotype has four subtypes, IgG1, IgG2, IgG3 and IgG4, which have γ1, γ2, γ3 and γ4 H chains, respectively. Biological functions of immunoglobulin molecules, such as complement activation, Fc receptor-mediated phagocytosis and antigen-dependent cytotoxicity, are mediated by structural determinants (complementarity-determining regions) in the Fc region of H chains. Such an Fc region of H chains is used for construction of dimeric proteins according to the present invention, and may be derived from all isotypes and subtypes of immunoglobulin as described above.

The term "Fc fragment of an immunoglobulin molecule", as used herein, refers to a fragment having no antigen-binding activity and being easily crystallized, which comprises a hinge region and CH2 and CH3 domains, and a portion responsible for binding of an antibody to effector materials and cells. Therefore, the Fc fragment mentioned in the present invention can be different from that described in some literatures, but includes the hinge region. Such description of the Fc fragment is given to supply convenience in describing the present invention, and will be fully understood by those of ordinary skill in the art with reference to the specification of the present invention and the accompanying drawings.

The term "biologically active protein", as used herein, refers to a protein, peptide or polypeptide having generally physiological or pharmaceutical activities, which retains a part of its native activities after forming a concatamer or immunoadhesion molecule. The term "biological activity", as used herein, is not limited in meaning to physiological or pharmaceutical activities. For example, some concatamers, such as those containing an enzyme can catalyze a reaction in an organic solvent. Similarly, some high-molecular weight fusion molecules containing concanavalin A or an immunoglobulin molecule are useful as diagnostic agents in laboratories.

Non-limiting examples of the protein, peptide or polypeptide include hemoglobin, serum proteins (e.g., blood factors including factor VII, VIII and factor IX), immunoglobulin, cytokines (e.g., interleukin), α-, β- and γ-interferon, colony-stimulating agent (e.g., G-CSF and GM-CSF), platelet-derived growth factor (PDGF), and phospholipase activating proteins (PLAPs). Other typical biological or therapeutic proteins include insulin, plant proteins (e.g., lectin and ricin), tumor necrosis factor (TNF) and its related alleles, growth factors (e.g., tissue growth factors and endothelial growth factors such as TGFα or TGFβ), hormones (e.g., follicle-stimulating hormone, thyroid-stimulating hormone, antidiuretic hormone, pigment-concentrating or dispersing hormones and parathyroid hormone, luteinizing hormone-releasing hormone and its derivatives, calcitonin, calcitonin gene related peptide (CGRP), synthetic enkephalin, somatomedin, erythropoietin, hypothalamus releasing factors, prolactin, chronic gonadotrophin, tissue plasminogen-activating agents, growth hormone-releasing peptide (GHRP), and thymic humoral factor (THF). The immunoglobulins include IgG, IgE, IgM, IgA, IgD and fragments thereof. Some proteins such as interleukin, interferon or colony-stimulating factor may be produced in a non-glycosylated form using DNA recombinant techniques. The non-glycosylated proteins may be useful as biologically active materials in the present invention.

In addition, the biologically active materials useful in the present invention include any polypeptide, which has bioactivity in vivo. Examples of the biologically active materials include peptides or polypeptides, fragments of an antibody, single chain-binding proteins (see U.S. Pat. No. 4,946,778), binding molecules including fusion polypeptides of antibodies or their fragments, polyclonal antibodies, monoclonal antibodies, and catalytic antibodies. Other examples of the biologically active materials include allergen proteins, such as ragweed, antigen E, honeybee venom, or allergen of mites.

In addition, the biologically active material useful in the present invention includes enzymes. Examples of the enzymes include carbohydrate-specific enzymes, proteinases, oxidoreductases, transferases, hydrolases, lyases, isomerases, and ligases. In detail, non-limiting examples of the enzymes include asparaginase, arginase, arginine deaminase, adenosine deaminase, peroxide dismutase, endotoxinase, catalase, chymotrypsin, lipase, uricase, adenosine dephosphatase, tyrosinase, and bilirubin oxidase. Examples of the carbohydrate-specific enzymes include glucose oxidase, glucodase, galactosidase, glucocerebrosidase, and glucouronidase.

The term "proteins involving immune response", as used herein, refers to all proteins mediating cell-to-cell signal transduction during cellular or humoral immune response and thus activating or suppressing immune response. Immunity is a process of protecting "self" from "non-self" such as bacteria or viruses. Immune response is largely divided into cellular and humoral immune response, where T and B lymphocytes play the most important role. T cells, mainly mediating cellular immune response, directly attack and kill virus-infected cells or tumor cells, or help other immune cells by secreting cytokines functioning to induce or activate immune response or inflammation. B cells produce antibodies against non-self foreign materials (antigens) that enter a body, such as bacteria or viruses, and such immune response is called cellular immune response. Cell-to-cell signal transduction is an essential process in both cellular and humoral immune responses, in which a signal molecule, that is, a ligand, interacts with a cell surface receptor acting to transduce a specific signal into a cell.

Representative examples of the proteins involving the immune response according to the present invention include cytokines, cytokine receptors, adhesion molecules, tumor necrosis factor receptor (TNFR), enzymes, receptor tyrosine kinases, chemokine receptors, other cell surface proteins, and soluble ligands. Non-limiting examples of the cytokines include IL-1, IL-2, IL-3, IL-4, IL-5, IL-6, IL-7, IL-10, IL-12, IL-17, TNF, TGF, IFN, GM-CSF, G-CSF, EPO, TPO, and M-CSF. Examples of the cytokine receptors, but are not limited to, include growth hormone receptors (GHRs), IL-13R, IL-1R, IL-2R, IL-3R, IL-4R, IL-5R, IL-6R, IL-7R, IL-9R, IL-15R, TNFR, TGFR, IFNR (e.g., IFN-γ R α-chain and IFN-γ R β-chain), interferon-α R, -β R and -γ R, GM-CSFR, G-CSFR, EPOR, cMpl, gp130, and Fas (Apo 1).

Non-limiting examples of the enzymes include influenza C hemaglutinin esterase and urokinase. The chemokine receptors are exemplified by CCR1 and CXCR1-4. Examples of the receptor tyrosine kinases, but are not limited to, include TrkA, TrkB, TrkC, Htk, REK7, Rse/Tyro-3, hepatocyte growth factor R, platelet-derived growth factor R, and Flt-1. Examples of other cell surface proteins includes CD2, CD4, CD5, CD6, CD22, CD27, CD28, CD30, CD31, CD40, CD44, CD100, CD137, CD150, LAG-3, B7, B61, β-neurexin, CTLA-4, ICOS, ICAM-1, complement R-2 (CD21), IgER, lysosomal membrane gp-1, α2-microglobulin receptor-related proteins, and sodium-releasing peptide R. Non-limiting examples of the soluble ligands include IL-10, heregulin, and keratinocyte growth factors.

Ligands for the proteins involving immune response according to the present invention and use thereof are well known to those of ordinary skill in the art, as summarized in Tables 1 to 7, below.

TABLE 1

Proteins involving immune response: Adhesion molecules

| Adhesion molecules | Ligands | Uses |
|---|---|---|
| CD4 | HIV gp120 | Inhibition of in vivo HIV infection; and identification of CD4 domain participating in ligand binding |
| L-Selectin | GlyCAM-1, CD34 | Prevention of neutrophile-mediated lung damage; determination of position in tissues of a ligand by histochemical staining; and isolation and cloning of ligands and determination of their properties |
| E-Selectin | Sialyl Lewis$^X$ | Prevention of neutrophile-mediated lung damage; and determination of thermodynamic properties in ligand-binding |
| P-Selectin | Sialyl Lewis$^X$ | Prevention of neutrophile-mediated lung damage; and study of functions of individual of amino acid residues in binding to cell surface |
| ICAM-1 | CD11a/CD18 | Phagocytosis of erythrocytes in malaria; inhibition of infection with rhinovirus; and anti-inflammation in diabetes |
| ICAM-2 | CD11a/CD18 | Study of activation of T cells mediated by T cell receptor |
| ICAM-3 | CD11a/CD18 | Identification of receptor domains binding to a ligand |
| VCAM-1 | VLA-4 | Study of role of VLA-4 in T lymphocyte migration to dermal inflammation sites |
| LFA-3 | CD2 | Study of role of CD2 in costimulation of T cells |
| L1 glycoprotein | Fibroblast growth factor receptor | Stimulation of nerve reproduction after repair; and functional comparison with FGF |

TABLE 2

Proteins involving immune response: Enzymes

| Enzymes | Ligands | Uses |
|---|---|---|
| Influenza C hemaglutinin esterase | 9-0-acetylated sialic acid | Inactive enzyme used in study of tissue-specific expression of ligands |
| Urokinase | Urokinase receptor | Inactive enzyme developed to inhibit cancer metastasis by disturbing urokinase activation |

TABLE 3

Proteins involving immune response: Cytokine receptors

| Cytokine receptors | Ligands | Uses |
|---|---|---|
| IFN-γ R α-chain | IFN-γ | Inhibition of IFN-mediated auto-immunity |
| IFN-γ R β-chain | IFN-γ | Study of structure of subunits of a ligand-receptor complex |
| IL1R | IL-1 | Inhibition of IL-1-mediated inflammation |
| IL4R | IL-4 | Identification of receptor domains participating in ligand binding |
| Erythropoietin R | Erythropoietin | Map design of epitopes of anti-ligand antibodies |
| cMp1 | Thrombopoietin | Isolation and cloning of ligands |
| gp130 | IL-6-IL6R complex | Study of structure of subunits of a ligand-receptor complex |

TABLE 4

Proteins involving immune response: Tumor necrosis factor receptors

| TNF receptors | Ligands | Uses |
|---|---|---|
| TNF R-1 | TNF, lymphotoxin-α | Treatment of septic shock, rheumatoid arthritis and other inflammatory diseases; and identification of domains participating in ligand binding |
| TNF R-2 | TNF, lymphotoxin-α | Inhibition of TNF-enriched HIV replication; and prevention of collagen-induced arthritis in mice |
| Lymphotoxin-β R | Lymphotoxin-β | Study of structure of subunits of cell surface lymphotoxin-β |
| Fas/Apo-1/CD95 | Fas/Apo-1/CD95 ligand | Treatment of excessive apoptosis and related diseases (e.g., AIDS); and resistance to apoptosis of lymphocytes and peripheral immune tolerance; roles of Fas ligand in T cell-mediated cytotoxicity; and isolation and cloning of ligands |
| CD27 | CD27 ligand | Isolation and cloning of ligands |
| CD30 | CD30 ligand | Isolation and cloning of ligands |
| CD40 | gp39 | Isolation and cloning of ligands |
| 4-1BB | 4-1BB ligand | Identification of tissues containing ligands by histochemical staining; isolation and cloning of ligands; and Study of structural determinant of potential ligand |
| OX40 | gp34 | Isolation and cloning of ligands |

TABLE 5

Proteins involving immune response: Receptor tyrosine kinases

| Receptor tyrosine kinases | Ligands | Uses |
|---|---|---|
| TrkA, B, C | Neutropin | Determination of properties of neutropin binding |
| Htk | Htk ligand | Isolation and cloning of ligands |
| REK7 | AL-1 | Isolation and cloning of ligands |
| Rse/Tyro-3 | Protein S, Gas6 | Identification of ligands and determination of their properties |
| Hepatocyte growth factor R | Hepatocyte growth factor | Identification of receptor domains participating in ligand binding |
| Platelet-derived growth factor R | Platelet-derived growth factor | Identification of receptor domains participating in ligand binding |
| Flt-1 | Vesicular endothelial growth factor (VEGF) | Determination of properties of ligand binding of receptors |
| Flk-1/KDR | VEGF | Evaluation of selectivity of receptors for VEGF versus placenta growth factor |

TABLE 6

Proteins involving immune response: Other cell surface proteins

| Other cell surface proteins | Ligands | Uses |
|---|---|---|
| B7 | CD28 | Study of T cell stimulation by B cells |
| B61 | Eck | Roles of Eck in inflammation |
| β-neurexin | β-neurexin ligand | Determination of properties of a signal sequence from β-neurexin |
| CD2 | LFA-3, CD48 | Identification of ligands |
| CD5 | CD5 ligand | Study of T cell stimulation by B cells |
| CD6 | ALCAM | Study of binding activities of cloned ligands |
| CD22 | CD45, other sialoglycoproteins | Identification of ligands; study on roles of CD22 in T-B-cell interaction; and determination of properties of binding determinants of sialo-oligo sugar ligands |
| CD28 | B7, B7-2 | Study of T cell stimulation by B cells |
| CD31 | CD31 | Identification of CD31 domains related to homotype binding |
| CD44 | Hyaluronate | Screening of tissues containing ligands by histochemical staining; and determination of properties of structural determinants of ligands |
| Complement R-2 (CD21) | C3 fragment | Inhibition of reactivity of antibody to immunosuppressive and cancer therapeutic agents |
| CTLA-4 | B7 | Identification of CTLA-4 as a secondary receptor of B7 |
| IgER | IgE | Inhibition of mast cell-binding of IgE as therapy of allergic diseases |
| Lisosome membrane gp-1 | LAMP-1 ligand | Design of epitope maps of anti-ligand antibodies |
| α2-microglobulin receptor-bound proteins | gp330 | Determination of position of ligands in tissues by histochemical staining |
| Sodium-releasing peptide R | Sodium-releasing peptide | Design of epitope maps of anti-ligand antibodies; and preparation of recombinant receptors for structural study |

TABLE 7

Proteins involving immune response: Soluble ligands

| Soluble ligands | Ligands | Uses |
|---|---|---|
| IL-2 | IL-2R | Extension of half-life of IL-2 in the circulation system |
| IL-10 | IL-10R | Therapy of septic shock and transplantation rejection; and extension of half-life of IL-10 in the circulation system |
| Heregulin | Her4/p180$^{erbB4}$ | Study of signal transduction by Her4 |
| Keratinocyte growth factor | Keratinocyte growth factor R | Determination of position of receptors by histochemical staining |

The term "soluble extracellular domain", as used herein, refers to a portion exposed to the extracellular region of an integral membrane protein penetrating the cell membrane comprising phospholipid, wherein the integral membrane protein contains one or more transmembrane domain made up predominantly of hydrophobic amino acids. Such an extracellular domain mainly comprises hydrophilic amino acids, which are typically positioned at the surface of a folded structure of a protein, and thus is soluble in an aqueous environment. For most cell surface receptor proteins, extracellular domains serve to bind specific ligands, while intracellular domains play an important role in signal transduction.

The term "concatamer-linked", as used herein, refers to a state in which two soluble domains of biologically active proteins are linked and thus form a long polypeptide.

The term "concatameric protein", as used herein, means a concatamer-linked protein. For example, the N-terminus of a soluble extracellular domain of a protein involving immune response is linked to the C-terminus of an identical soluble extracellular domain of the protein involving immune response, wherein the C-terminus of the former soluble extracellular domain is linked to the hinge region of an Fc fragment of an immunoglobulin molecule. Thus, two identical soluble extracellular domains of a protein involving immune response form a long polypeptide.

The term "simple fusion monomeric protein", as used herein, refers to a fusion protein having a monomeric structure consisting of a single polypeptide formed by linkage of a soluble extracellular domain of a protein involving immune response to the hinge region of an Fc fragment of an immunoglobulin molecule. A simple fusion monomeric protein may be designated "protein name/Fc" for convenience in the present invention. For example, a simple fusion monomeric protein produced by linkage of an soluble extracellular domain of TNFR1 protein involving immune response to an Fc fragment of an immunoglobulin molecule is designated TNFR1/Fc. If desired, the origin of the Fc fragment may be also specified in the designation. For example, in the case that the Fc fragment is derived from IgG1, the monomeric protein is called TNFR1/IgG1Fc.

The term "simple fusion dimeric protein", as used herein, refers to a fusion protein having a dimeric structure, in which two simple fusion monomeric proteins are joined by formation of intermolecular disulfide bonds at the hinge region. Such a simple fusion dimeric protein may be designated "[protein name/Fc]$_2$" for convenience in the present invention. For example, when fused by formation of intermolecular disulfide bonds at the hinge region of two simple fusion monomeric proteins produced by linkage of an soluble extracellular domain of TNFR1 protein and an Fc fragment of an immunoglobulin molecule, the resulting fusion protein having dimeric structure is designated [TNFR1/Fc]$_2$. In addition, the origin of the Fc fragment may be specified in the designation, if desired. For example, in the case that the Fc fragment is derived from IgG1, the dimeric protein is designated [TNFR1IgG1Fc]$_2$.

The term "concatameric fusion monomeric protein", as used herein, refers to a fusion protein having a monomeric structure consisting of a single polypeptide, in which the N-terminus of a soluble extracellular domain of a protein involving immune response is linked to the C-terminus of an identical soluble extracellular domain of the protein involving immune response, wherein the C-terminus of the former soluble extracellular domain is linked to the hinge region of an Fc fragment of an immunoglobulin molecule. A concatameric fusion monomeric protein may be designated "protein name-protein name/Fc" for convenience in the present invention. For example, when an soluble extracellular domain of TNFR1 of a simple fusion monomeric protein, produced by linkage of the soluble extracellular domain of TNFR1 protein involving immune response and an Fc fragment of an immunoglobulin molecule, is linked to an identical soluble extracellular domain of TNFR1, the resulting concatameric fusion monomeric protein is designated TNFR1-TNFR1/Fc. If desired, the origin of the Fc fragment may be specified in the designation. For example, in the case that the Fc fragment is derived from IgG1, the monomeric protein is designated TNFR1-TNFR1/IgG1Fc.

The term "concatameric fusion dimeric protein", as used herein, refers to a fusion protein having a dimeric structure, in which two concatameric fusion monomeric proteins are fused by formation of intermolecular disulfide bonds at the hinge region. A concatameric fusion dimeric protein may be designated "[protein name-protein name/Fc]$_2$" for convenience in the present invention. For example, when two concatameric fusion monomeric proteins, each of which is produced by linkage of a TNFR1 soluble extracellular domain of a simple fusion monomeric protein to an identical soluble extracellular domain of TNFR1 protein involving immune response, are fused by formation of intermolecular disulfide bonds at the hinge region, the resulting fusion protein having dimeric structure is designated [TNFR1-TNFR1/Fc]$_2$, wherein the simple fusion monomeric protein is formed by linkage of the TNFR1 soluble extracellular domain to an Fc fragment from an immunoglobulin molecule. If desired, the origin of the Fc fragment may be specified in the designation. For example, in the case that the Fc fragment is derived from IgG1, the fusion protein is designated [TNFR1-TNFR1/IgG1Fc]$_2$.

The term "vector", as used herein, means a DNA molecule serving as a vehicle capable of stably carrying exogeneous genes into host cells. For useful application, a vector should be able to replicate, have a system for introducing itself into a host cell, and possess selectable markers. The exogeneous genes, for example, include, a DNA construct encoding a concatameric fusion monomeric protein.

The term "recombinant expression plasmid", as used herein, refers to a circular DNA molecule carrying exogeneous genes operably linked thereto to be expressed in a host cell. When introduced into a host cell, the recombinant expression plasmid has the ability to replicate regardless of host chromosomal DNA, copy itself at a high copy number, and to produce heterogeneous DNA. As generally known in the art, in order to increase the expression level of a transfected gene in a host cell, the gene should be operably linked to transcription and translation regulatory sequences functional in a host cell selected as an expression system. Preferably, the expression regulation sequences and the exogeneous genes may be carried in a single expression vector containing. bacteria-selectable markers and a replication origin. In case that eukaryotic cells are used as an expression system, the expression vector should further comprise expression markers useful in the eukaryotic host cells.

The term "operably linked", as used herein, means an arrangement of elements of a vector, in which each element is capable of performing its innate function. Therefore, a control sequence operably linked to a coding sequence can influence expression of the coding sequence. A control sequence acting to induce expression of a coding sequence does not have to be adjacent to the coding sequence. For example, when an intervening sequence is present between a promoter sequence and a coding sequence, the promoter sequence may still be "operably linked" to the coding sequence.

Host cells used in the present invention may be prokaryotic or eukaryotic. In addition, host cells having high introduction efficiency of foreign DNA and having high expression levels of an introduced gene may be typically used. Examples of the host cells useful in the present invention include prokaryotic and eukaryotic cells such as *E. coli*, *Pseudomonas* sp., *Bacillus* sp., *Streptomyces* sp., fungi or yeast, insect cells such as *Spodoptera frugiperda* (Sf9), animal cells such as Chinese hamster ovary cells (CHO) or mouse cells, African green monkey cells such as COS 1, COS 7, human embryonic kidney cells, BSC 1, BSC 40 or BMT 10, and tissue-cultured human cells. When cloning a DNA construct encoding the fusion protein according to the present invention, host cells are preferably animal cells. When using COS cells, since SV40 large T antigen is expressed in COS cells, a plasmid carrying a SV 40 replication origin may be present as a multicopy episome and thus allows high expression of an exogeneous gene. A DNA sequence introduced into a host cell may be homogeneous or heterogeneous to the host cell, or a hybrid DNA sequence containing a homogenous or heterogeneous DNA sequence.

In order to express a DNA sequence encoding the concatameric fusion protein according to the present invention, a wide variety of combinations of host cells as an expression system and vectors may be used. Expression vectors useful for transforming eukaryotic host cells contain expression regulation sequences from, for example, SV40, bovine papillomavirus, adenovirus, adeno-associated viruses, cytomegalovirus and retroviruses. Expression vectors useful in bacterial host cells include bacterial plasmids from *E. coli*, which are exemplified by pBluescript, pGEX2T, pUC, pCR1, pBR322, pMB9 and derivatives thereof, plasmids having a broad range of host cells, such as RP4, phage DNAs, exemplified by a wide variety of λ phage derivatives including λ gt10, λ gt11 and NM989, and other DNA phages, exemplified by filamentous single-stranded DNA phages such as M13. Expression vectors useful in yeast cells include 2µ plasmid and derivatives thereof. Expression vectors useful in insect cells include pVL 941.

The term "transformation", as used herein, means introducing DNA into a suitable host cell so that the DNA is replicable, either as an extrachromosomal element, or by chromosomal integration.

The term "transfection", as used herein, refers to the taking up of an expression vector by a suitable host cell, whether any coding sequences are in fact expressed or not.

The term "signal sequence", as used herein, means an amino acid sequence mediating transport of an expressed protein to the outside of the cell membrane, and is also called a "leader sequence". Cell surface proteins or secretory proteins, which are transported to the outside of the cell membrane, have an N-terminal sequence typically cut by signal peptidase in the cell membrane. Such a N-terminal sequence is called a signal sequence or signal peptide, or a leader sequence or leader peptide. Secretory (or transported) proteins or all proteins present outside of the cell membrane or in the extracellular environment have a specific signal sequence. There is no specific homology between such signal sequences and same proteins have different signal sequences according to their origin. Secondary structure or distribution of nonpolar and charged residues is more important for proper function of the signal sequences than primary structures thereof. Although not having specific homology, the signal sequences share several common features, as follows. The signal sequences contain an N domain at their N-termini, which is a hydrophilic region comprising one or more positively charged residues, and an H-domain follows the N domain, which is a somewhat long hydrophobic region. In the case of *E. coli*, the signal sequence comprises about 18–30 amino acids. The N domain contains many cationic amino acids such as Lys or Arg, and thus has a net positive charge. Many hydrophobic amino acids such as Ala or Leu are found in the H domain, and polar or charged amino acids such as Pro, Lys, Arg, Asn or Glu are rarely in the H domain. A large number of amino acids such as Ala and Leu residues form an α-helical structure to facilitate membrane penetration. A C domain is positioned between the H domain and an actually secreted portion of a protein. The C domain is less hydrophobic, and contains a sequence capable of being recognized by signal peptidase such as LebB or LspA. There have been no reports about an exact site cleaved by the signal peptidase, but the signal peptidase is typically known to mostly cleave behind the Ala-X-Ala sequence in the C domain. Preproteins containing the above-mentioned signal sequence arrive at the cell membrane through interaction with several proteins, and fold to their mature forms through cleavage of a specific region of a signal peptide. Such a signal sequence is very important in strategies to express a desired protein on the cell surface or in the extracellular environment. Foreign proteins and fusion proteins should be stably transported to the extracellular environment at high efficiency. Typically, cell surface proteins having excellent secretory ability are useful for cell surface expression of foreign proteins or fusion proteins, which typically have secretory signal sequences capable of offering excellent secretion efficiency.

Preparation of the Concatameric Fusion Dimeric Protein According to the Present Invention The concatameric fusion dimeric protein according to the present invention is generally prepared by (a) preparing a DNA construct encoding a simple fusion monomeric protein using a gene encoding an Fc fragment of an immunoglobulin molecule and a gene encoding a soluble extracellular domain of a protein involving immune response; (b) inserting by polymerase chain reaction (PCR) a recognition sequence of a restriction enzyme into the prepared simple fusion monomeric protein-encoding DNA construct and an identical gene to the gene encoding a soluble extracellular domain of a protein involving immune response, respectively; (c) cleaving the recognition sequence of a restriction enzyme in the simple fusion monomeric protein-coding DNA construct and the gene encoding a soluble extracellular domain of a protein involving immune response using the restriction enzyme recognizing the recognition sequence; (d) ligating the cleaved DNA fragments using ligase to produce a DNA construct encoding a concatameric fusion monomeric protein (see, FIG. 2); (e) operably linking the prepared DNA construct encoding a concatameric fusion monomeric protein to a vector to produce a recombinant expression plasmid; (f) transforming or transfecting a host cell with the recombinant expression plasmid; and (g) culturing the transformant or transfectant under conditions suitable for expression of the DNA construct encoding a concatameric fusion monomeric protein and then isolating and purifying a concatameric fusion dimeric protein of interest.

A DNA fragment encoding a soluble extracellular domain of a protein involving immune response is produced by PCR using a primer containing a recognition sequence of a specific restriction enzyme and a sequence encoding a leader sequence, and a primer containing an antisense sequence encoding the 3' end of the soluble extracellular domain and a portion of the 5' end of a specific region of Fc fragment of an immunoglobulin molecule.

A DNA fragment encoding a specific region of the Fc fragment of an immunoglobulin molecule is produced by PCR using a primer having a sequence encoding a portion of the 3' end of the soluble extracellular domain of the protein involving immune response and a sequence encoding the 5' end of the specific region of the Fc fragment of an immunoglobulin molecule, and another primer having an anti-sense sequence encoding a recognition sequence of a specific restriction enzyme and the 3' end of a specific region of the Fc fragment of an immunoglobulin molecule.

The DNA fragment encoding a soluble extracellular domain of a protein involving the immune response and the DNA fragment encoding a specific region of Fc fragment of an immunoglobulin molecule, as described above, are mixed in a test tube. After denaturation, the DNA is re-annealed. Then, a complete double-stranded DNA fragment is produced by polymerization using DNA polymerase at the 3' end of each DNA hybrid. Using the resulting double-stranded DNA fragment, another polymerase chain reaction (PCR) is carried out with the primer having a sequence encoding a soluble extracellular domain of a protein involving immune response and the primer encoding the 3' end of a specific region of the Fc fragment of an immunoglobulin molecule, in order to amplify a immunoglobulin fusion gene comprising a sequence corresponding to the DNA fragment encoding a soluble extracellular domain of a protein involving immune response and a sequence corresponding to the DNA fragment encoding a specific region of the Fc fragment of an immunoglobulin molecule.

An recognition sequence of a restriction enzyme is introduced by PCR into the amplified immunoglobulin fusion gene and the DNA fragment having a sequence encoding a soluble extracellular domain of a protein involving the immune response. The recognition sequence is then cleaved with the restriction enzyme and the cleaved regions are ligated using ligase, thus producing a concatameric immunoglobulin fusion gene.

The immunoglobulin fusion gene may further include a signal sequence to stimulate extracellular secretion of a protein encoded thereby. For example, the CTLA-4 molecule contains a unique leader sequence having highly hydrophilic redundancy at its N-terminus, and which is abnormally long and highly water-soluble (Harper, K. et al., J. Immunol. 147:1037–1044; and Brunet, J.F. Nature 328: 267–270, 1987). Generally, most cell surface proteins or secretory proteins have a leader sequence comprising 20–24 highly hydrophobic amino acids at their N-Termini. However, the CTLA-4 molecule used in the present invention comprises a total of 37 residues: 16 hydrophilic amino acids at its N-terminus, and 21 highly hydrophobic amino acids typical in its transmembrane regions. In the conventional method of preparing CTLA4Ig fusion proteins, the leader sequence of the CTLA-4 molecule was substituted with a leader sequence of oncostatin M (Linsley, P.S. et al., J. Exp. Med. 174:561–569, 1991) or IL-6 (Yamada, A, et al., Microbiol. Immunol. 40:513–518, 1996). The present inventors demonstrated that a CTLA-4 molecule containing a leader sequence having a "MRTWPCTLLFFIPVFCKA" sequence instead of the amino acid sequence consisting of 16 amino acids, "ACLGFQRHKAQKNLAA", is preferable, and the secretion of an expressed protein to the extracellular environment is easily achieved, as disclosed in International Pat. Publication No. WO98/3 1820, of which content is incorporated herein as reference.

A recombinant expression plasmid is prepared by inserting the immunoglobulin fusion gene into a vector, and then introduced to a host cell to produce a transformant or transfectant. A concatameric fusion dimeric protein of interest may be obtained by culturing the transformant or transfectant cell and isolating and purifying a concatameric fusion protein.

A host cell useful for preparation of the concatameric fusion dimeric protein according to the present invention is preferably selected from among bone marrow cell lines, CHO cells, monkey COS cells, human embryonic kidney 293 cells, and baculovirus-infected insect cells. A polypeptide of interest, produced in such an expression system, is secreted to culture medium as an inclusion body. Then, the concatameric fusion dimeric protein can be purified by affinity chromatography using a protein A or protein G column. In fact, effective mammalian expression systems and such purification systems are very useful in expressing proteins involving immune response in a dimeric form, and isolation of such proteins.

Preparation of the Glycosylated Concatameric Fusion Dimeric Protein According to the Present Invention Secretory proteins produced in eukaryotic cells as host cells are modified by glycosylation. Glycosylation is known to influence in vivo stability and functionality as well as physical properties of a protein. Therefore, a preferred aspect of the present invention includes facilitating production of a concatameric fusion dimeric protein of interest using recombinant DNA techniques and the above-mentioned animal cell lines as host cells, and linking additional sugar chains to a soluble extracellular domain of a protein involving immune response.

Two glycosylation patterns are known. One is O-linked glycosylation, in which an oligosaccharide is linked to a serine or threonine residue, and the other is N-linked glycosylation, in which an oligosaccharide is linked to asparagine residue. N-linked glycosylation occurs at a specific amino acid sequence, particularly, Asn-X-Ser/Thr, wherein X is any amino acid excluding proline. N-linked oligosaccharide has a structure distinct from O-linked oligosaccharide, and glycosylated residues found in the N-linked type also differ from the O-linked type. For example, N-acetylgalactosamine is invariably linked to serine or threonine in O-linked oligosaccharide, while N-acetylglucosamine is linked to asparagines in all of N-linked oligosaccharides. The O-linked oligosaccharides generally contain only 1–4 sugar residues. In contrast, the N-linked oligosaccharides comprise 5 or more sugar residues, essentially including N-acetylglucosamine and mannose.

In accordance with the present invention, to allow additional O-linked or N-linked glycosylation, one or more nucleotides in a DNA sequence encoding a soluble extracellular domain of a protein involving immune response are altered, and the resulting DNA is expressed in a suitable animal host cell to induce glycosylation using the host system. In accordance with an aspect of the present invention, the glycosylated concatameric fusion dimeric protein according to the present invention may be prepared by altering a DNA sequence encoding a soluble extracellular domain of a protein involving immune response to induce or increase N-linked glycosylation by adding the sequence Asn-X-Ser/Thr.

Alteration of a DNA sequence to introduce glycosylation may be performed according to the conventional method common in the art. In a preferred aspect of the present invention, to protect the concatameric fusion protein, especially the two soluble extracellular domains, from attack of intercellular proteinases and thus increase its half-life in serum, a DNA construct encoding a multiglycosylated concatameric fusion monomeric protein may be prepared using PCR, which introduces multiglycosylation sites to the joint region between two soluble extracellular domains. In a specific aspect of the present invention, glycosylation motif peptide sequences may be introduced into the concatameric fusion protein, as follows. A DNA fragment is prepared by performing PCR using a primer encoding a leader sequence of a soluble extracellular domain and EcoRI restriction site, and an antisense primer in which a portion of a nucleotide sequence encoding a portion of the 3' end of a first soluble extracellular domain and a portion of the 5' end of a second soluble extracellular domain is substituted with glycosylation motif sequences. Another DNA fragment is prepared by performing PCR using a primer in which a portion of a nucleotide sequence encoding a portion of the 3' end of a first soluble extracellular domain and a portion of the 5' end of a second soluble extracellulular domain is substituted with glycosylation motif sequences, and an antisense primer encoding the 3' end of Fc portion of IgG1 and XbaI restriction site. Then, secondary PCR is carried out in a test tube using the two DNA fragments.

In accordance with an embodiment of the present invention, the soluble extracellular domains useful in the present invention include soluble extracellular domains of TNFR1, TNFR2, CD2 and CTLA-4. Their application will be described in detail with reference to accompanying figures, sequence listing and examples.

Tumor necrosis factor-alpha (TNF-α), which is known as the hormone cachectin, and tumor necrosis factor-beta (TNF-β), which is also known as lymphotoxin, are multifunctional cytokines, inducing inflammation, cellular immune response, septicemia, cytotoxicity, cachexia, rheumatoid arthritis, inflammation-related diseases (Tartaglia, L. A. et al., Immunol. Today 13:151,1992), and antiviral reaction (Butler, P., Peptide Growth Factor II, 1990, Springer-Verlag, Berlin, pp.39–70). Such actions of TNF-α and TNF-β, including cytotoxic activity, originate from their binding to TNF receptors in a trimeric form (Eck, M. J. et al., J. Biol. Chem. 267:2119, 1992). As TNF receptors, 55 kDa-type I (TNFR1 or p55) and about 75 kDa-type II (TNFR2 or p75) are known (Smith, C. A. et al., Science 248:1019, 1990; Loetscher, H. et al., Cell 61:351, 1990; and Schall et al., Cell 61:361, 1990). The two receptors have similar affinity for TNF-α and TNF-β (Schall et al., Cell 61:361, 1990). Immunoglobulin fusion proteins of such soluble receptors have effects of inhibiting the action of TNF-α and TNF-β by inhibiting binding of TNF-α and TNF-β to their receptors on the cell surface, which is known to be effective in reducing TNF-dependent inflammation.

Among cell surface antigens regulating immune response, the costimulatory molecule CD2 and CTLA-4, inducing secondary stimulation to give sufficient activation of T cells, when being in a soluble form, also can be used for therapy of diverse immunological diseases according to the same method as TNF receptors. Immune response is accomplished by binding of cell surface antigen molecules of antigen presenting cells (APC) to specific receptors of T lymphocytes, that is, T lymphocytes and leukocyte-function-antigen molecules of APC, and when a costimulatory signal as a secondary signal is not produced during antigen-presenting, T lymphocytes are removed by apoptosis or inhibition of clonal activation. CD2 is a leukocyte-function-antigen on T lymphocytes, binding to LFA-3 on APC, and participates in adhesion and costimulation of leukocytes, as well as stimulating T cell activation through costimulation with CD28. CTLA-4 is expressed after activation of T lymphocytes, and its expression level is increased in the resting phase. CTLA-4 has a binding affinity to the B7 molecule of APC over 20 times higher than that of CD28, and transduces signals inhibiting T lymphocyte activation after binding to B7.

In a specific aspect of the present invention, there are provided a concatameric fusion monomeric protein TNFR1-TNFR1/Fc, designated by SEQ ID NO: 6; a concatameric fusion monomeric protein TNFR2-TNFR2/Fc, designated by SEQ ID NO: 8; a concatameric fusion monomeric protein CD2-CD2/Fc, designated by SEQ ID NO: 18; and a concatameric fusion monomeric protein CTLA4-CTLA4/Fc, designated by SEQ ID NO: 20.

In another specific aspect of the present invention, there are provided a DNA construct (TNFR1-TNFR1-IgG) encoding a concatameric fusion monomeric protein TNFR1-TNFR1/Fc, designated by SEQ ID NO: 5; a DNA construct (TNFR2-TNFR2-IgG) encoding a concatameric fusion monomeric protein TNFR2-TNFR2/Fc, designated by SEQ ID NO: 7; a DNA construct (CD2-CD2-IgG) encoding a concatameric fusion monomeric protein CD2-CD2/Fc, designated by SEQ ID NO: 17; and a DNA construct (CTLA4-CTLA4-IgG) encoding a concatameric fusion monomeric protein CTLA4-CTLA4/Fc, designated by SEQ ID NO: 19.

In a further specific aspect of the present invention, there are provided a recombinant expression plasmid pTR11Ig-Top10' operably linked to a DNA construct encoding a concatameric fusion monomeric protein TNFR1-TNFR1/Fc, designated by SEQ ID NO: 5; a recombinant expression plasmid pTR22Ig-Top10' operably linked to a DNA construct encoding a concatameric fusion monomeric protein TNFR2-TNFR2/Fc, designated by SEQ ID NO: 7; a recombinant expression plasmid pCD22Ig operably linked to a DNA construct encoding a concatameric fusion monomeric protein CD2-CD2/Fc, designated by SEQ ID NO: 17; and a recombinant expression plasmid pCT44Ig operably linked to a DNA construct encoding a concatameric fusion monomeric protein CTLA4-CTLA4/Fc, designated by SEQ ID NO: 19. The recombination expression plasmids are deposited in Korean Culture Center of Microorganisms (KCCM) and are assigned accession Nos. KCCM-10288, KCCM-10291, KCCM-10402 and KCCM-10400, respectively. The KCCM deposit will be maintained under the terms of the Budapest Treaty on the International Recognition of the Deposit of Microorganisms for the Purposes of Patent Procedure.

In a further specific aspect of the present invention, there are provided a mammalian host cell (e.g., TR11Ig-CHO) transformed or transfected with a recombinant expression plasmid pTR11Ig-Top10' operably linked to a DNA construct encoding a concatameric fusion monomeric protein TNFRI-TNFR1/Fc, designated by SEQ ID NO: 5; a mammalian host cell (e.g., TR22Ig-CHO) transformed or transfected with a recombinant expression plasmid pTR22JG-Top10' operably linked to a DNA construct encoding a concatameric fusion monomeric protein TNFR2-TNFR2/Fc, designated by SEQ ID NO: 7; a mammalian host cell transformed or transfected with a recombinant expression plasmid pCD22Ig operably linked to a DNA contruct encoding a concatameric fusion monomeric protein CD2-CD2/Fc, designated by SEQ ID NO: 17; and a mammalian host cell transformed or transfected with a recombinant expression plasmid pCT44Ig operably linked to a DNA construct encoding a concatameric fusion monomeric protein CTLA4-CTLA4/Fc, designated by SEQ ID NO: 19. Chinese hamster ovary cell line TR11Ig-CHO transfected with the recombinant expression plasmid pTR11Ig-Top10' and Chinese hamster ovary cell line TR22Ig-CHO transfected with the recombinant expression plasmid pTR22Ig-Top10' are deposited in KCCM and are assigned accession Nos. KCLRF-BP-00046 and KCLRF-BP-00047, respectively. The KCCM deposit will be maintained under the terms of the Budapest Treaty on the International Recognition of the Deposit of Microorganisms for the Purposes of Patent Procedure.

In a still further specific aspect of the present invention, there are provided a concatameric fusion monomeric protein mgTNFR1-TNFR1/Fc containing glycosylation motif peptides, designated by SEQ ID NO: 10; a concatameric fusion monomeric protein mgTNFR2-TNFR2/Fc containing glycosylation motif peptides, designated by SEQ ID NO: 12; a concatameric fusion monomeric protein mgCD2-CD2/Fc containing glycosylation motif peptides, designated by SEQ ID NO: 22; and a concatameric fusion monomeric protein mgCTLA4-CTLA4/Fc containing glycosylation motif peptides, designated by SEQ ID NO: 24.

In a still further specific aspect of the present invention, there are provided a DNA construct encoding a concatameric fusion monomeric protein mgTNFR1-TNFR1/Fc containing glycosylation motif peptides, designated by SEQ ID NO: 9; a DNA construct encoding a concatameric fusion monomeric protein mgTNFR2-TNFR2/Fc containing glycosylation motif peptides, designated by SEQ ID NO: 11; a DNA construct encoding a concatameric fusion monomeric protein mgCD2-CD2/Fc containing glycosylation motif peptides, designated by SEQ ID NO: 21; and a DNA construct encoding a concatameric fusion monomeric protein mgCTLA4-CTLA4/Fc containing glycosylation motif peptides, designated by SEQ ID NO: 23. In order to produce a glycosylation motif peptide, a primer set (forward and reverse primers) is designed, which are complementary to a nucleotide sequence corresponding to the joint region between soluble extracellular domains of concatameric fusion proteins of TNFR/Fc, CD2/Fc and CTLA4/Fc, as well as containing codons encoding asparagine (N) (ATT and AAC) or codons encoding serine (S) and threonine (T) (TCC; and ACC, ACG and ACA, respectively), with which any codon in the concatameric fusion protein gene may be substituted. When designing the primer, selection of one among a plurality of amino acid sequences may be determined depending on a condition allowing minimum substitution of the nucleotide sequence and melting temperature ($T_m$) of each primer.

In a still further specific aspect of the present invention, there are provided a recombinant expression plasmid pTR11Ig-MG operably linked to a DNA construct encoding a concatameric fusion monomeric protein mgTNFR1-TNFR1/Fc containing glycosylation motif peptides, designated by SEQ ID NO: 9; a recombinant expression plasmid pTR22Ig-MG operably linked to a DNA construct encoding a concatameric fusion monomeric protein mgTNFR2-TNFR2/Fc containing glycosylation motif peptides, designated by SEQ ID NO: 11; a recombinant expression plasmid pCD22Ig-MG operably linked to a DNA construct encoding a concatameric fusion monomeric protein mgCD2-CD2/Fc containing glycosylation motif peptides, designated by SEQ ID NO: 21,; and a recombinant expression plasmid Pct44Ig-MG operably linked to a DNA construct encoding a concatameric fusion monomeric protein mgCTLA4-CTLA4/Fc containing glycosylation motif peptides, designated by SEQ ID NO: 23. The recombination expression plasmids are deposited in Korean Culture Center of Microorganisms (KCCM) and are assigned accession Nos. KCCM-10404, KCCM-10407, KCCM-10401 and KCCM-10399, respectively. The KCCM deposit will be maintained under the terms of the Budapest Treaty on the International Recognition of the Deposit of Microorganisms for the Purposes of Patent Procedure.

In a still further specific aspect of the present invention, there are provided a mammalian host cell transformed or transfected with a recombinant expression plasmid pTR11Ig-MG operably linked to a DNA construct encoding a concatameric fusion monomeric protein mgTNFR1-TNFR1/Fc containing glycosylation motif peptides, designated by SEQ ID NO: 9; a mammalian host cell transformed or transfected with a recombinant expression plasmid pTR22Ig-MG operably linked to a DNA construct encoding a concatameric fusion monomeric protein mgTNFR2-TNFR2/Fc containing glycosylation motif peptides, designated by SEQ ID NO: 11; a mammalian host cell transformed or transfected with a recombinant expression plasmid pCD22Ig-MG operably linked to a DNA construct encoding a concatameric fusion monomeric protein mgCD2-CD2/Fc containing glycosylation motif peptides, designated by SEQ ID NO: 21; and a mammalian host cell transformed or transfected with a recombinant expression plasmid Pct44Ig-MG operably linked to a DNA construct encoding a concatameric fusion monomeric protein mgCTLA4-CTLA4/Fc containing glycosylation motif peptides, designated by SEQ ID NO: 23.

The concatameric fusion dimeric proteins of the present invention may be isolated from culture medium after culturing the transformants or transfectants according to the present invention. The concatameric fusion dimeric proteins may participate in immune response, as described in Table 1, above, and are thus useful as therapeutic agents, diagnostic agents and laboratory tools according to the kinds of the protein, and their use is well known to those of ordinary skill in the art. In particular, when being used as therapeutic agents, the concatameric fusion dimeric proteins may be applied at an therapeutically effective amount common in the art, and it will be understood that such an amount may vary depending on diverse factors including activity of the used compound, patient's age, body weight, health state, sex and diet, administration time, administration route, combination of drugs, and pathogenic state of a specific disease to be prevented or treated. In addition, when being used as therapeutic agents, it will be understood that the concatameric fusion dimeric proteins according to the present invention may be applied by the typical methods and routes for administration of proteins involving immune response, which are known to those of ordinary skill in the art.

The present invention will be explained in more detail with reference to the following examples in conjunction with the accompanying drawings. However, the following examples are provided only to illustrate the present invention, and the present invention is not limited to them. For convenience in describing the present invention, information on DNA constructs, recombinant expression plasmids and transformed cell lines, which are prepared according to the Examples, below, and the used primers and accession numbers is summarized in Tables 8 and 9, below.

TABLE 8

Information on DNA constructs and accession Nos.

| DNA construct name | SEQ ID No. DNA | SEQ ID No. Protein | Deposition of genes Designation | Deposition of genes Accession No. | Deposition of cell lines Designation | Deposition of cell lines Accession No. |
|---|---|---|---|---|---|---|
| TNFR1-IgG | 1 | 2 | | | | |
| INFR2-IgG | 3 | 4 | | | | |
| TNFR1-TNFR1-IgG | 5 | 6 | pTR11Ig-Top10' | KCCM 10288 | TR11Ig-CHO | KCLRF-BP-00046 |
| TNFR2-TNFR2-IgG | 7 | 8 | pTR22Ig-Top10' | KCCM 10291 | TR22Ig-CHO | KCLRF-BP-00047 |
| mgTNFR1-TNFR1-IgG | 9 | 10 | pTR11Ig-MG | KCCM 10404 | | |
| mgTNFR2-TNFR2-IgG | 11 | 12 | PTR22Ig-MG | KCCM 10407 | | |
| CD2-IgG | 13 | 14 | | | | |
| CTLA4-IgG | 15 | 16 | | | | |
| CD2-CD2-IgG | 17 | 18 | pCD22Ig | KCCM 10402 | | |
| CTLA4-CTLA4-IgG | 19 | 20 | pCT44Ig | KCCM 10400 | | |
| mgCD2-CD2-IgG | 21 | 22 | pCD22Ig-MG | KCCM 10401 | | |
| mgCTLA4-CTLA4-IgG | 23 | 24 | pCT44Ig-MG | KCCM 10399 | | |

TABLE 9

Information for primers

| Primer name | SEQ ID No. | Description |
|---|---|---|
| Oligo TNFR-EDF-EcoRI | 25 | Containing 5' end of the extracellular domain of TNFR1 and an EcoRI site |
| Oligo TNFR-EDR-IgGh | 26 | Reverse primer containing 3' end of the extracellular domain of TNFR1 and the hinge region of IgG |
| Oligo IgG1-T1F | 27 | Containing 5' end of the hinge region of IgG and 3' end of TNFR1 |
| Oligo IgG1-R-XbaI | 28 | Reverse primer containing 3' end of the hinge region of IgG and a XbaI site |
| Oligo TNFR2-EDF-EcoRI | 29 | Containing 5' end of the extracellular domain of TNFR2 and an EcoRI site |
| Oligo TNFR2-EDR-IgGh | 30 | Reverse primer containing 3' end of the extracellular domain of TNFR2 and the hinge region of IgG |
| Oligo IgG1-T2F | 31 | Containing 5' end of the hinge region of IgG and 3' end of TNFR2 |
| Oligo TNFR1-CF-BamHI | 32 | Containing 5' end of the extracellular domain of TNFR1 and a BamHI site; and used for preparation of a concatamer |
| Oligo TNFR1-NR-BamHI | 33 | Reverse primer containing 3' end of the extracellular domain of TNFR1 and a BamHI site; and used for preparation of a concatamer |
| Oligo TNFR2-CF-BamHI | 34 | Containing 5' end of the extracellular domain of TNFR2 and a BamHI site; and used for preparation of a concatamer |
| Oligo TNFR2-NR-BamHI | 35 | Reverse primer containing 3' end of the extracellular domain of TNFR2 and a BamHI site; and used for preparation of a concatamer |
| Oligo mgTNFR1-TNFR1-IgG-F | 36 | Primer for mutagenesis, containing a sequence capable of inserting glycosylation sites into the joint region of TNFR1-TNFR1, and sequences corresponding to 3' end and 5' end of TNFR1; and used for preparation of a MG (multiglycosylation) form |
| Oligo mgTNFR1-TNFR1-IgG-R | 37 | Reverse primer for mutagenesis, containing a sequence capable of inserting glycosylation sites into the joint region of TNFR1-TNFR1, and sequences corresponding to 3' end and 5' end of TNFR1; and used for preparation of a MG form |
| Oligo mgTNFR2-TNFR2-IgG-F | 38 | Primer for mutagenesis, containing a sequence capable of inserting glycosylation sites into the joint region of TNFR2-TNFR2, and sequences corresponding to 3' end and 5' end of TNFR2; and used for preparation of a MG form |
| Oligo mgTNFR2-TNFR2-IgG-R | 39 | Reverse primer for mutation, containing a sequence capable of inserting glycosylation sites into the joint region of TNFR2-TNFR2, and sequences corresponding to 3' end and 5' end of TNFR2; and used for preparation of a MG form |
| Oligo CD2F-EcoRI | 40 | Containing 5' end of the extracellular domain of CD2 and a EcoRI site |
| Oligo CD2R-RstI | 41 | Containing 3' end of the extracellular domain of CD2 and a PstI site |
| Oligo IgG-F-PstI | 42 | Containing 5' end of the hinge region of IgG and a PstI site |
| Oligo CTLA4F-EcoRI | 43 | Containing 5' end of the hinge domain of CTLA-4 and a EcoRI site |
| Oligo CTLA4R-PstI | 44 | Containing 3' end of the extracellular domain of CTLA-4 and a PstI site |
| Oligo CD2-NT-F | 45 | Containing 5' end of the extracellular domain of CD2; and used for preparation of a concatamer |
| Oligo CD2-CT-R | 46 | Reverse primer containing 3' end of the extracellular domain of CD2; and used for preparation of a concatamer |
| Oligo CTLA4-NT-F | 47 | Containing 5' end of the extracellular domain of CTLA-4; and used for preparation of a concatamer |
| Oligo CTLA4-CT-R | 48 | Reverse primer containing 3' end of the extracellular domain of CTLA-4; and used for preparation of a concatamer |
| Oligo mgCD2-CD2-IgG-F | 49 | Used for preparation of a MG (multiglycosylation) form of CD2-CD2-IgG |
| Oligo mgCD2-CD2-IgG-R | 50 | Reverse primer used for preparation of a MG (multiglycosylation) form of CD2-CD2-IgG |
| Oligo mgCTLA4-CTLA4-IgG-F | 51 | Used for preparation of a MG (multiglycosylation) form of CTLA-4-CTLA-4-IgG |

TABLE 9-continued

Information for primers

| Primer name | SEQ ID No. | Description |
|---|---|---|
| Oligo mgCTLA4-CTLA4-IgG-R | 52 | Reverse primer used for preparation of a MG (multiglycosylation) form of CTLA4-CTLA4-IgG |

EXAMPLE 1

Human TNFR

Figure 5:
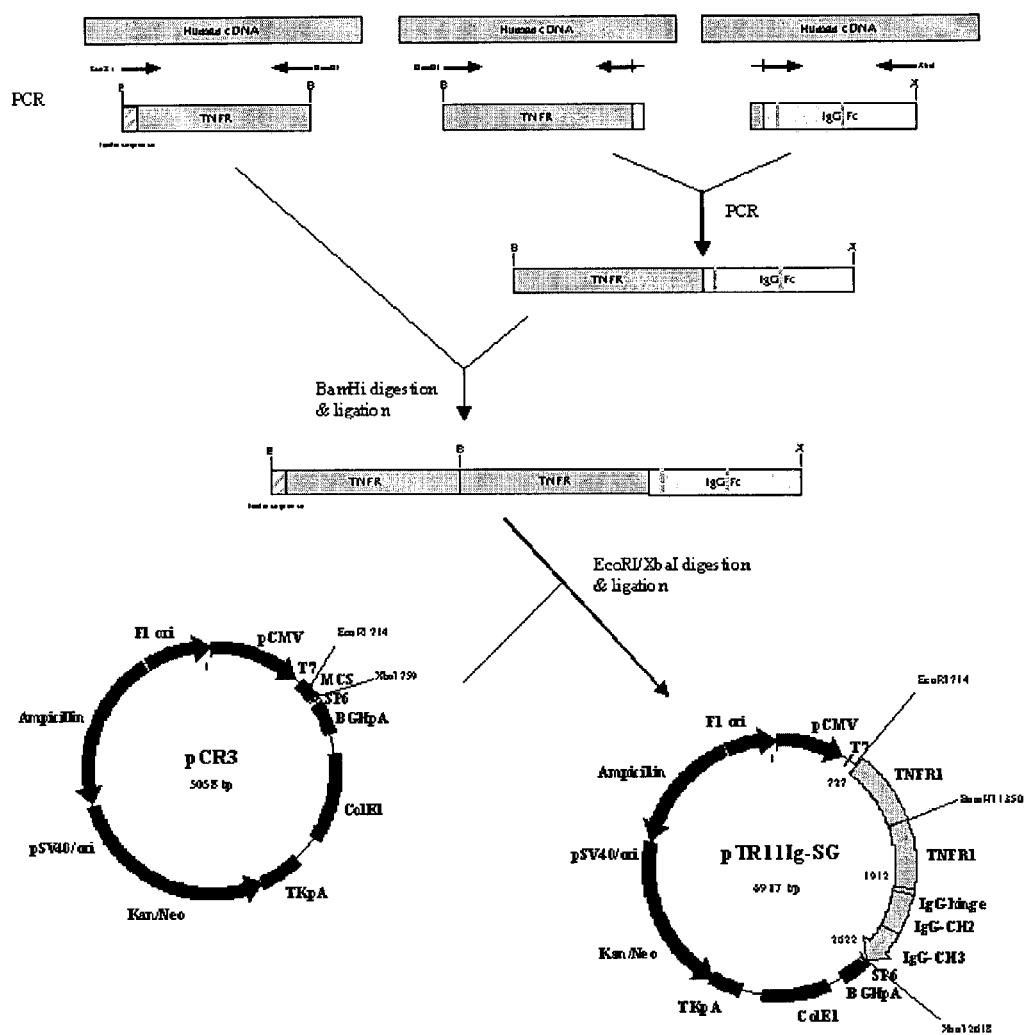
FIG. 5 is a diagram showing a process of constructing a recombinant expression plasmid pTR11Ig-Top10' expressing a concatameric fusion monomeric protein TNFR1-TNFR1/Fc according to the present invention.
Figure 6:
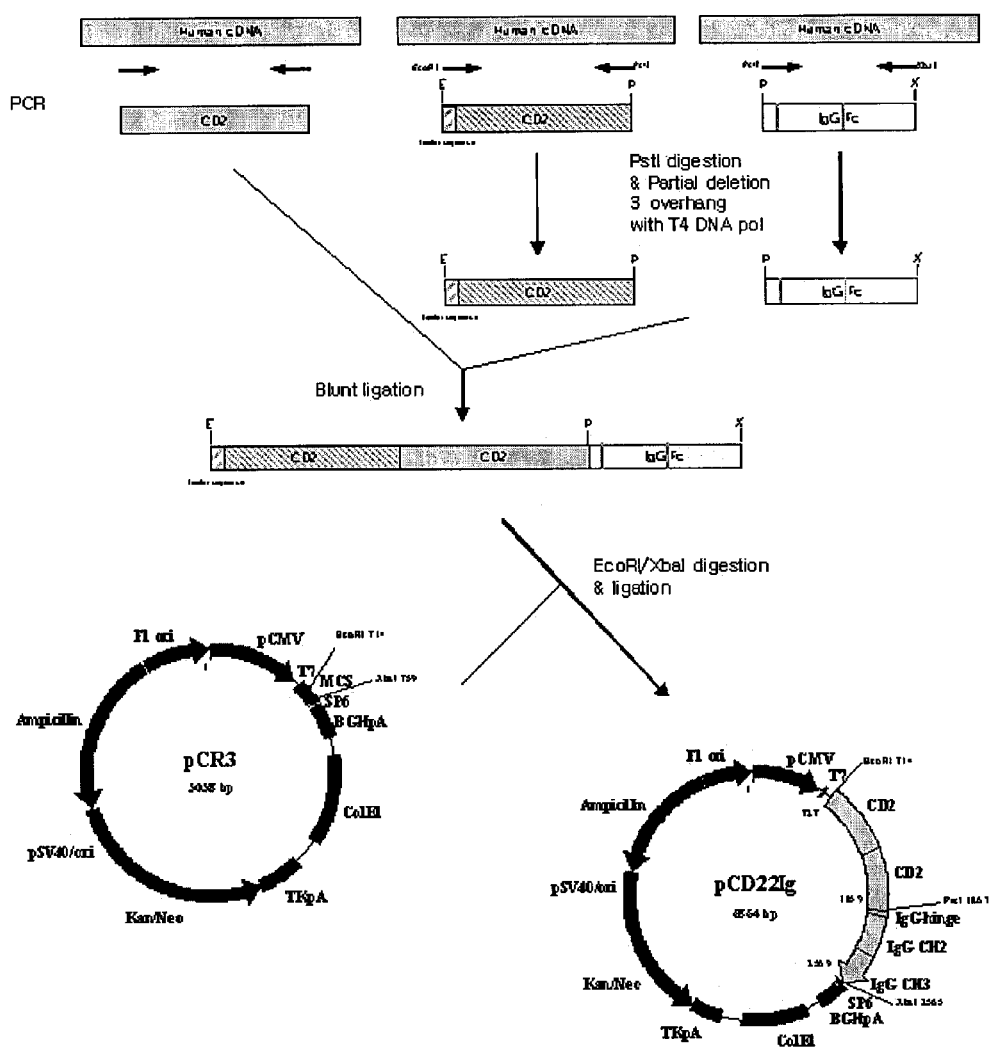
FIG. 6 is a diagram showing a process of constructing a recombinant expression plasmid pCD22Ig expressing a concatameric fusion monomeric protein CD2-CD2/Fc according to the present invention.

A. Manufacture of a DNA Construct Encoding Simple Fusion Monomeric Protein of TNFR1/Fc (FIG. 1 and FIG. 5)

a. DNA Fragment Encoding Soluble Extracellular Domain of TNFR1

A fusion gene encoding soluble extracellular domain of type I human TNF receptor (TNFR1, p55) and Fc fragment of human immunoglobulin G1 was constructed by the Polymerase Chain Reaction (PCR) method described in the prior art (Holten et al., Biotechniques 8:528, 1990).

A DNA fragment encoding soluble extracellular domain of TNFR1 was constructed by PCR using a primer (the sequence of nucleotide of SEQ ID NO: 25) with EcoRI restriction site and the sequence encoding leader sequence (the sequence of amino acids 1–20 of SEQ ID NO: 2), and an antisense primer (the sequence of nucleotide of SEQ ID NO: 26) with the sequence encoding a part of 3' ends of the said soluble extracellular domain of TNFR1 (TNFR1-ED) and 5' ends of the hinge region of immunoglobulin G1 (IgG1). The template cDNA for this reaction was constructed by reverse transcription PCR (RT-PCR) of mRNA extracted from monocyte (T lymphocyte) of healthy adults.

After blood of healthy adults was extracted and diluted to 1:1 with RPMI-1640 (Gibco BRL, USA), the layer of T lymphocyte which formed at upper part was obtained by density gradient centrifugation using Ficoll-hypaque (Amersham, USA). In order to make the concentration of the cell to $5 \times 10^5$ cells/ml, the cell was washed with RPMI-1640 for 3 times, and RPMI-1640 culture media containing 10% Fetal Bovine Serum (FBS, Gibco BRL, USA) was added, then cultured at 37° C. for two days in the 5% $CO_2$ incubator after adding leukoagglutinin to 3.5 ug/ml (Pharmacia, USA).

The mRNAs were purified using Tri-Reagent (MRC, USA) mRNA purification kit. First, $2 \times 10^7$ of human T lymphocyte was washed with Phosphate Buffered Saline (PBS, pH7.2) for 3 times, and then 1 ml of Tri-Reagent was mixed for several times to dissolve RNA. After adding 0.2 ml of chloroform to this tube and mixing thoroughly, this tube was incubated at room temperature (RT) for 15 min, then centrifuged at 15,000 rpm, 4° C. for 15 min. The upper part of the solution was transferred to a 1.5 ml tube, and 0.5 ml of isopropanol was added, and then centrifuged at 15,000 rpm, 4° C. for 15 min. After the supernatant was discarded, the pellet was resuspended with 1 ml of 3° distilled water treated with 75% ethanol-25% DEPC (Sigma, USA), and then centrifuged at 15,000 rpm, 4° C. for 15 min. After the supernatant was removed completely and dried in the air to remove ethanol residue, RNA was resuspended with 50µl of 3° distilled water treated with DEPC.

The primary cDNA was synthesized by mixing 2µg of purified mRNA and 1µl of oligo dT (dT30, Promega, USA) primer to 10µM in 1.5 ml tube, heating at 70° C. for 2 min, and cooling in ice for 2 min. After that, this mixture was added with 200 U of M-MLV reverse transcriptase (Promega, USA), 10 µl of 5× reaction buffer (250 mM Tris-HCl, pH 8.3, 375 mM KCl, 15 mM $MgCl_2$, and 50 mM DTT), 1 µl of dNTP (10 mM each, Takara, Japan), and DEPC-treated 3° distilled water to 50 µl, then reacted at 42° C. for 1 hour.

b. DNA Fragment Encoding Fc Fragment of Immunoglobulin

A DNA fragment encoding Fc fragment of immunoglobulin G1 was constructed by PCR using a primer (the sequence of nucleotide of SEQ ID NO: 27) with the sequence encoding a part of 3' ends of the said soluble extracellular domain of TNFR and 5' end of the hinge region of immunoglobulin G1 (IgG1), and an antisense primer (the sequence of nucleotide of SEQ ID NO: 28) with XbaI restriction site and the sequence encoding 3' ends of IgG1 Fc. The template cDNA for this reaction was constructed by RT-PCR of mRNA extracted from peripheral blood cell (B lymphocyte) of convalescent patients with pyrexia of unknown origin.

c. DNA Construct Encoding Simple Fusion Monomeric Protein of TNFR1/Fc

After DNA fragment encoding soluble extracellular domain of TNFR1 and DNA fragment encoding Fc fragment of immunoglobulin produced as described above were mixed in the same tube, complementary binding between the common sequence (the sequence including 3' end of soluble extracellular domain of TNFR1 and 5' end of IgG1 hinge region) was induced. Using this mixture as a template, DNA construct including DNA fragment encoding soluble extracellular domain of TNFR1 and DNA fragment encoding IgG1 Fc fragment was amplified by PCR using a primer (the sequence of nucleotide of SEQ ID NO: 25) with the sequence encoding 5' end of TNFR1 and another primer (the sequence of nucleotide of SEQ ID NO: 28) with the sequence encoding 3' end of IgG1 Fc. The constructed gene included a leader sequence to faciliate secretion of protein after expression.

d. Cloning of the DNA Construct Encoding Simple Fusion Monomeric Protein of TNFR1/Fc DNA construct encoding simple fusion monomeric protein of TNFR1/Fc as described above was restricted with EcoRI and XbaI, and cloned by inserting into a commercially available cloning vector, pBluescript KS II (+) (Stratagene, USA), at EcoRI/XbaI site. The sequence of a total coding region was identified by DNA sequencing (SEQ ID NO: 1). This produced fusion protein was designated TNFR1/Fc as simple fusion monomeric protein, and the elliptical shape shown in FIG. 1 represents the structure of a primary expression product of the fusion gene. The deduced amino acid sequence of simple fusion monomeric of TNFR1/Fc corresponded to SEQ ID NO: 2.

B. Manufacture of a DNA Construct Encoding Simple Fusion Monomeric Protein of TNFR2/Fc (FIG. 1 and FIG. 5)

a. DNA Fragment Encoding Soluble Extracellular Domain of TNFR2

A fusion gene encoding soluble extracellular domain of type II human TNF receptor (TNFR2, p75) and Fc fragment of human immunoglobulin G1 was constructed by the same method as that of TNFR1/Fc.

A DNA fragment encoding soluble extracellular domain of TNFR2 was constructed by PCR using a primer (the sequence of nucleotide of SEQ ID NO: 29) with EcoRI restriction site and the sequence encoding leader sequence (the sequence of amino acids 1–22 of SEQ ID NO: 4), and an antisense primer (the sequence of nucleotide of SEQ ID NO: 30) with the sequence encoding a part of 3' ends of said soluble extracellular domain of TNFR2 (TNFR2-ED) and 5' ends of the hinge region of immunoglobulin G1 (IgG1). The template cDNA for this reaction was constructed by RT-PCR of mRNA extracted from monocyte (T lymphocyte) of healthy adults.

b. DNA Construct Encoding Simple Fusion Monomeric Protein of TNFR2/Fc

After DNA fragment encoding soluble extracellular domain of TNFR2 and DNA fragment encoding Fc fragment of immunoglobulin G1 produced as described above were mixed in the same tube, complementary binding between the common sequence (the sequence including 3' end of soluble extracellular domain of TNFR2 and 5' end of IgG1 hinge region) was induced. Using this mixture as a template, DNA construct including DNA fragment encoding soluble extracellular domain of TNFR2 and encoding and DNA fragment encoding IgG1 Fc fragment was amplified by PCR using a primer (the sequence of nucleotide of SEQ ID NO: 29) with the sequence encoding 5' end of TNFR2 and another primer (the sequence of nucleotide of SEQ ID NO: 28) with the sequence encoding 3' end of IgG1 Fc. The constructed gene includes a sequence to faciliate secretion of protein after expression.

c. Cloning of the DNA Construct Encoding Simple Fusion Monomeric Protein of TNFR2/Fc DNA construct encoding simple fusion monomeric protein of TNFR2/Fc as described above was restricted with EcoRI and XbaI, and cloned by inserting into a commercially available cloning vector, pBluescript KS II (+) (Stratagene, USA), at EcoRI/XbaI site. The sequence of a total coding region was identified by DNA sequencing (SEQ ID NO: 3). This produced fusion protein was designated TNFR2/Fc as simple fusion monomeric protein, and the elliptical shape shown in FIG. 1 represents the structure of a primary expression product of the fusion gene. The deduced amino acid sequence of simple fusion monomeric of TNFR2/Fc corresponded to SEQ ID NO: 4.

Figure 2:
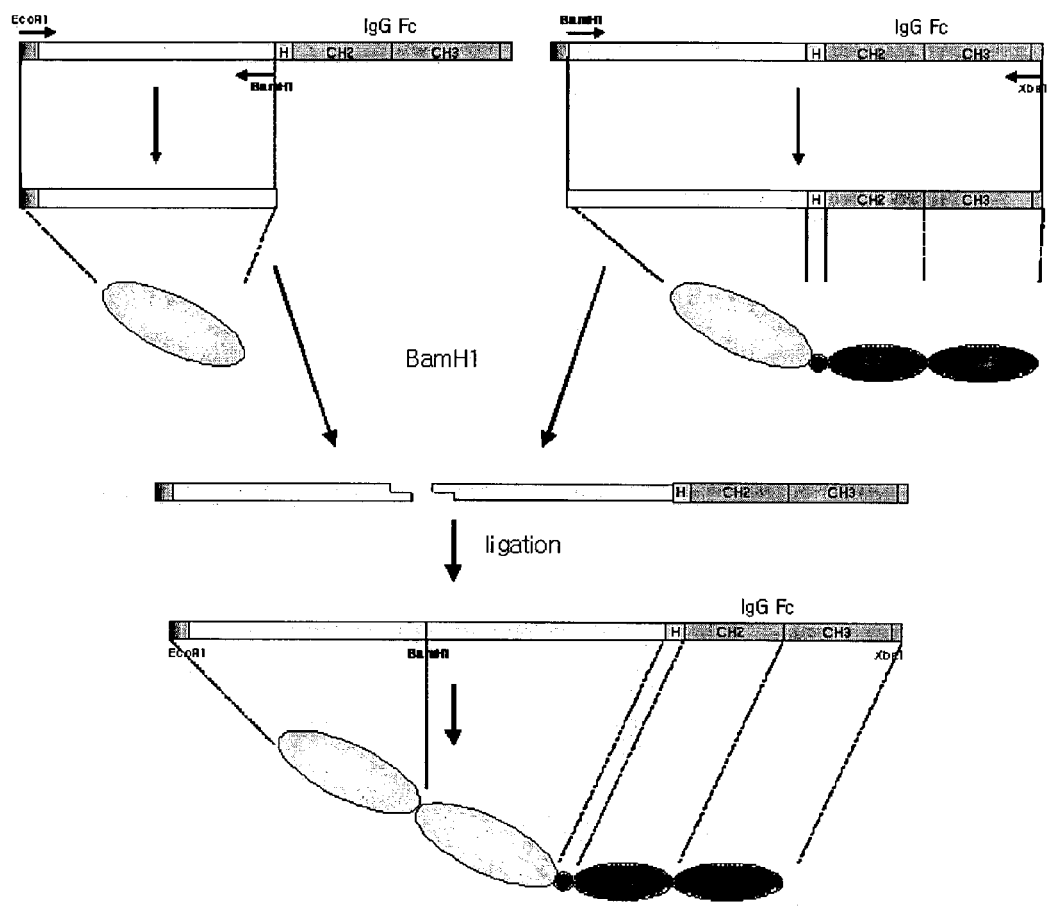
FIG. 2 is a schematic view showing a process of preparing a DNA construct encoding a concatameric fusion monomeric protein according to the present invention through PCR.
Figure 3:
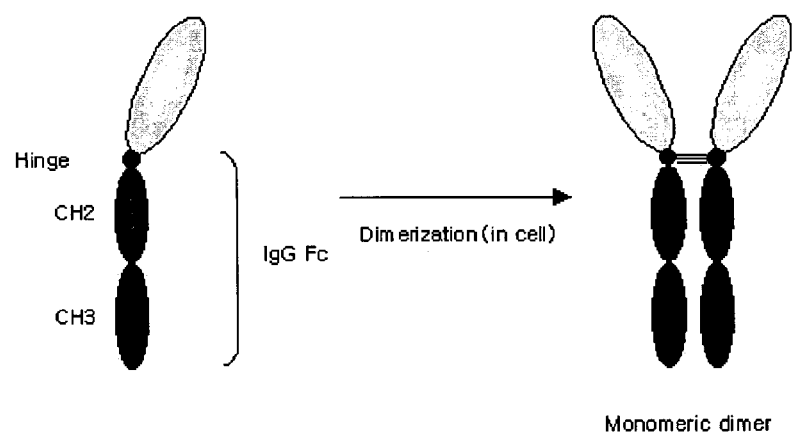
FIG. 3a shows structures of [TNFR/Fc]$_2$, [CD2/Fc]$_2$ or [CTLA4/Fc]$_2$ fusion proteins, which are simple fusion dimeric proteins formed through homodimerization in cells of TNFR/Fc, CD2/Fc or CTLA4/Fc fusion proteins as examples of conventional simple fusion monomeric proteins.
FIG. 3b shows structures of [TNFR-TNFR/Fc]$_2$, [CD2-CD2/Fc]$_2$ or [CTLA4-CTLA4/Fc]$_2$ fusion proteins, which are concatameric fusion dimeric proteins formed through homodimerization in cells of TNFR-TNFR/Fc, CD2-CD2/Fc or CTLA4-CTLA4/Fc fusion proteins as embodiments of the concatameric fusion dimeric protein according to the present invention.
Figure 3:
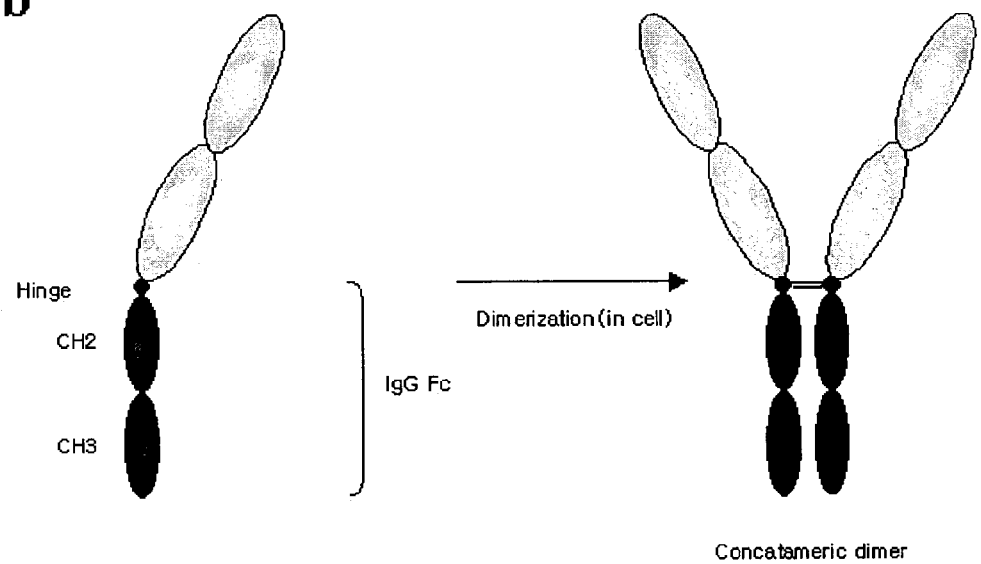
Figure 4:
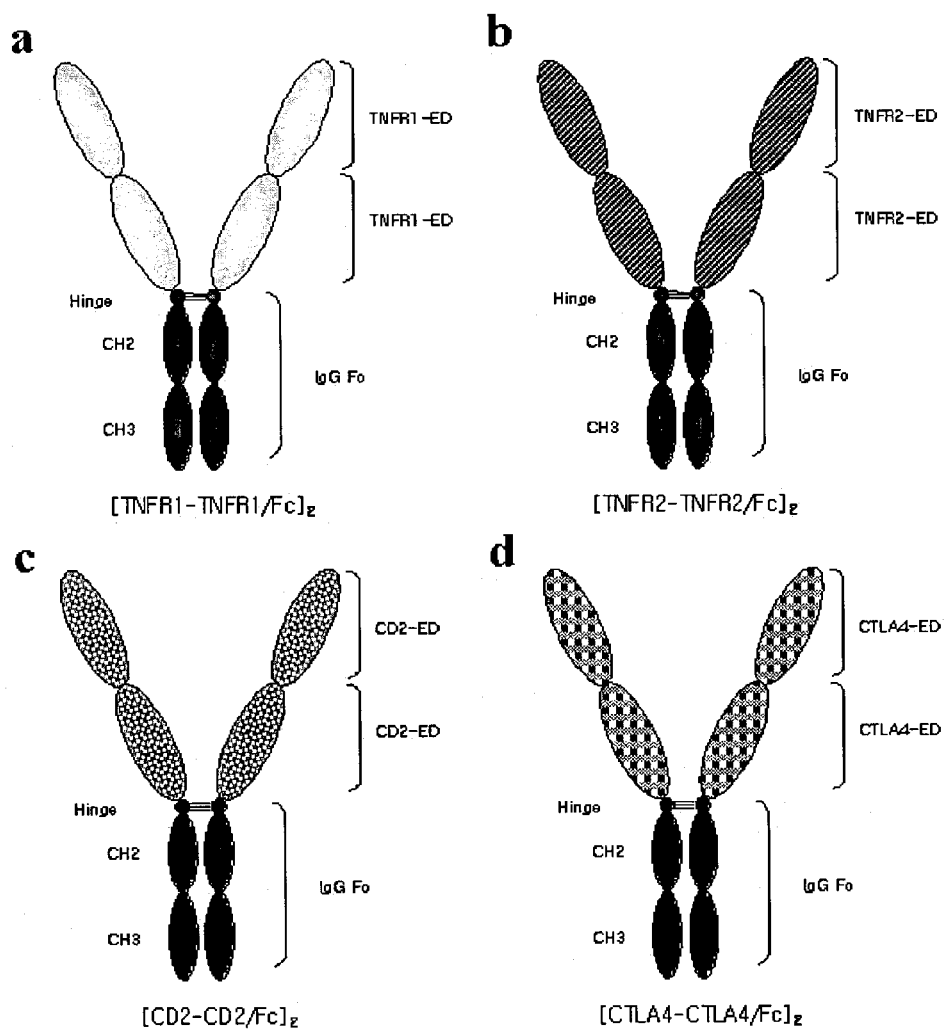
FIG. 4a shows a structure of [TNFR1-TNFR1/Fc]$_2$, as an embodiment of a concatameric fusion dimeric protein according to the present invention.
FIG. 4b shows a structure of [TNFR2-TNFR2/Fc]$_2$, as another embodiment of the concatameric fusion dimeric protein according to the present invention.
FIG. 4c shows a structure of [CD2-CD2/Fc]$_2$, as a further embodiment of the concatameric fusion dimeric protein according to the present invention.
FIG. 4d shows a structure of [CTLA4-CTLA4/Fc]$_2$, as a still further embodiment of the concatameric fusion dimeric protein according to the present invention.

C. Manufacture of a DNA Construct Encoding Concatameric Fusion Monomeric Protein of TNFR1-TNFR1/Fc (FIG. 2 and FIG. 5)

In order to manufacture a fusion gene comprising the concatameric shape in soluble extracellular domain of TNFR1, i.e. the DNA construct encoding concatameric fusion monomeric protein of TNFR1-TNFR1/Fc, BamHI restriction site was inserted respectively into the sequence of soluble extracellular domain of TNFR1 and DNA construct as produced as above encoding simple fusion monomeric protein of TNFR1/Fc by PCR, and then regions of each fragments restricted by BamHI were linked by ligase. The DNA construct, encoding simple fusion monomeric protein of TNFR1/Fc produced as above, was used as the template of this reaction.

The fragment of the soluble extracellular domain of TNFR1 with BamHI restriction site at 3' end was amplified by PCR using a primer corresponding to the nucleotide of SEQ ID NO: 25 and another primer corresponding to the nucleotide sequence of SEQ ID NO: 33, and the other fragment of simple fusion monomeric protein of TNFR1/Fc with BamHI restriction site at 5' end was amplified by PCR using a primer corresponding to the nucleotide of SEQ ID NO: 28 and another primer corresponding to the nucleotide sequence of SEQ ID NO: 32, respectively. PCR was performed by adding 1 µl of primary cDNA, 2 U of Pfu DNA polymerase (Stratagene, USA), 10 µl of 10× reaction buffer [200 mM Tris-HCl, pH 8.75, 100 mM $(NH_4)_2SO_4$, 100 mM KCl, 20 mM $MgCl_2$], 1% Triton™ X-100, 1mg/ml BSA, 3 µl primer 1 (10 µM), 3 µl primer 2 (10 µM), 2 µl dNTP (10 mM each), and 3° distilled water to 100 µl. The reaction condition was as follows; 94° C., 5 min; 95° C., 1 min; 58° C., 1 min 30 see; 72° C., 1 min for 31 cycles; and 72° C., 15 min to make PCR product with complete blunt end.

After electrophorized on 0.8% agarose gel, the PCR product was purified by Qiaex II gel extraction kit (Qiagen, USA). The purified PCR product was restricted by BamHI and extracted by phenol-chloroform extraction methods. Subsequently, two kinds of DNA fragments restricted by BamHI were linked by ligase.

D. Manufacture of a DNA Construct Encoding Concatameric Fusion Monomeric Protein of TNFR2-TNFR2/Fc (FIG. 2 and FIG. 5)

After a BamHI restriction site was inserted respectively into the sequence of the soluble extracellular domain of TNFR21 and the DNA construct produced as described above encoding simple fusion monomeric protein of TNFR2/Fc by PCR, a DNA construct encoding concatameric fusion monomeric protein of TNFR2-TNFR2/Fc was manufactured by linking the regions of each fragments restricted by BamHI by ligase.

A fragment of soluble extracellular domain of TNFR2 with BamHI restriction site at 3' end was amplified using a primer corresponding the sequence of SEQ ID NO: 34 and SEQ ID NO: 35. PCR was performed as that of TNFR1, except that a DNA construct encoding simple fusion monomeric protein of SEQ ID NO: 3 produced as above was used as a template. The PCR product was purified by the method as that of TNFR1.

E. DNA Construct Encoding Concatameric Fusion Monomeric Protein of TNFR1-TNFR1/Fc with Glycosylation Motif.

A DNA fragment was manufactured by PCR using an antisense primer (the sequence of nucleotide of SEQ ID NO: 37) with the sequence encoding the part (the sequence of nucleotide 565–591 of SEQ ID NO: 5) of 3' end of the first soluble extracellular domain of TNFR1, except the sequence of hydrophobic peptide region (the sequence of amino acid 197–216 of SEQ ID NO: 6) at the junction of soluble extracellular domain of TNFR1 and the part (the sequence of nucleotide 649–681 of SEQ ID NO: 5) of 5' end of the second soluble extracellular domain of TNFR1, and another primer (the sequence of nucleotide of SEQ ID NO: 25) with the sequence encoding EcoRI restriction site and leader sequence.

In addition, the total four amino acid sequences encoding glycosylation site (the sequence of amino acids 189–191, 192–194, 198–200, and 204–206 of SEQ ID NO: 10) were inserted by manufacturing the primer as above (the sequence of nucleotide of SEQ ID NO: 36 and 37) corresponding the substitution of the nucleotide 565–567 (CTG, Leu), 574–576 (ACG, Thr), 652–654 (CTA, Leu), and 670–672 (AGA, Arg) of SEQ ID NO: 5 with the nucleotide of AAC (Asn, N); the nucleotide of 571–573 (TGC, Cys) and 580–582 (TTG, Leu) of SEQ ID NO: 5 with the nucleotide of ACC (Thr, T); the nucleotide of 658–660 (GAC, Asp) with the nucleotide of TCC (Ser, S).

In this reaction, the gene (the nucleotide of SEQ ID NO: 5) encoding concatameric shape of TNFR1-TNFR1/Fc was used as a template. During the primary PCR, only the half of the antisense primer was induced to bind the gene encoding concatameric shape of TNFR1-TNFR1/Fc used as a template, and, as chain reaction was proceeding, the unbound part to the template was induced to form a complete double-stranded DNA by polymerase, and then this was capable of producing the DNA fragment with state of linkage of the sequence of 5' end encoding the part of the second soluble extracellular domain and the sequence of 3' end encoding TNFR1 extracellular domain including leader sequence. Therefore, a part of the sequence of 5' end encoding the second soluble extracellular domain has the function that was capable of binding to the second DNA fragment as follows.

The second DNA fragment was manufactured by PCR using a primer (the sequence of nucleotide of SEQ ID NO: 36) with the sequence encoding the part (the sequence of nucleotide 565–591 of SEQ ID NO: 5) of 3' end of the first soluble extracellular domain of TNFR1 and the part (the sequence of nucleotide 649–681 of SEQ ID NO: 5) of 5' end of the second soluble extracellular domain of TNFR1, and an antisense primer (the sequence of nucleotide of SEQ ID NO: 28) with the sequence encoding a XbaI restriction site and 3' end of IgG1 Fc. This reaction was also performed as described above, that is, only the half of antisense primer was induced to bind the template, and consequently, DNA fragment like that described above had the sequence encoding 5' end of TNFR1 extracellular including the part of 3' end of the first soluble extracellular domain.

Subsequently, resulting from two kinds of DNA fragments as PCR described as above were mixed in the same tube, induced to bind between common sequences, and fused by PCR using primers (the sequence of nucleotide of SEQ ID NO: 25 and 28) encoding 5' and 3' end of each concatameric genes, and the product was designated mgT-NFR1-TNFR1-IgG.

F. DNA Construct Encoding Concatameric Fusion Monomeric Protein of TNFR2-TNFR2/Fc with Glycosylation Motif.

A DNA fragment was manufactured by PCR using an antisense primer (the sequence of nucleotide of SEQ ID NO: 39) with the sequence encoding the part (the sequence of nucleotide 586–606 of SEQ ID NO: 7) of 3' end of first soluble extracellular domain of TNFR2, except the sequence of hydrophobic peptide region (the sequence of amino acid 203–263 of SEQ ID NO: 8) at the junction of soluble extracellular domain of TNFR2 and the part (the sequence of nucleotide 790–807 of SEQ ID NO: 7) of 5' end of second soluble extracellular domain of TNFR2, and another primer (the sequence of nucleotide of SEQ ID NO: 29) with the sequence encoding EcoRI restriction site and leader sequence.

In addition, the total two amino acid sequences encoding glycosylation site (the sequence of amino acids 199–201 and 206–208 of SEQ ID NO: 12) were inserted by manufacturing the primer as described above (the sequence of nucleotide of SEQ ID NO: 38 and 39) corresponding to the substitution of the nucleotide 595–597 (GTC, Val) and 799–801 (GGG, Gly) SEQ ID NO: 7 with the nucleotide of AAC (Asn, N).

In this reaction, the gene (the nucleotide of SEQ ID NO: 7) encoding concatameric shape of TNFR2-TNFR2/Fc was used as a template. During the primary PCR, only the half of antisense primer was induced to bind the gene encoding concatameric shape of TNFR2-TNFR2/Fc used as a template, and, as the chain reaction was proceeding, the unbound part to the template was induced to form a complete double-stranded DNA by polymerase, and thus this was capable of producing the DNA fragment with a state of linkage of the sequence of 5' end encoding the part of the second soluble extracellular domain and the sequence of 3' end encoding TNFR2 extracellular domain including the leader sequence. Therefore, a part of the sequence of 5' end encoding the second soluble extracellular domain has the function that was capable of binding to the second DNA fragment as follows.

The second DNA fragment was manufactured by PCR using a primer (the sequence of nucleotide of SEQ ID NO: 38) with the sequence encoding the part (the sequence of nucleotide 586–606 of SEQ ID NO: 7) of 3' end of the first soluble extracellular domain of TNFR2 and the part (the sequence of nucleotide 790–807 of SEQ ID NO: 7) of 5' end of the second soluble extracellular domain of TNFR2, and an antisense primer (the sequence of nucleotide of SEQ ID NO: 28) with the sequence encoding a XbaI restriction site and 3' end of IgG1 Fc. This reaction was also performed, that is, only the half of antisense primer was induced to bind the template, and consequently, DNA fragment like that described above had the sequence encoding 5' end of TNFR2 extracellular including the part of 3' end of first soluble extracellular domain.

Subsequently, resulting from two kinds of DNA fragments as PCR produced as above were mixed in the same tube, induced to bind between common sequences, and fused by PCR using primers (the sequence of nucleotide of SEQ ID NO: 29 and 28) encoding 5' and 3' end of each concatameric genes, and the product was designated mgT-NFR2-TNFR2-IgG.

G. Cloning of DNA Constructs Encoding Concatameric Fusion Monomeric Protein of TNFR-TNFR/Fc and Their Glycosylated Forms DNA constructs encoding concatameric fusion monomeric protein of TNFR-TNFR/Fc and their glycosylated forms as above were cloned by inserting into pBluescript KS II (+) (Stratagene, USA) at EcoRI/XbaI site. These produced fusion proteins were designated TNFR1-TNFR1/Fc and TNFR2-TNFR2/Fc as concatameric fusion monomeric protein, and designated mgTNFR1-TNFR1/Fc and mgTNFR2-TNFR2/Fc as their glycosylated forms. The deduced amino acid sequences corresponded to SEQ ID NO: 6, 8, 10, and 12.

After 10 μg of pBluescript KS II (+) (Stratagene, USA) used as a vector was mixed with 15 U of EcoRI, 15 U of XbaI, 5 μl of 10× reaction buffer (100 mM Tris-HCl, pH 7.5, 100 mM MgCl$_2$, 10 mM DTT, 500nM NaCl), 5 μl of 0.1% BSA (Takara, Japan), and 3° distilled water to 50 μl, DNA was restricted by incubation at 37° C. for 2 hrs. After electrophorized on 0.8% agarose gel, the PCR product was purified by Qiaex II gel extraction kit (Qiagen, USA).

After 100 ng of pBluescript KS II (+) (Stratagene, USA) restricted by EcoRI and XbaI was mixed with 20 ng of PCR product restricted by the restriction enzyme, 0.5 U of T4 DNA ligase (Amersham, USA), 1 μl of 10× reaction buffer (300 mM Tris-HCl, pH 7.8, 100 mM MgCl$_2$, 100 mM DTT, 10 mM ATP) and 3° distilled water were added to 10 μl, and the mixture was incubated in the water bath at 16° C. for 16 hrs. E. coli Top10 (Novex, USA) was made to competent cell by the method of rubidium chloride (RbCl, Sigma, USA) and transformed, then spread on the solid LB media including 50 μg/ml of ampicillin (Sigma, USA) and incubated at 37° C. for 16 hrs. Formed colonies were inoculated in 4 ml of liquid LB media including 50 μg/ml of ampicillin and incubated at 37° C. for 16 hrs. Plasmid was purified by the method of alkaline lysis according to Sambrook et al. (Molecular cloning, Cold Spring Harbor Laboratory press, p1.25–1.31, p1.63–1.69, p7.26–7.29, 1989) from 1.5 ml of that, and the existence of cloning was confirmed by the restriction of EcoRI and XbaI.

The sequence of a total coding region was identified by the DNA sequencing method of dideoxy chain termination method (Sanger et al., Proc. Natl. Acad. Sci., 74:5483, 1977) as follows. The DNA sequencing reaction was performed according to the manual using a plasmid purified by alkaline lysis method as described above and Sequenase™ ver 2.0 (Amersham, USA). After the reaction mixture as above was loaded on 6% polyacrylamide gel and electrophorized for 2 hrs at constant voltage of 1,800~2,000 V and 50° C., DNA sequence was identified by exposing to X-ray film (Kodak, USA) after the gel was dried out.

EXAMPLE 2 AND 3

CD2 and CTLA4

DNA fragments encoding soluble extracellular domain of CD2 and CTLA4 were constructed by PCR using a primer [CD2(the sequence of nucleotide of SEQ ID NO: 40), and CTLA4(the sequence of nucleotide of SEQ ID NO: 43)] with EcoRI restriction site and the coding sequence [CD2 (the sequence of nucleotide of SEQ ID NO: 13), and CTLA4 (the sequence of nucleotide of SEQ ID NO: 15)] encoding the leader sequence [CD2(the sequence of amino acid 1–24 of SEQ ID NO: 14), and CTLA4(the sequence of amino acid 1–21 of SEQ ID NO: 16)], and an antisense primer [CD2(the sequence of nucleotide of SEQ ID NO: 41), and CTLA4(the sequence of nucleotide of SEQ ID NO: 44)] with PstI restriction site and the sequence [CD2(the sequence of nucleotide of SEQ ID NO: 13), and CTLA4(the sequence of nucleotide of SEQ ID NO: 15)] encoding 3' end of the soluble extracellular domain of the proteins as described above. The template cDNA for this reaction was constructed by reverse transcription PCR (RT-PCR) of mRNA extracted from the monocyte (T lymphocyte) of healthy adults.

Also, a DNA fragment encoding Fc fragment of immunoglobulin G1 was constructed by PCR using a primer (the sequence of nucleotide of SEQ ID NO: 42) with PstI restriction site and the sequence encoding 5' ends of constant region of IgG1, and an antisense primer (the sequence of nucleotide of SEQ ID NO: 28) with XbaI restriction site and the sequence encoding 3' ends of IgG1 Fc. The template cDNA for this reaction was constructed by RT-PCR of mRNA extracted from peripheral blood cell (B lymphocyte) of convalescent patients with unknown fever.

Subsequently, both DNA fragment encoding soluble extracellular domain of CD2 and CTLA4 and DNA fragment encoding Fc fragment of immunoglobulin G1 produced as described above were restricted by PstI, and then the simple dimeric shape of CD2/Fc and CTLA4/Fc genes were constructed by linkages using T4 DNA ligase. The constructed genes included a leader sequence to faciliate secretion of protein after expression.

DNA constructs as described above were restricted by restriction enzyme of EcoRI and XbaI, and cloned by inserting into a commercially available cloning vector, pBluescript KS II (+) (Stratagene, USA) at EcoRI/XbaI site. The sequence of a total coding region was identified by DNA sequencing (SEQ ID NO: 13 and 15). These produced fusion proteins were designated CD2/Fc and CTLA4/Fc, and the deduced amino acid sequences of these corresponded to SEQ ID NO: 14 and 16.

PCR was performed by adding 1 µl of primary cDNA, 2 U of Pfu DNA polymerase (Stratagene, USA), 10 µl of 10× reaction buffer [200 mM Tris-HCl, pH 8.75, 100 mM (NH$_4$)$_2$SO$_4$, 100 mM KCl, 20 mM MgCl$_2$], 1% Triton™ X-100, 1 mg/ml BSA, 3 µl primer 1 (10 µM), 3 µl primer 2 (10 µM), 2 µl dNTP (10 mM each), and 3° distilled water to 100 µl. The reaction condition was as follows; 94° C., 5 min; 95° C., 1 min; 58° C., 1 min 30 sec; 72° C., 1 min for 31 cycles; and 72° C., 15 min to make PCR product with complete blunt end.

The fusion genes with concatameric shape of CD2-CD2/Fc and CTLA4-CTLA4/Fc were constructed as follows.

In order to manufacture fusion gene comprising the concatameric shape in soluble extracellular domain of CD2 and CTLA4, the sequences of soluble extracellular domain of CD2 and CTLA4 were inserted by blunt-end ligation using ligase at the junction between extracellular domain and immunoglobulin of fusion genes in the shape of simple dimer with blunt end, using PstI restriction enzyme and T4 DNA polymerase. Specifically, DNA constructs were constructed by PCR using a primer [CD2(the sequence of nucleotide of SEQ ID NO: 13) and CTLA4(the sequence of nucleotide of SEQ ID NO: 48)] with the coding sequence [CD2(the sequence of nucleotide of SEQ ID NO: 13) and CTLA4(the sequence of nucleotide of SEQ ID NO: 15)] encoding the end of leader sequence [CD2(the sequence of amino acid 25 of SEQ ID NO: 14) and CTLA4(the sequence of amino acid 22 of SEQ ID NO: 16)] of soluble extracellular domain, and an antisense primer [CD2(SEQ ID NO: 46) and CTLA4(SEQ ID NO: 48)] with the sequence [CD2(the sequence of nucleotide of SEQ ID NO: 13) and CTLA4(the sequence of nucleotide of SEQ ID NO: 15)] encoding 3' end of soluble extracellular domain as above. The simple fusion monomeric genes [CD2/Fc (the sequence of nucleotide of SEQ ID NO: 13) and CTLA4/Fc (the sequence of nucleotide of SEQ ID NO: 15)] described as above were used as the template of this reaction.

Also, CD2/Fc and CTLA4/Fc, which were inserted in pBluescript KS II (+) in the shape of simple monomeric form, were made to have 3' overhang end using the restriction enzyme of PstI. The cut end of 3' overhang was partially deleted to form a blunt end by treating T4 DNA polymerase. In order to manufacture fusion genes in the shape of concatamer in soluble extracellular domain, the soluble extracellular domains of CD2 and CTLA4 produced by PCR as described above were cloned by inserting into cut ends of simple monomeric gene made as blunt end. These produced fusion proteins were designated CD2-CD2/Fc and CTLA4-CTLA4/Fc as concatameric fusion monomeric protein, and their deduced amino acid sequences corresponded SEQ ID NO: 18 and 20, respectively.

The concatameric fusion genes in the shape of multiglycosylated form were constructed as follows.

The glycosylation mofit was inserted by secondary PCR with mixing in the same tube of a DNA fragment produced by PCR using a primer including EcoRI restriction site and the soluble extracellular domain with leader sequence, and an antisense primer with the sequence encoding the part of 3' end of the first soluble extracellular domain of concatameric shape of fusion gene and the part of 5' end of the second soluble extracellular domain with the nucleotide of substituted glycosylation motif; and other DNA fragment produced by PCR using a primer with the sequence encoding the part of 3' end of the first soluble extracellular domain of concatameric shape of fusion gene and the part of 5' end of the second soluble extracellular domain with the nucleotide of substituted glycosylation motif, and an antisense primer with the sequence encoding 3' end of Fc fragment of immunoglobulin G1 and XbaI restriction site.

In the case of concatameric fusion gene of CD2/Fc and CTLA4/Fc, the glycosylation motif was inserted by PCR using modified primers as the same methods as that of TNFR/Fc described as above, but it was different from the case of TNFR/Fc that the amino acid sequence of binding to soluble extracellular domain of CD2 and CTLA4 was retained as the same.

In the process of multiglycosylatin of the concatameric fusion protein of CD2/Fc and CTLA4/Fc, the case of CD2/Fc was completed by inserting the total two glycosylation motif peptide region (the sequence of amino acid of 200–202 and 206–208 of SEQ ID NO: 22) using a manufactured primer including the substitution of the nucleotide of 598–600 (CCT, Pro) and 616–618 (GAG, Glu) of SEQ ID NO: 17 with AAT (Asn, N), and the case of CTLA4/Fc was completed by inserting the total three glycosylation motif peptide region (the sequence of amino acid of 136–138, 142–144, and 147–149 of SEQ ID NO: 24) using a manufactured primer(SEQ ID NO: 51 and 52) including the substitution of the nucleotide of 403–405 (GTA, Val) and 424–426 (CCA, Pro) of SEQ ID NO: 19 with AAT (Asn, N); the nucleotide of 409–411 (GAT, Asp) and 445–447 (GTG, Val) with ACA (Thr, T) and ACG (Thr, T), respectively. These produced fusion proteins were designated mgCD2-CD2/Fc and mgCTLA4-CTLA4/Fc as concatameric fusion monomeric protein, and their deduced amino acid sequences corresponded to SEQ ID NO: 22 and 24, respectively.

EXAMPLE 4

Expression and Purification of Simple/Concatameric Fusion Dimeric Protein of TNFR/Fc In order to express the fusion proteins in CHO-K1 cell (ATCC CCL-61, Ovary, Chinese hamster, *Cricetulus griseus*), after pBluescript KS II (+) plasmid DNA including TNFR/Fc fusion gene was purified from transformed *E. coli*, an animal cell expression vectors were constructed as TNFR/Fc fragment produced by restriction using EcoRI and XbaI was inserted at EcoRI/XbaI site of an animal cell expression vector, pCR™3 (Invitrogen, USA) plasmid. And these were designated plasmid pTR11-Top10' and plasmid pTR22-Top10', and deposited as accession numbers of KCCM 10288 and KCCM 10291, respectively, at Korean Culture Center of Microorganisms (KCCM) on Jul. 10. 2001.

Transfection was performed by mixing either the plasmid pTR11-Top10' or plasmid pTR22-Top10' DNA including TNFR/Fc fusion genes as described above with the reagent of Lipofectamin™ (Gibco BRL, USA). CHO-K1 cells with the concentration of 1~3×10$^5$ cells/well were inoculated in 6-well tissue culture plate (Nunc, USA), and incubated to 50~80% in 10% FBS-DMEM media, then the DNA-liposome complex, which was reacted for 15~45 min with 1~2 μg of either the plasmid pTR11-Top10' or plasmid pTR22-Top10' DNA including TNFR/Fc fusion genes as described above and 2~25 μl of Lipofectamin™ (Gibco BRL, USA), were added to the cell culture plate in the serum-free DMEM media. After incubation for 5 hrs, DMEM media with 20% serum was added and cells were incubated further for 18~24 hrs. After primary transfection, cells were incubated for 3 weeks in 10% FBS-DMEM media with 1.5 mg/ml of Geneticin (G418, Gibco BRL, USA), and formed colonies was selected for amplified incubation. The expression of fusion proteins was analyzed by ELISA using a peroxidase labeled goat anti-human IgG (KPL, USA).

ELISA was performed as follows. First, 1 mg/ml of a peroxidase labeled goat anti-human IgG (KPL, USA) was diluted to 1:2,000 with 0.1M sodium bicarbonate, 100 μl of that was aliquoted into 96-well flexible plate (Falcon, USA) and sealed with plastic wrap, then incubated at 4° C. over 16 hrs to be coated on the surface of the plate. After this, it was washed for 3 times with washing buffer (0.1% Tween-20 in 1×PBS) and dilution buffer (48.5 ml 1XPBS, 1.5 ml FBS, 50 ul Tween-20), and then was aliquoted to 180 l. After 20 μl of culture supernatant was dropped in the first well, then serially diluted using a micropipette, and 0.01 μg/μl of human immunoglobulin G (Sigma, USA) as the positive control and the culture media of untransfected CHO K-1 cell as the negative was equally diluted. After dilution, 96-well ELISA plate (Falcon, USA) was wrapped with aluminum foil and incubated at 37° C. for 1 hr 30 min, washed for 3 times with washing buffer. Peroxidase conjugated goat anti-human IgG (KPL, USA) was diluted to 1:5,000 with dilution buffer, aliquoted to 100 μl, wrapped with aluminum foil, and reacted at 37° C. for 1 hr. After reaction, this plate was washed for 3 times, colorized using TMB microwell peroxidase substrate system (KPL, USA) and existence of expression was confirmed by measurement of absorbance at 655 nm wavelength using microplate reader (Bio-Rad, Model 550, Japan).

Transfectants manufactured as above were designated TR 11 Ig-CHO and TR22Ig-CHO and deposited as accession numbers of KCLRF-BP-00046 and KCLRF-BP-00047, respectively, at Korean Cell Line Research Foundation (KCLRF) on Jul. 7, 2001. And adaptation for transfectants as described above to one of the serum free media, CHO-S-SFM II (Gibco BRL, USA), was proceeded to purify the proteins produced by those transfectants as follows. After about 3×10$^5$ of cells were inoculated into the 6-well plate, cells were cultured at 5% CO2, 37° C. for over 16 hrs to adhere, and it was checked under a microscope that cells were adhered at about 30~50% area of the plate, then cells were cultured in a media consisting of 10% FBS DMEM and CHO-S-SFM II in the ratio of 8:2. After culturing 3 times serial passage at this ratio, it was cultured 3 times at the ratio of 6:4; 3 times at 4:6; 3 times at 3:7; 3 times at 2:8, 3 times at 1:9; and finally cultured in 100% CHO-S-SFM II media. And the level of expression was measured by ELISA.

After these transfectant cells were cultured on a large scale in CHO-S-SFM II, the supernatants including each fusion proteins were centrifuged at 200×g for 12 min to remove cell debris, and proteins were purified by the method using HiTrap protein A column (Amersham, USA) as follows. After 20 mM of sodium phosphate (pH 7.0, Sigma, USA) was passed at the velocity of 1 ml/min for 2 min, 10 ml of supernatant was passed at the same velocity to bind fusion protein to protein A. After 20 mM of sodium phosphate (pH 7.0) was passed at the same velocity for 2 min to wash, 500 μl of the extracts were serially fractionated in a 1.5 ml tube as 0.1M of citric acid (pH 3.0, Sigma, USA) was passed at the the same velocity for 3 min. This was adjusted to pH 7.0 using 1M of Tris (pH 11.0, USB, USA), the existence of fusion proteins in tube was confirmed through ELISA as described above. The purified proteins were concentrated by centrifugation at 2000×g, 4° C. for 30 min using Centricon 30 (Amicon, USA)

EXAMPLE 5

Figure 15:
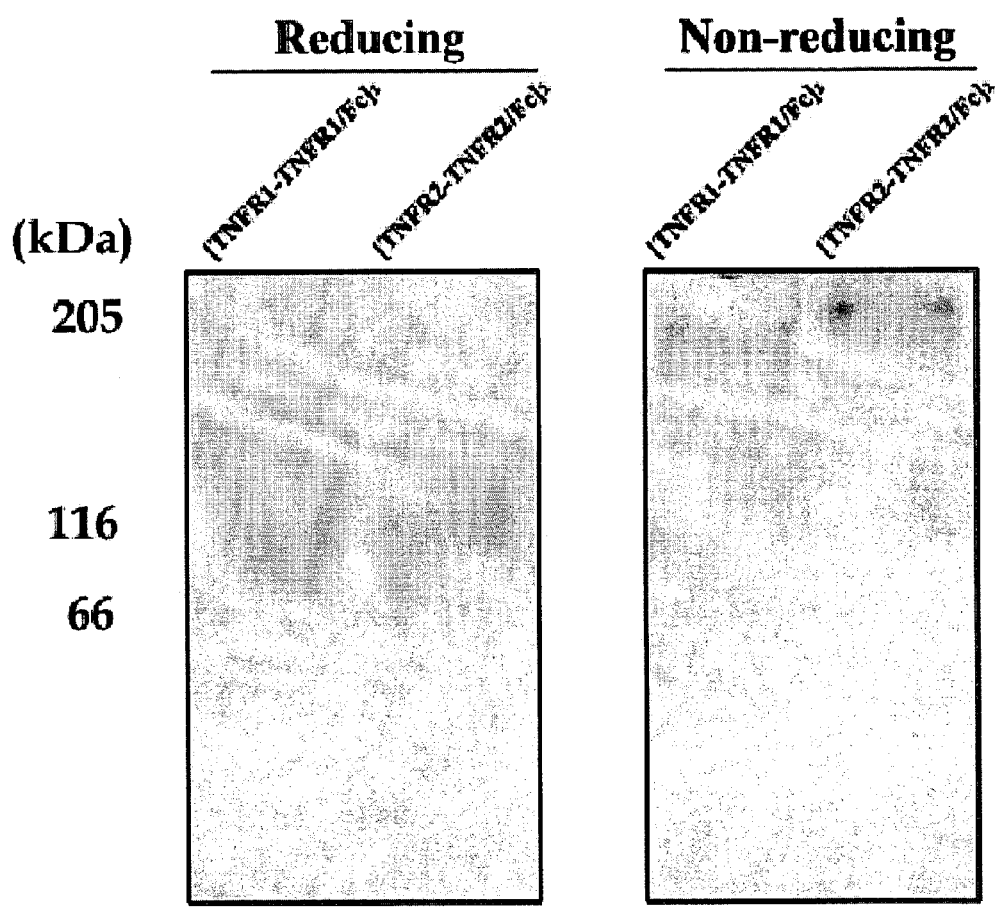
FIG. 15 shows a result of SDS-PAGE of purified concatameric fusion dimeric proteins [TNFR1-TNFR1/Fc]$_2$ and [TNFR2-TNFR2/Fc]$_2$ under reducing or non-reducing conditions.

SDS-PAGE of Purified TNFR1-TNFR1/Fc and TNFR2-TNFR2/Fc (FIG. 15)

Proteins purified using protein A column were electrophorized by the method of SDS-PAGE in reducing condition added by DTT, reducing reagent (which destroy disulfide bond), and in a non-reducing condition excluding DTT. The result of the estimation of molecular weight on SDS-PAGE is shown in Table 10. It was possible to confirm that TNFR/Fc proteins were the shape of a dimer in the cell. The molecular weight deduced from the amino acid sequence of TNFR1-TNFR1-Ig was about 70 kDa, and was estimated as about 102 kDa on SDS-PAGE. As this difference could be regarded as a general phenomenon which generate on the electrophoresis of glycoproteins, this feature seemed to occurr as the result from decrease in mobility on the electrophoresis by the site of glycosylation.

TABLE 10

Molecular weight of TNFR-TNFR/Fc on the SDS-PAGE.

| Proteins | Molecular weight (kDa) | |
|---|---|---|
| | Reducing condition | Non-reducing condition |
| TNFR1-TNFR1/Fc | 102 | 200 |
| TNFR2-TNFR2/Fc | 115 | 220 |

EXAMPLE 6

Experiment of Neutralization Effect of Simple/Concatameric Fusion Dimeric TNFR/Fc Fusion Proteins on the Cytotoxicity of TNFα and TNFβ

An L929 cell [ATCC, Mus musculus (mouse), NCTC clone 929 (derivative of strain L; L-929; L cell) was used for testing the effect of TNFR/Fc fusion protein on the inhibition of cytotoxicity induced by TNFα and TNFβ. This analysis was based on the TNFR activity of inhibiting cytotoxicity induced by TNF (Scallon et al., Cytokine 7:759, 1995).

L929 cells were inoculated to be $3 \times 10^4$ cells/well in 96-well plates, and incubated at 37° C. for 24 hrs in a $CO_2$ incubator. Subsequently, actinomycin D (Sigma, USA) was added to 3 μg/ml, and cells were incubated for 16~18 hrs with TNFα and TNFβ in the concentration of expressing 100% cytotoxicity (0.5~2 ng/ml), and with serially 10 times diluted TNFR sample. Then, the cells in the 96-well plate were stained by the staining reagent, crystal violet (Wako Pure Chemical Industries, Japan) and the activity of the cells was estimated by the degree of absorbance at 595 nm wavelength using a spectrophotometer (Bio-Rad, Model-550, Japan).

Figure 16:
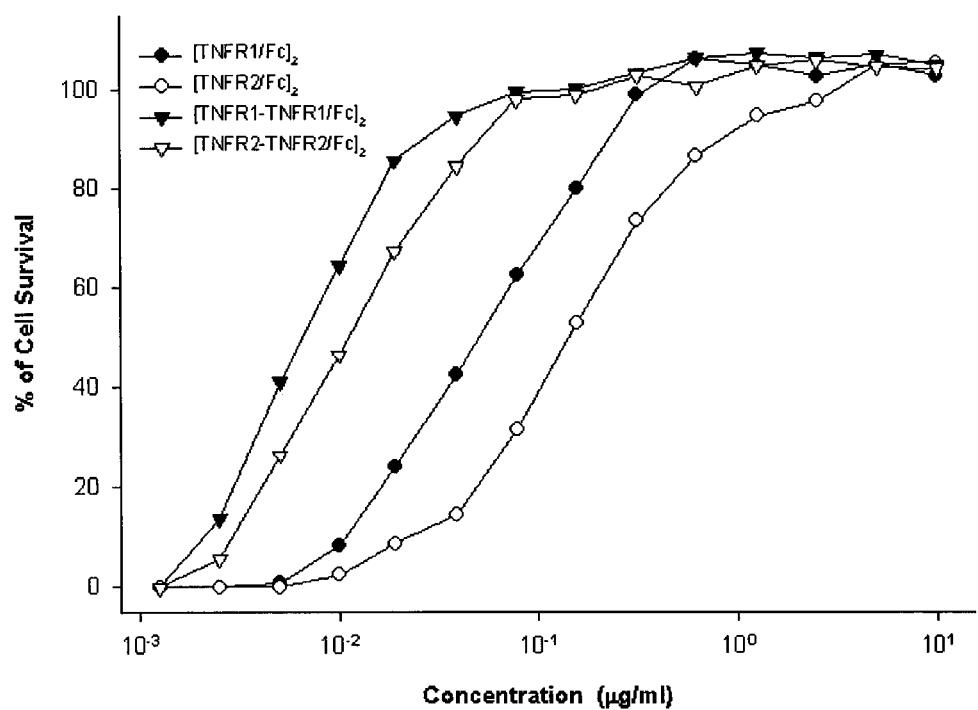
FIG. 16 is a graph showing inhibitory effect of the conventional simple fusion dimeric proteins [TNFR1/Fc]$_2$ (●) and [TNFR2/Fc]$_2$(○) and the concatameric fusion dimeric proteins [TNFR1-RNFR1/Fc]$_2$(▼) and [TNFR2-TR2Fc]$_2$(∇) according to the present invention against cytotoxic activity of TNF-alpha.
Figure 17:
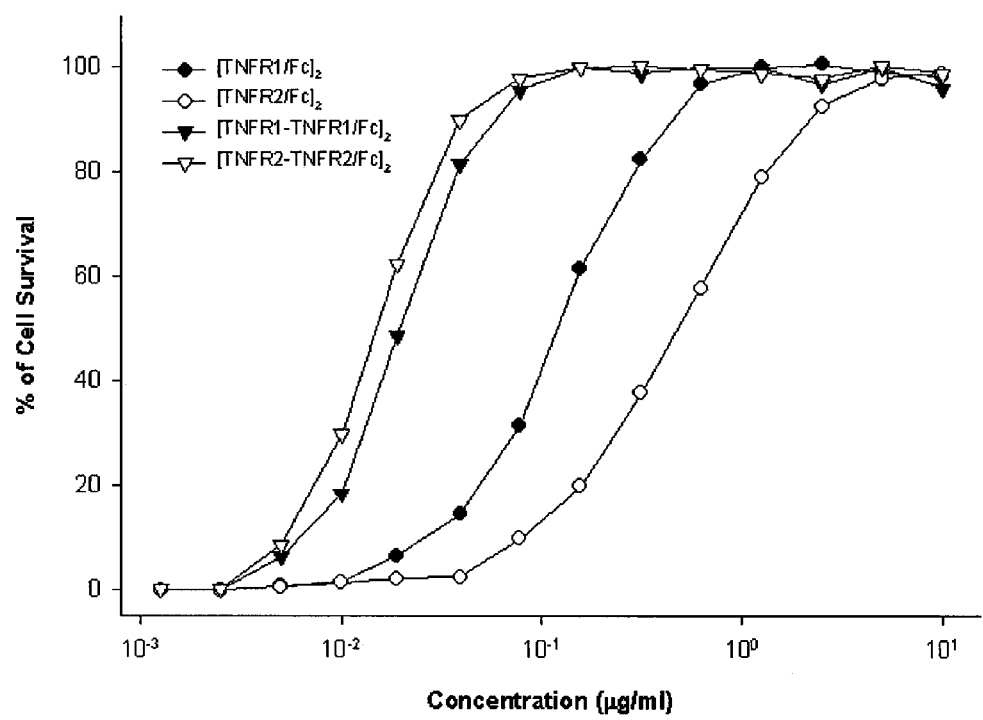
FIG. 17 is a graph showing inhibitory effect of the conventional simple fusion dimeric proteins [TNFR1/Fc]$_2$ (●) and [TNFR2/Fc]$_2$(○) and the concatameric fusion dimeric proteins [TNFR1-RNFR1/Fc]$_2$(▼) and [TNFR2-TR2Fc]$_2$(∇) according to the present invention against cytotoxic activity of TNF-beta.
Figure 18:
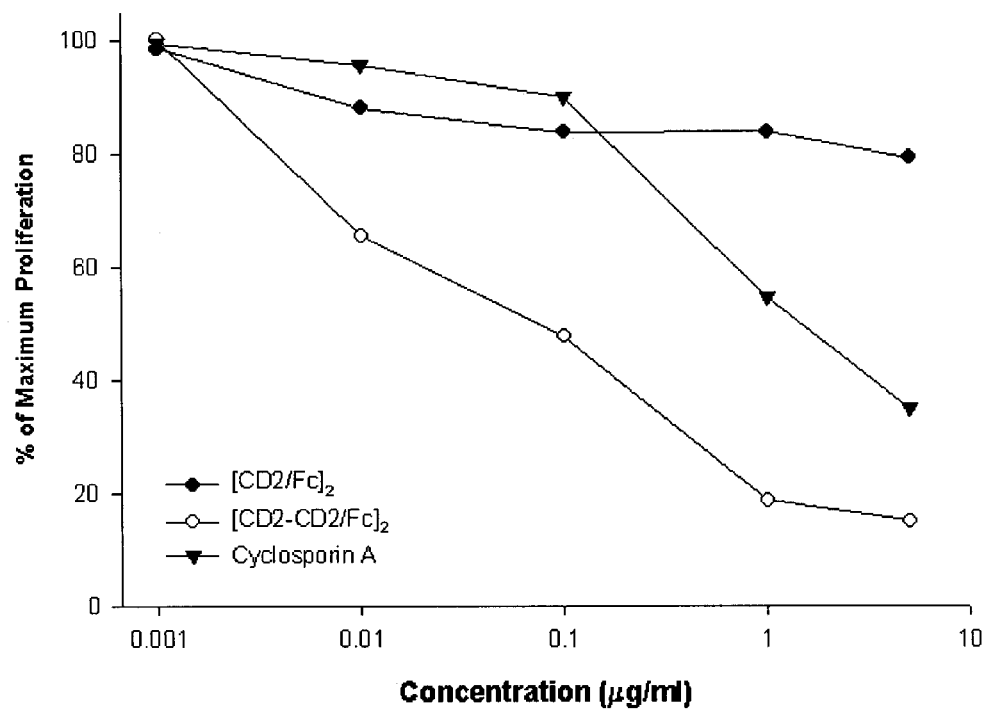
FIG. 18 is a graph showing inhibitory effect of the conventional simple fusion dimeric protein [CD2/Fc]$_2$(●), the known immunosuppressive agent cyclosporin A (▼) and the concatameric fusion dimeric protein [CD2-CD2/Fc]$_2$ (○) according to the present invention on the proliferation of active T lymphocytes.
Figure 19:
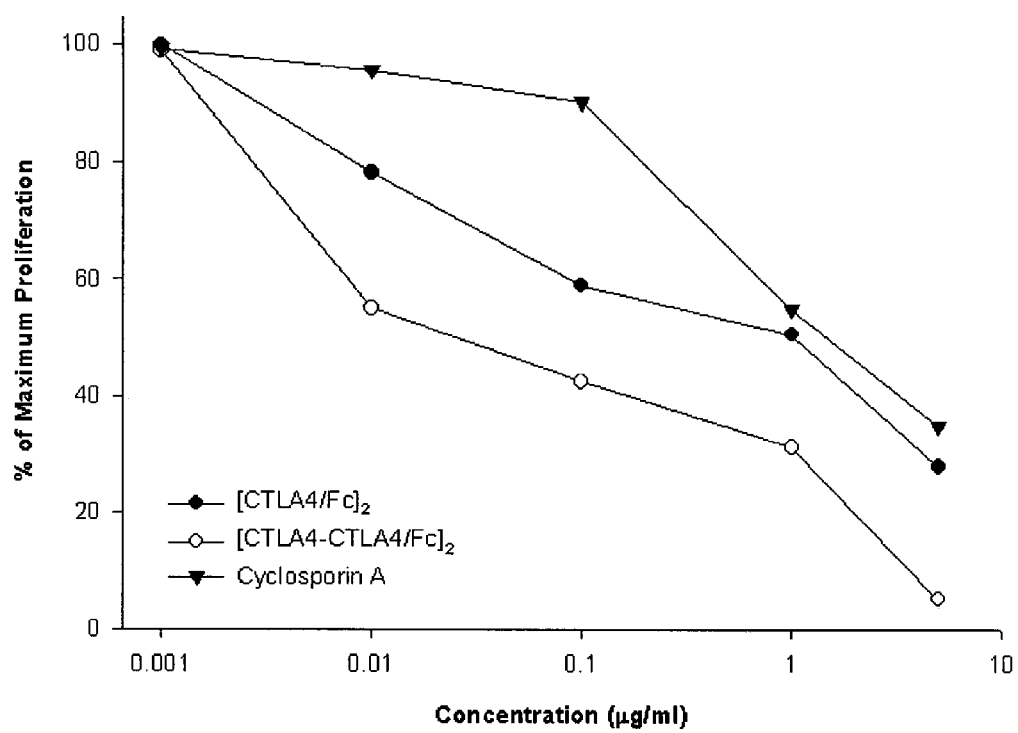
FIG. 19 is a graph showing inhibitory effect of the conventional simple fusion dimeric protein [CTLA4/Fc]$_2$ (●), the known immunosuppressive agent cyclosporin A (▼) and the concatameric fusion dimeric protein [CTLA4-CTLA4/Fc]$_2$ (○) according to the present invention on the proliferation of active T lymphocytes.

As shown in Table 11 represented by $IC_{50}$ of each TNFR/Fc fusion protein, concatameric fusion proteins (TNFR1-TNFR1/Ig and TNFR2-TNFR2/Ig) have shown the higher inhibitory effect on the cytotoxicity induced by two kinds of TNF than simple dimeric fusion proteins (TNFR1/Ig and TNFR2/Ig). Also, as compared with the effects of existing simple fusion dimer and concatameric shaped TNFR/Fc fusion protein dimer of the present invention on the inhibition of cytotoxicity of TNFα(FIG. 16) and TNFβ (FIG. 17), it more clearly appeared that concatameric shaped TNFR/Fc fusion protein dimers of the present invention remarkably inhibited the TNFα and TNFβ cytotoxicity.

TABLE 11

| | | $IC_{50}$ of cytotoxicity inhibition | |
|---|---|---|---|
| | | $IC_{50}$ (ug/ml) | |
| Fusion proteins | | TNFα treated | TNFβ treated |
| Simple dimer | [TNFR1/Fc]$_2$ | 63 | 129 |
| | [TNFR2/Fc]$_2$ | 189 | 469 |
| Concatameric dimer | [TNFR1-TNFR1/Fc]$_2$ | 9 | 20 |
| | [TNFR2-TNFR2/Fc]$_2$ | 15 | 15 |

EXAMPLE 7

Experiment of Suppressive Effect of Simple/Concatameric Fusion Dimeric CD2/Fc Fusion Protein and CTLA4/Fc Fusion Protein on the Proliferation of Active Immune Cell WT100B1S, a cell line of B lymphocyte which was made by transfection of pyrexia patient's B lymphocyte with Ebstein-Barr virus was incubated in RPMI 1640 supplemented with 10% FBS to use as antigen presenting cell of T lymphocyte. After centrifuged at 2,000 rpm for 2 min to precipitate, this cells were resuspended in RPMI 1640 supplemented with 10% FBS to make $5.0 \times 10^5$ cells/ml, then irradiated by 3,000 rd of γ-ray.

T lymphocytes were isolated from blood of healthy adult using Ficoll-hypaque (Amersham, USA), then incubated RPMI 1640 supplemented with 10% FBS to $2.0 \times 10^6$ cells/ml.

To perform primary Mixed Lymphocyte Reaction (MLR), each 15 ml of WT100B1S and T lymphocyte were mixed in 150 mm cell culture dish, and incubated for 3 days, then added by 15 ml of RPMI 1640 supplemented with 10% FBS and incubated for 3 days further. After incubated for total 6 days, live T lymphocytes were purified using Ficoll-hypaque (Amersham, USA) as described above, and purified T lymphocytes were stored in liquid nitrogen after freezing it by using the media comprising 45% FBS, 45% RPMI 1640, and 10% DMSO.

After T lymphocytes which were reacted by primary MLR were thawed to perform secondary MLR, the cells were washed with RPMI 1640 media for 2 times and made to be $3.0 \times 10^5$ cells/ml in RPMI 1640 supplemented with 10% FBS.

WT100B1S using as antigen presenting cell was newly cultured by the method as described above, then prepared by irradiation of 3,000 rd of γ-ray and to be $7.5 \times 10^4$ cells/ml in RPMI 1640 supplemented with 10% FBS. After 100 μl of prepared WT100B1S was added in 96-well flat bottom cell culture plate and mixed with CD2/Fc and CTLA4/Fc fusion protein at final concentration of 10, 1, $10^{-1}$, $10^{-2}$, $10^{-3}$, and $10^{-4}$ μg/ml, 100 μl of primary MLR reacted T lymphocytes as above was added. After incubated for 2 days in 5% $CO_2$, 37° C. incubator, 100 μl of RPMI 1640 supplemented with 10% FBS was added and incubated for 2 days further. In the last 6 hrs of the total 6 days culture, cells were incubated with addition of 1.2 μCi/ml of $^3$H-thymidine (Amersham, USA).

At the end of culturing, supernatants were removed after centriftigation of 96-well plate was performed at 4° C., 110×g for 10 min to precipitate T lymphocytes, and pellets were washed with 200 μl of 1× PBS. Centrifugation was performed in the same condition and PBS was removed, then 200 μl of ice-cold trichloridic acid (TCA, Merck, USA) was added and mixed for 2 min, then reacted at 4° C. for 5 min to remove residue of $^3$H-thymidine.

After centrifugation in the same condition as described above, supernatants were removed and T lymphocytes were fixed by incubation at 4° C. for 5 min after 200 μl of ice-cold 70% ethanol was added. Supernatants were removed after centrifugation, and $^3$H-thymidine (Amersham, USA) residue was completely removed by treatment of 10% TCA in the same method as described above.

Cell lysis was performed by reaction with 100 μl of 2% SDS (pH 8.0) and 0.5N of NaOH at 37° C. for 30 min, and T lymphocytes were precipitated by centrifugation at 25° C., 110×g for 10 min, and then 50 μl of supernatants was transferred to 96-well sample plate (Wallac, USA). After 1.5 volume of OptiPhase SuperMix (Wallac, USA) was added into the supernatants and mixed for 5 min, the existence of T lymphocyte proliferation was confirmed by measurement of cpm value of $^3$H using 1450 MicroBeta TriLux microplate liquid scintillation and luminescence counter (Wallac, USA).

EXAMPLE 8

Figure 20:
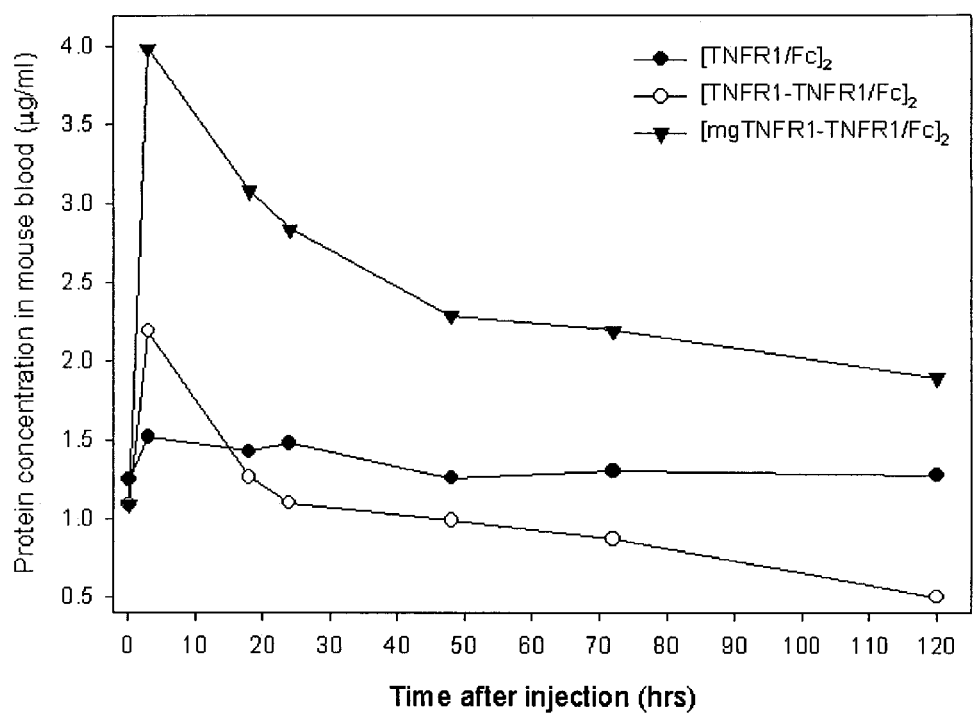
FIG. 20 is a graph showing blood half-life of the conventional simple fusion dimeric protein [TNFR1/Fc]$_2$(●), the concatameric dimeric protein [TNFR1-TNFR1/Fc]$_2$ (○) and a glycosylated concatameric fusion dimeric protein [mgTNFR1-TNFR1/Fc]$_2$ (▽) according to the present invention.
Figure 21:
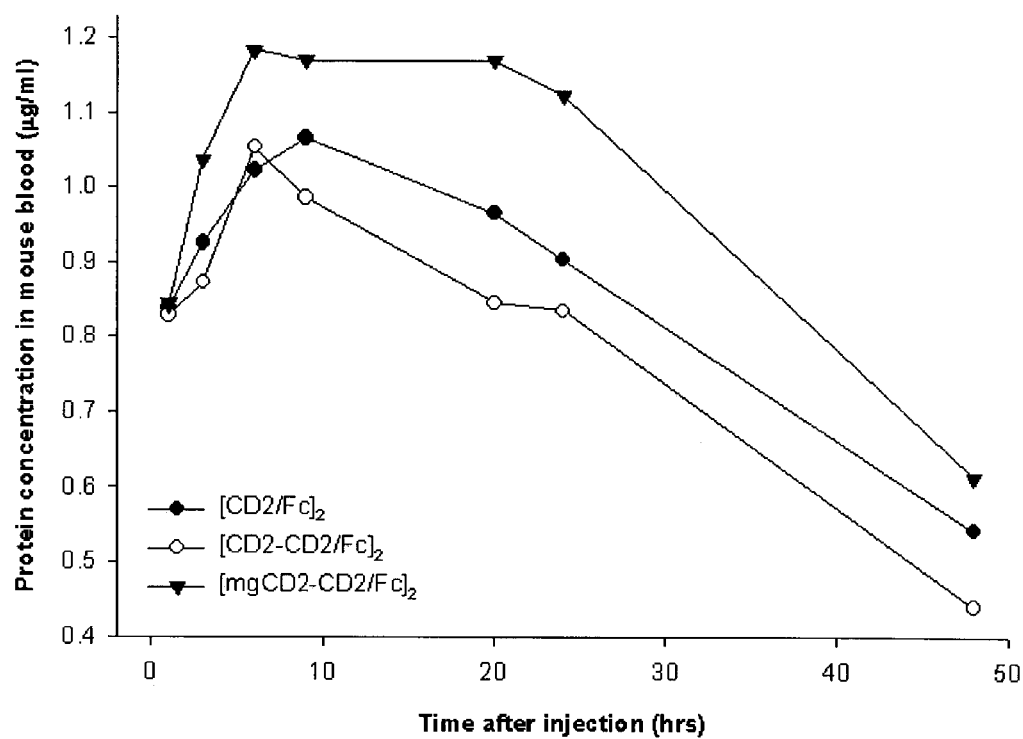
FIG. 21 is a graph showing blood half-life of the conventional simple fusion dimeric protein [CD2/Fc]$_2$(●), the concatameric fusion dimeric protein [CD2-CD2/Fc]$_2$ (○) and a glycosylated concatameric fusion dimeric protein [mgCD2-CD2/Fc]$_2$ (▽) according to the present invention.
Figure 22:
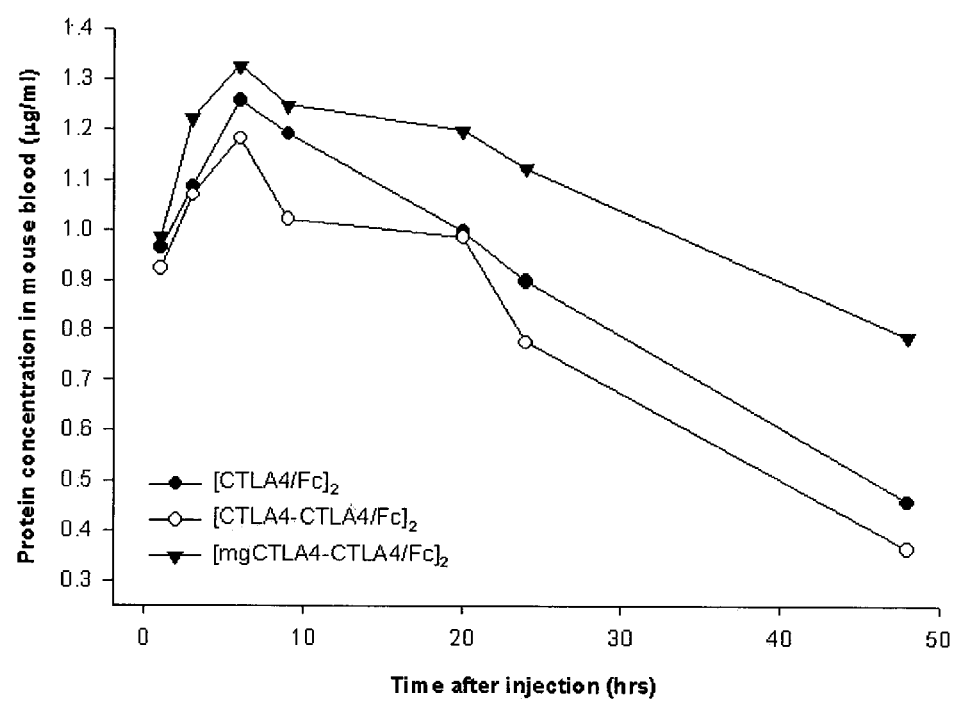
FIG. 22 is a graph showing blood half-life of the conventional simple fusion dimeric protein [CTLA4/Fc]$_2$(●), the concatameric fusion dimeric protein [CTLA4-CTLA4/Fc]$_2$ (○) and a glycosylated concatameric fusion dimeric protein [mgCTLA4-CTLA4/Fc]$_2$ (▽) according to the present invention.

Experiment of Effect on Increase of Plasma Half-Life of Glycosylated Concatameric Fusion Dimeric Proteins in Mouse The measurement of plasma half-life of glycosylated concatameric fusion dimeric proteins, [mgTNFR1-TNFR1/Fc]2, [mgTNFR2-TNFR2/Fc]2, [mgCD2-CD2/Fc]2, and [mgCTLA4-CTLA4/Fc]2 was performed by measuring the concentration of proteins using ELISA after 5 µg of purified fusion proteins was i.p. injected into mouse (ICR, Samtako, Korea) and bloods were extracted at regular interval for 120 hrs (5 days) as maximum. As shown FIG. 20, FIG. 21, and FIG. 22, it could be seen that the plasma half-life of glycosylated concatameric fusion dimeric proteins have been increased in comparison of the corresponding simple fusion dimeric proteins of native shape, and the increase in efficacy through continuous effect could be expected.

EXAMPLE 9

Experiment of Effects of Simple/Concatameric TNFR/Fc Fusion Protein Dimers on Collagen-Induced Arthritis of DBA/1 Mouse Collagen Induced Arthritis (CIA) was developed by injection with 100 µg per DBA/1 mouse of type II collagen dissolved at 2 mg/ml concentration in 0.05M acetic acid and Arthrogen-CIA adjuvant (Chondrex, USA) into tail. Boosting was performed after 3 weeks, and incomplete Freund's adjuvant (Difco, USA) was used.

Figure 7:
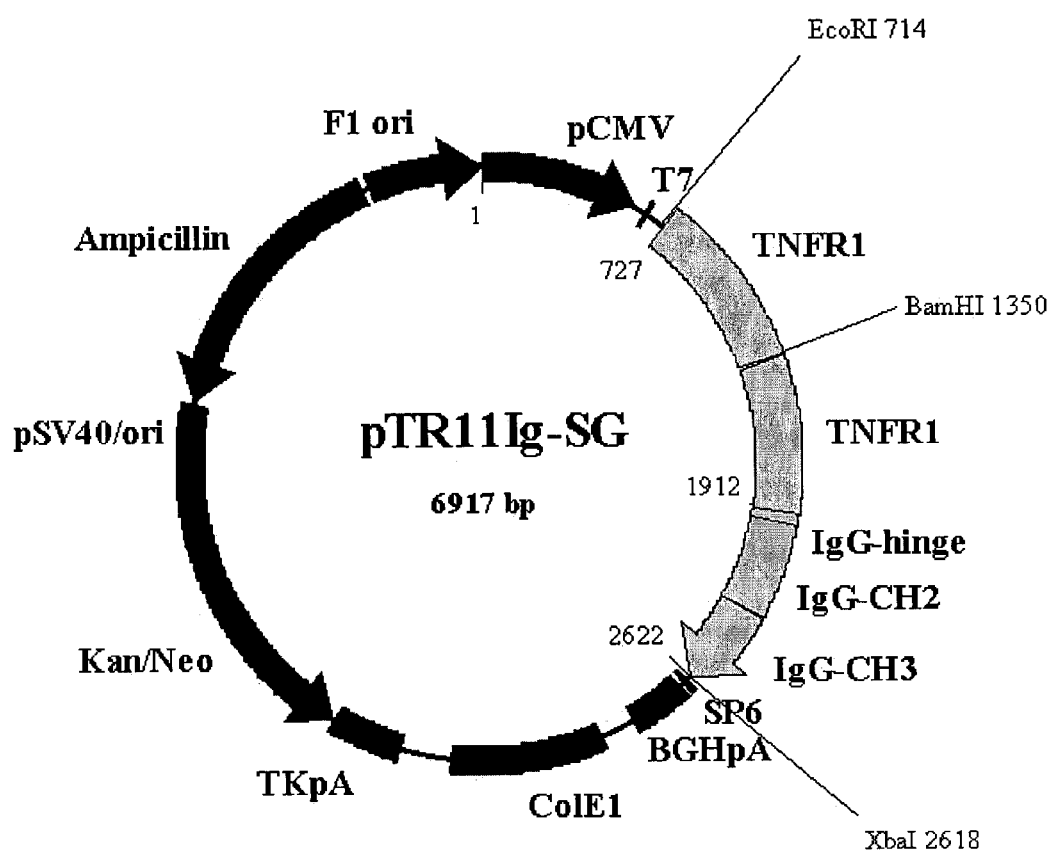
FIG. 7 is a map of a recombinant expression plasmid pTR11Ig-Top10' expressing a concatameric fusion monomeric protein TNFR1-TNFR1/Fc according to the present invention.
Figure 8:
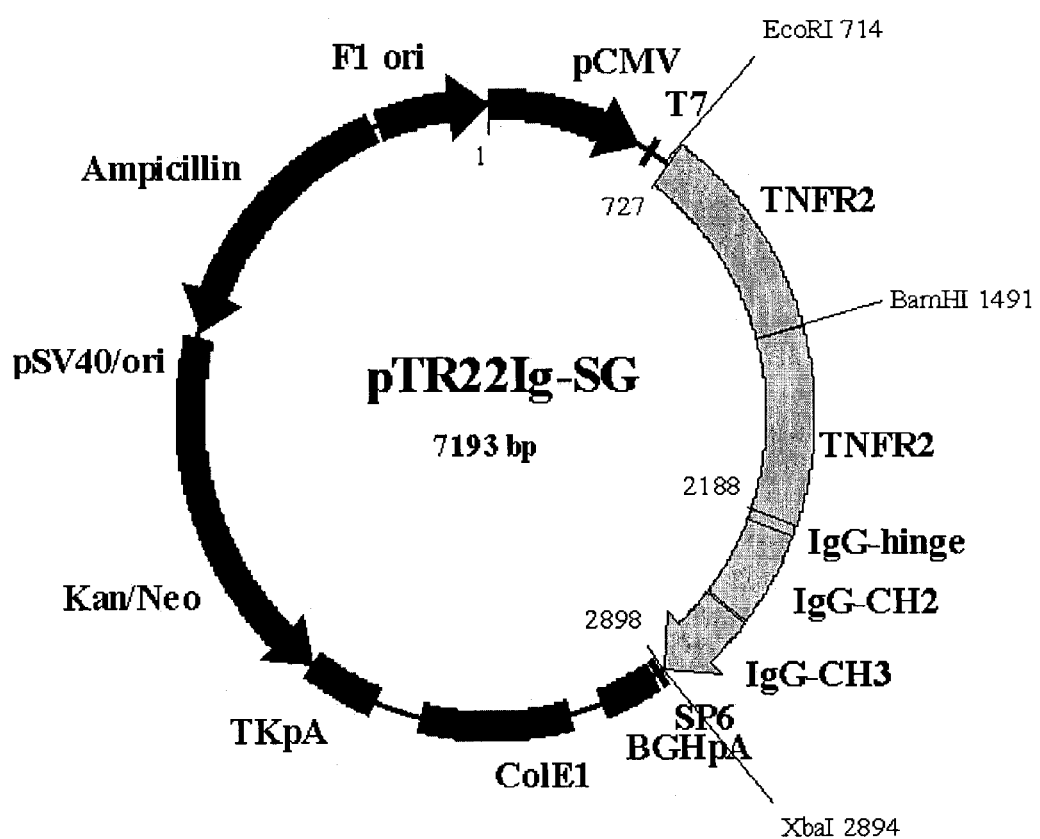
FIG. 8 is a map of a recombinant expression plasmid pTR22Ig-Top10' expressing a concatameric fusion monomeric protein TNFR1-TNFR1/Fc according to the present invention.
Figure 9:
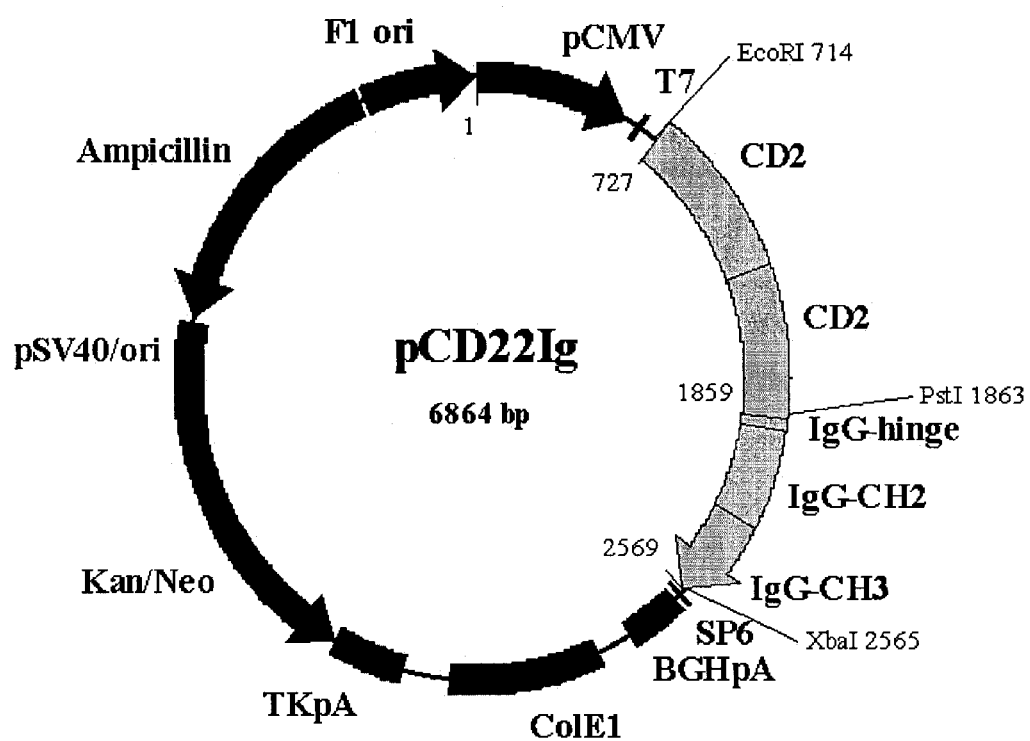
FIG. 9 is a map of a recombinant expression plasmid pCD22Ig expressing a concatameric fusion monomeric protein CD2-CD2/Fc according to the present invention.
Figure 10:
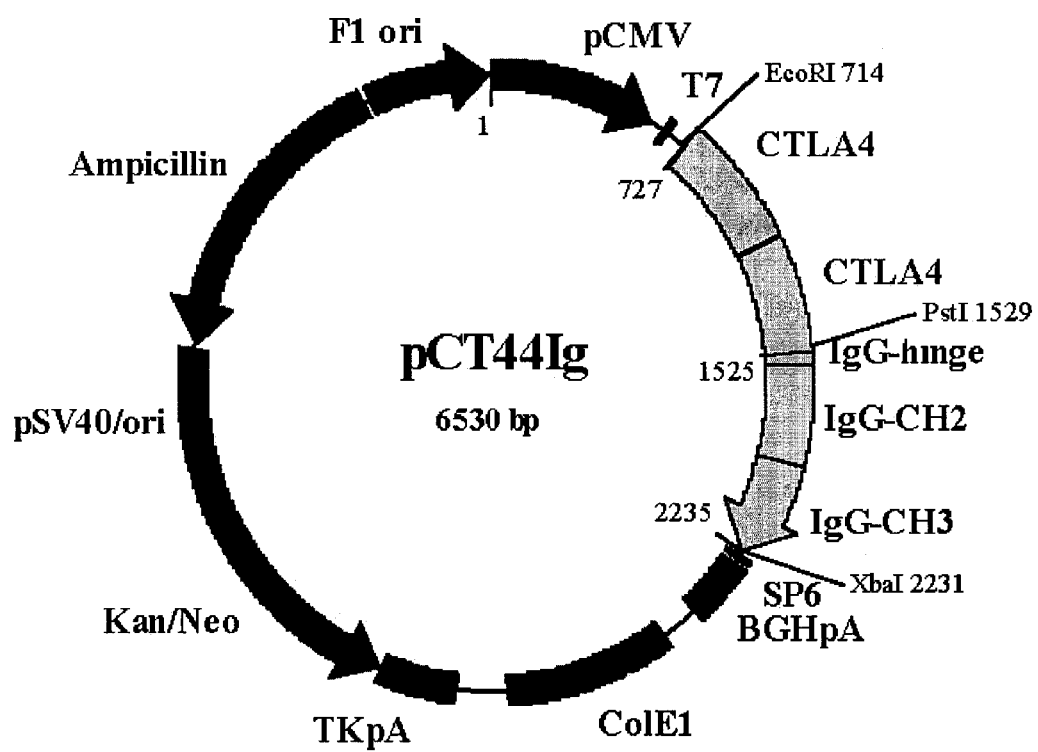
FIG. 10 is a map of a recombinant expression plasmid pCT44Ig expressing a concatameric fusion monomeric protein CTLA4-CTLA4/Fc according to the present invention.
Figure 11:
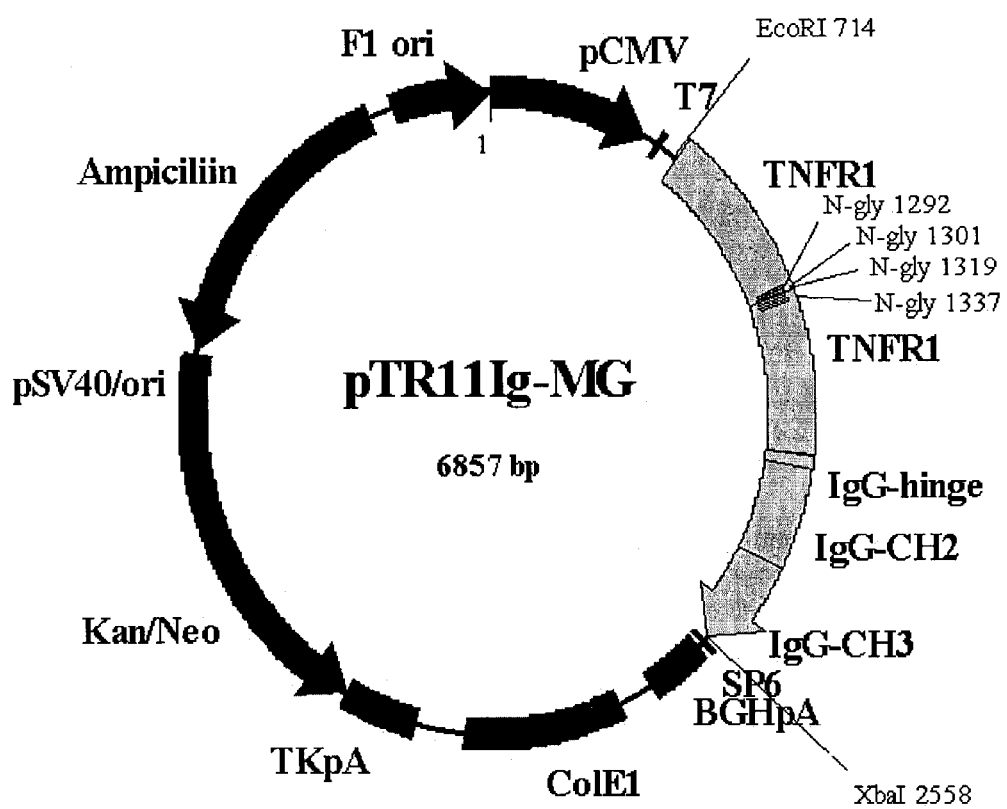
FIG. 11 is a map of a recombinant expression plasmid pTR11Ig-MG expressing a concatameric fusion monomeric protein mgTNFR1-TNFR1/Fc containing four glycosylation motif peptides according to the present invention.
Figure 12:
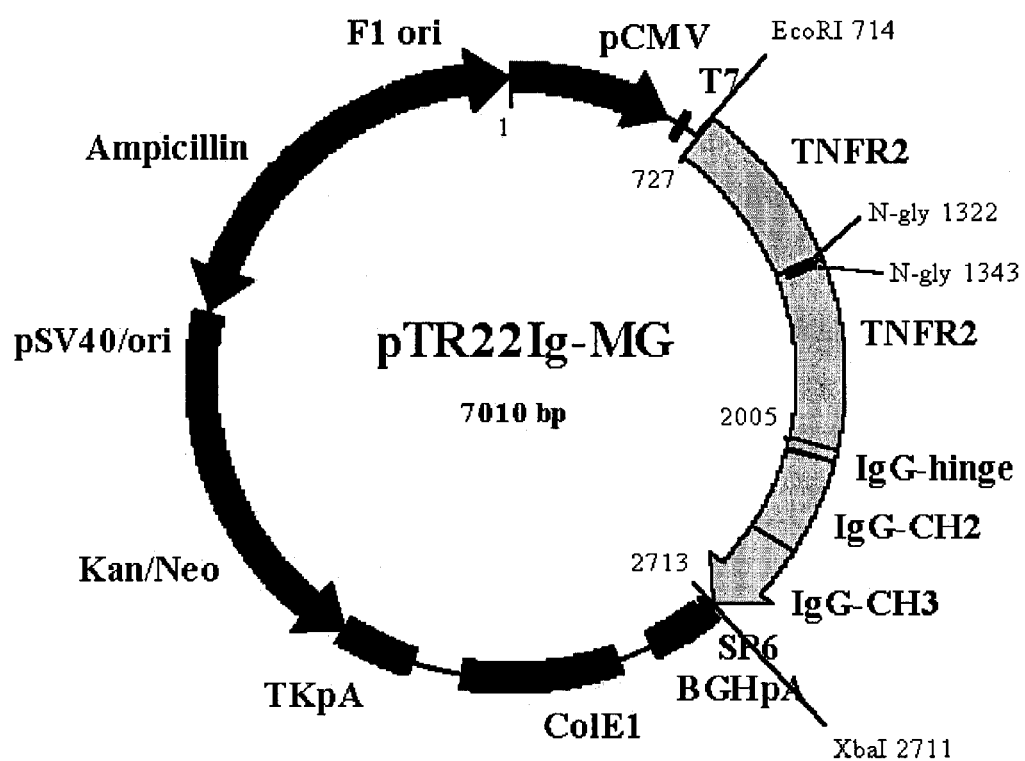
FIG. 12 is a map of a recombinant expression plasmid pTR22Ig-MG expressing a concatameric fusion monomeric protein mgTNFR2-TNFR2/Fc containing two glycosylation motif peptides according to the present invention.
Figure 13:
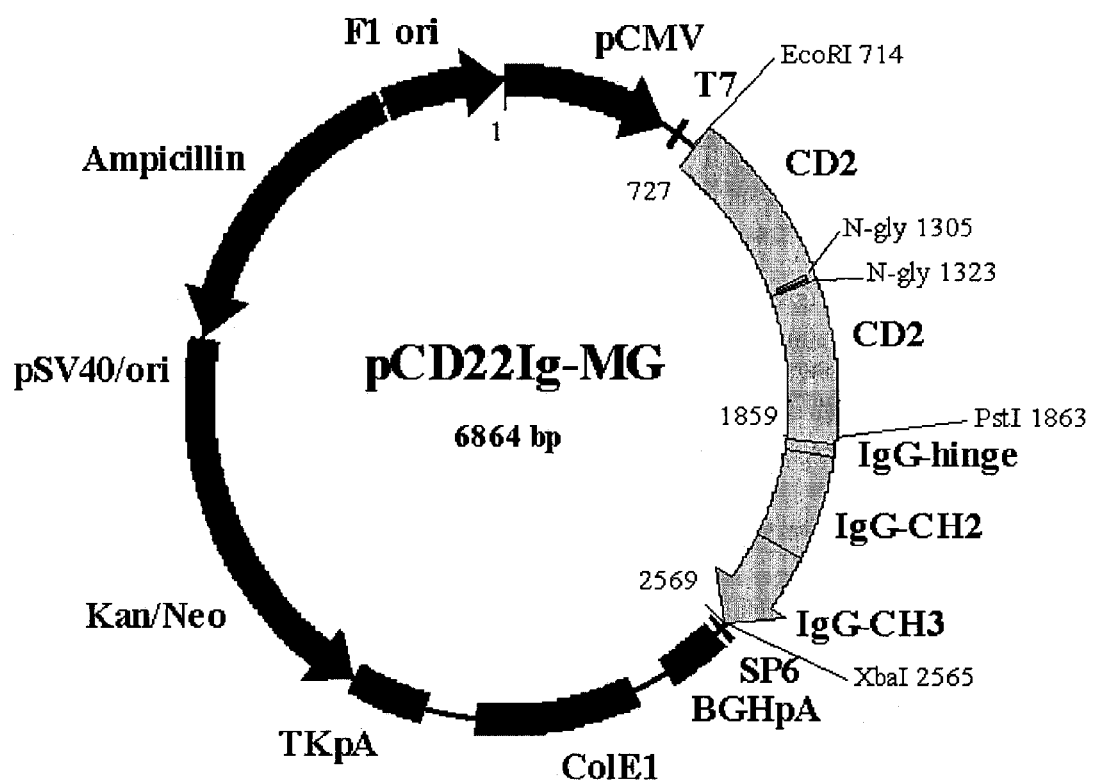
FIG. 13 is a map of a recombinant expression plasmid pCD22Ig-MG expressing a concatameric fusion monomeric protein mgCD2-CD2/Fc containing two glycosylation motif peptides according to the present invention.
Figure 14:
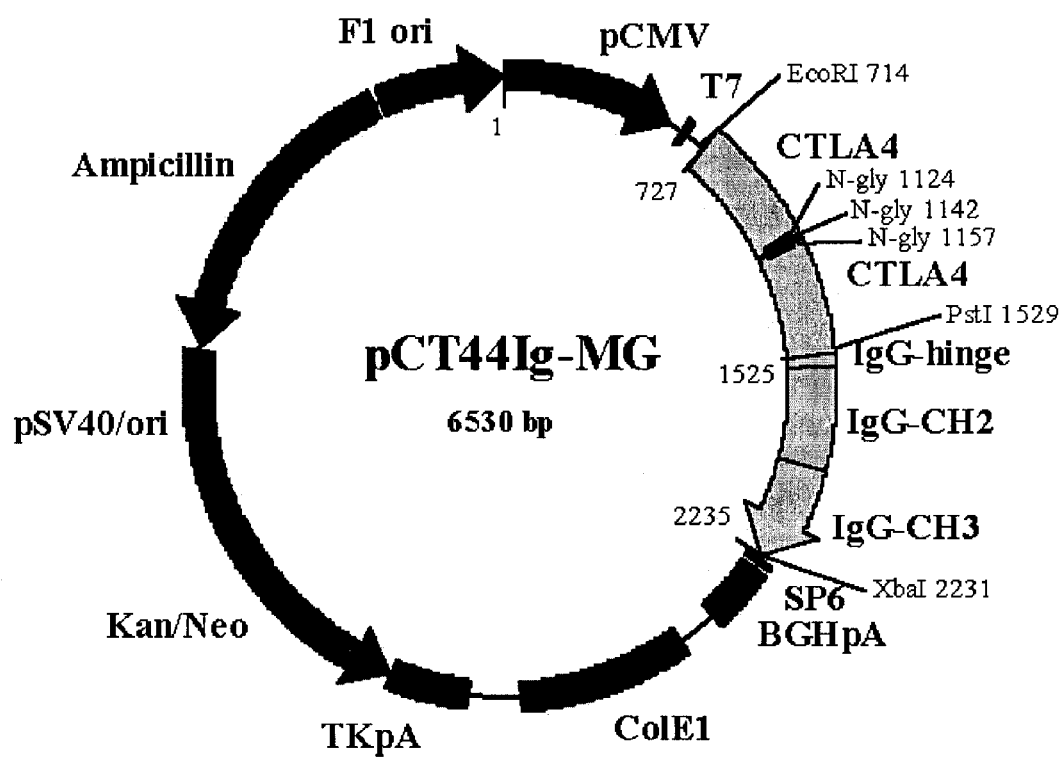
FIG. 14 is a map of a recombinant expression plasmid pCT44Ig-MG expressing a concatameric fusion monomeric protein mgCTLA4-CTLA4/Fc containing three glycosylation motif peptides according to the present invention.
Figure 23:
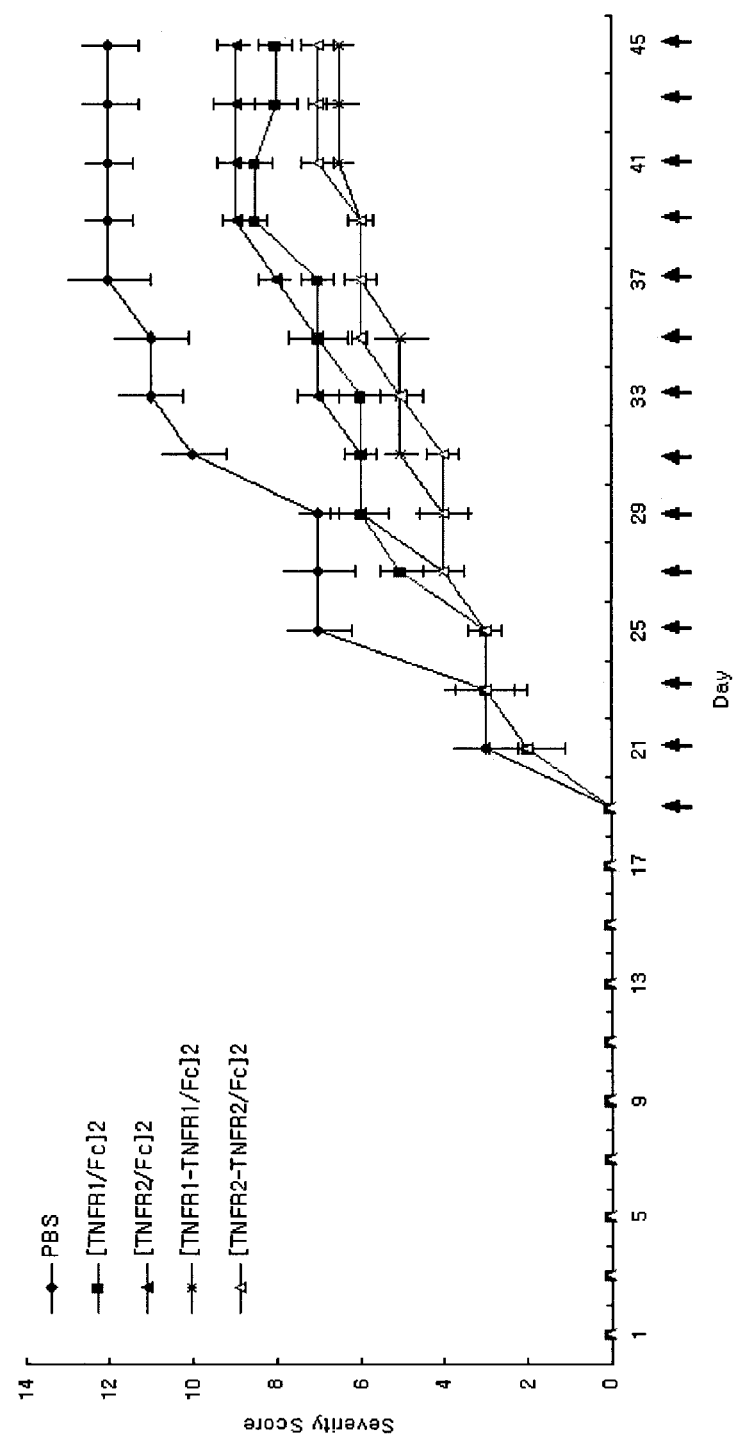
FIG. 23 is a graph showing inhibitory effect of PBS (●) as a control, the conventional simple fusion dimeric proteins [TNFR1/Fc]$_2$ (■) and [TNFR2/Fc]$_2$ (▲), and concatameric fusion dimeric proteins [TNFR1-TNFR1/Fc]$_2$ (x) and [TNFR2-TNFR2/Fc]$_2$ (Δ) according to the present invention on the induction of collagen-induced arthritis (CIA) in DBA/1 mice.

Arthritis was developed 3~4 weeks after immunization with 100 µg of type II collagen in the DBA/1 mice. Red and swollen paws of mice had been observed 3~5 days after onset, and inflammatory arthritis lasted more than 3-4 weeks. Although inflammation was eventually alleviated, damaged joints remained rigid permanently. The degree of arthritis was measured 2~3 times per week on the basis of table 12 which represented subjective index of arthritis severity (measure average of five mice in each experiment). To measure the effects of simple and concatameric fusion dimeric TNFR/Fc on CIA, TNFR/Fc or PBS was i.p. injected into the mice. TNFR/Fc was injected with 10 µg at every 2 days for 19~45 days into 5 mice per experiments (arrows in FIG. 23). PBS was injected into 5 mice as control. As shown in FIG. 7, in the case of mice injected with existing simple dimeric shaped TNFR/Fc fusion protein, it could be seen that the effect decreased to about 26–38% in comparison with the figures of arthritis index in mice injected with PBS as control, but 42–55% decreased in case of concatameric shaped dimer, [TNFR1-TNFR1/Fc]$_2$ and [TNFR2-TNFR2/Fc]$_2$ were injected. Therefore, it could be shown that concatameric fusion dimeric TNFR/Fc fusion proteins have remarkably decreased arthritis of mouse than existing simple fusion dimeric TNFR/Fc fusion proteins.

TABLE 12

Severity score of arthritis

| Severity score | Condition of disease |
| --- | --- |
| 0 | No erythema and swelling |
| 1 | Erythema and mild swelling limited to ankle and tarsal |
| 2 | Erythema and mild swelling spread from ankle to tarsal |
| 3 | Erythema and mild swelling spread from ankle to metatarsal joint |
| 4 | Erythema and severe swelling expend to ankle, legs, and digits |

The results as above represented that concatameric shaped dimeric TNFR/Fc fusion proteins were more effective in decreasing the rate of CIA development than existing simple dimeric fusion proteins, therefore, as use in arthritis therapy, concatameric shaped protein compositions could be more effective therapeutics than existing protein compositions.

The concatameric proteins, concatameric fusion dimeric proteins and their glycosylated proteins of the present invention were able to express increased efficacy and high stability, and to be produced with high yield.

INDUSTRIAL APPLICABILITY

What is claimed is:

1. A dimeric protein comprising two monomeric subunits, each monomeric subunit comprising a concatamer of two identical soluble extracellular domains of a TNFR2 receptor protein, linked to a Fc fragment of an immunoglobulin molecule comprising a hinge region of the immunoglobulin molecule, wherein said monomeric subunits are linked by disulfide bonds at their respective hinge regions; and wherein the monomeric subunit comprises the amino acid sequence of SEQ ID NO:8.

2. The dimeric protein as set forth in claim 1, wherein the immunoglobulin molecule is IgG.

3. A pharmaceutical composition comprising the dimeric protein of claim 1.

* * * * *

SEQUENCE LISTING

```
<160> NUMBER OF SEQ ID NOS: 52

<210> SEQ ID NO 1
<211> LENGTH: 1335
<212> TYPE: DNA
<213> ORGANISM: Homo sapiens
<220> FEATURE:
<221> NAME/KEY: CDS
<222> LOCATION: (1)..(1332)
<223> OTHER INFORMATION: TNFR1-IgG
<220> FEATURE:
<221> NAME/KEY: C_region
<222> LOCATION: (634)..(1335)
<223> OTHER INFORMATION: Hinge, CH2, CH3 region
<220> FEATURE:
<221> NAME/KEY: misc_signal
<222> LOCATION: (160)..(168)
<223> OTHER INFORMATION: N-linked glycosylation site
```

```
<220> FEATURE:
<221> NAME/KEY: misc_signal
<222> LOCATION: (433)..(441)
<223> OTHER INFORMATION: N-linked glycosylation site
<220> FEATURE:
<221> NAME/KEY: misc_signal
<222> LOCATION: (451)..(459)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 25 binding site
<220> FEATURE:
<221> NAME/KEY: primer_bind
<222> LOCATION: (616)..(652)
<223> OTHER INFORMATION: PCR primer SEQ ID : 26(antisense) binding site
<220> FEATURE:
<221> NAME/KEY: primer_bind
<222> LOCATION: (616)..(651)
<223> OTHER INFORMATION: PCR primer SEQ ID : 27 binding site
<220> FEATURE:
<221> NAME/KEY: primer_bind
<222> LOCATION: (1312)..(1335)
<223> OTHER INFORMATION: PCR primer SEQ ID : 28(antisense) binding site
<220> FEATURE:
<221> NAME/KEY: sig_peptide
<222> LOCATION: (1)..(60)
<223> OTHER INFORMATION: signal peptide

<400> SEQUENCE: 1 atg ggc ctc tcc acc gtg cct gac ctg ctg ctg ccg ctg gtg ctc ctg        48
Met Gly Leu Ser Thr Val Pro Asp Leu Leu Leu Pro Leu Val Leu Leu
 1               5                  10                  15 gag ctg ttg gtg gga ata tac ccc tca ggg gtt att gga ctg gtc cct        96
Glu Leu Leu Val Gly Ile Tyr Pro Ser Gly Val Ile Gly Leu Val Pro
            20                  25                  30 cac cta ggg gac agg gag aag aga gat agt gtg tgt ccc caa gga aaa       144
His Leu Gly Asp Arg Glu Lys Arg Asp Ser Val Cys Pro Gln Gly Lys
        35                  40                  45 tat atc cac cct caa aat aat tcg att tgc tgt acc aag tgc cac aaa       192
Tyr Ile His Pro Gln Asn Asn Ser Ile Cys Cys Thr Lys Cys His Lys
    50                  55                  60 gga acc tac ttg tac aat gac tgt cca ggc ccg ggg cag gat acg gac       240
Gly Thr Tyr Leu Tyr Asn Asp Cys Pro Gly Pro Gly Gln Asp Thr Asp
65                  70                  75                  80 tgc agg gag tgt gag agc ggc tcc ttc acc gct tca gaa aac cac ctc       288
Cys Arg Glu Cys Glu Ser Gly Ser Phe Thr Ala Ser Glu Asn His Leu
                85                  90                  95 aga cac tgc ctc agc tgc tcc aaa tgc cga aag gaa atg ggt cag gtg       336
Arg His Cys Leu Ser Cys Ser Lys Cys Arg Lys Glu Met Gly Gln Val
           100                 105                 110 gag atc tct tct tgc aca gtg gac cgg gac acc gtg tgt ggc tgc agg       384
Glu Ile Ser Ser Cys Thr Val Asp Arg Asp Thr Val Cys Gly Cys Arg
       115                 120                 125 aag aac cag tac cgg cat tat tgg agt gaa aac ctt ttc cag tgc ttc       432
Lys Asn Gln Tyr Arg His Tyr Trp Ser Glu Asn Leu Phe Gln Cys Phe
   130                 135                 140 aat tgc agc ctc tgc ctc aat ggg acc gtg cac ctc tcc tgc cag gag       480
Asn Cys Ser Leu Cys Leu Asn Gly Thr Val His Leu Ser Cys Gln Glu
145                 150                 155                 160 aaa cag aac acc gtg tgc acc tgc cat gca ggt ttc ttt cta aga gaa       528
Lys Gln Asn Thr Val Cys Thr Cys His Ala Gly Phe Phe Leu Arg Glu
                165                 170                 175 aac gag tgt gtc tcc tgt agt aac tgt aag aaa agc ctg gag tgc acg       576
Asn Glu Cys Val Ser Cys Ser Asn Cys Lys Lys Ser Leu Glu Cys Thr
            180                 185                 190
```

-continued

| | | |
|---|---|---|
| aag ttg tgc cta ccc cag att gag aat gtt aag ggc act gag gac tca<br>Lys Leu Cys Leu Pro Gln Ile Glu Asn Val Lys Gly Thr Glu Asp Ser<br>                  195                      200                      205 | 624 |
| ggc acc aca gca gag ccc aaa tct tgt gac aaa act cac aca tgc cca<br>Gly Thr Thr Ala Glu Pro Lys Ser Cys Asp Lys Thr His Thr Cys Pro<br>210                      215                      220 | 672 |
| ccg tgc cca gca cct gaa ctc ctg ggg gga ccg tca gtc ttc ctc ttc<br>Pro Cys Pro Ala Pro Glu Leu Leu Gly Gly Pro Ser Val Phe Leu Phe<br>225                    230                      235                    240 | 720 |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>                  245                      250                      255 | 768 |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>                  260                      265                      270 | 816 |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>                  275                      280                      285 | 864 |
| cgg gag gag cag tac aac agc acg tac cgg gtg gtc agc gtc ctc acc<br>Arg Glu Glu Gln Tyr Asn Ser Thr Tyr Arg Val Val Ser Val Leu Thr<br>290                      295                      300 | 912 |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>305                    310                      315                    320 | 960 |
| tcc aac aaa gcc ctc cca gcc ccc atc gag aaa acc atc tcc aaa gcc<br>Ser Asn Lys Ala Leu Pro Ala Pro Ile Glu Lys Thr Ile Ser Lys Ala<br>                  325                      330                      335 | 1008 |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>                  340                      345                      350 | 1056 |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>                  355                      360                    365 | 1104 |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>370                      375                      380 | 1152 |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>385                    390                      395                    400 | 1200 |
| tcc ttc ctc tac agc aag ctc acc gtg gac aag agc agg tgg cag cag<br>Ser Phe Leu Tyr Ser Lys Leu Thr Val Asp Lys Ser Arg Trp Gln Gln<br>                  405                      410                    415 | 1248 |
| ggg aac gtc ttc tca tgc tcc gtg atg cat gag gct ctg cac aac cac<br>Gly Asn Val Phe Ser Cys Ser Val Met His Glu Ala Leu His Asn His<br>                  420                      425                    430 | 1296 |
| tac acg cag aag agc ctc tcc ctg tct ccg ggt aaa           tga<br>Tyr Thr Gln Lys Ser Leu Ser Leu Ser Pro Gly Lys<br>                  435                      440 | 1335 |

<210> SEQ ID NO 2
<211> LENGTH: 444
<212> TYPE: PRT
<213> ORGANISM: Homo sapiens

<400> SEQUENCE: 2

Met Gly Leu Ser Thr Val Pro Asp Leu Leu Leu Pro Leu Val Leu Leu
1                   5                        10                        15

Glu Leu Leu Val Gly Ile Tyr Pro Ser Gly Val Ile Gly Leu Val Pro
                  20                      25                      30

-continued

```
His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
             100                 105                 110

Glu Ile Ser Ser Cys Thr Val Asp Arg Asp Thr Val Cys Gly Cys Arg
         115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                 165                 170                 175

Asn Glu Cys Val Ser Cys Ser Asn Cys Lys Lys Ser Leu Glu Cys Thr
             180                 185                 190

Lys Leu Cys Leu Pro Gln Ile Glu Asn Val Lys Gly Thr Glu Asp Ser
         195                 200                 205

Gly Thr Thr Ala Glu Pro Lys Ser Cys Asp Lys Thr His Thr Cys Pro
     210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                 245                 250                 255

Thr Cys Val Val Val Asp Val Ser His Glu Asp Pro Glu Val Lys Phe
             260                 265                 270

Asn Trp Tyr Val Asp Gly Val Glu Val His Asn Ala Lys Thr Lys Pro
         275                 280                 285

Arg Glu Glu Gln Tyr Asn Ser Thr Tyr Arg Val Val Ser Val Leu Thr
     290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                 325                 330                 335

Lys Gly Gln Pro Arg Glu Pro Gln Val Tyr Thr Leu Pro Pro Ser Arg
             340                 345                 350

Asp Glu Leu Thr Lys Asn Gln Val Ser Leu Thr Cys Leu Val Lys Gly
         355                 360                 365

Phe Tyr Pro Ser Asp Ile Ala Val Glu Trp Glu Ser Asn Gly Gln Pro
     370                 375                 380

Glu Asn Asn Tyr Lys Thr Thr Pro Pro Val Leu Asp Ser Asp Gly Ser
385                 390                 395                 400

Ser Phe Leu Tyr Ser Lys Leu Thr Val Asp Lys Ser Arg Trp Gln Gln
                 405                 410                 415

Gly Asn Val Phe Ser Cys Ser Val Met His Glu Ala Leu His Asn His
             420                 425                 430

Tyr Thr Gln Lys Ser Leu Ser Leu Ser Pro Gly Lys
         435                 440
```

```
<210> SEQ ID NO 3
<211> LENGTH: 1473
<212> TYPE: DNA
<213> ORGANISM: Homo sapiens
<220> FEATURE:
<221> NAME/KEY: CDS
<222> LOCATION: (1)..(1470)
<223> OTHER INFORMATION: TNFR2-IgG
<220> FEATURE:
<221> NAME/KEY: C_region
<222> LOCATION: (772)..(1473)
<223> OTHER INFORMATION: Hinge, CH2, CH3 region
<220> FEATURE:
<221> NAME/KEY: misc_signal
<222> LOCATION: (511)..(519)
<223> OTHER INFORMATION: N-linked glycosylation site
<220> FEATURE:
<221> NAME/KEY: misc_signal
<222> LOCATION: (577)..(585)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 29 binding site
<220> FEATURE:
<221> NAME/KEY: primer_bind
<222> LOCATION: (754)..(790)
<223> OTHER INFORMATION: PCR primer SEQ ID : 30(antisense) binding site
<220> FEATURE:
<221> NAME/KEY: primer_bind
<222> LOCATION: (754)..(790)
<223> OTHER INFORMATION: PCR primer SEQ ID : 31 binding site
<220> FEATURE:
<221> NAME/KEY: primer_bind
<222> LOCATION: (1451)..(1473)
<223> OTHER INFORMATION: PCR primer SEQ ID : 28(antisense) binding site
<220> FEATURE:
<221> NAME/KEY: sig_peptide
<222> LOCATION: (1)..(66)
<223> OTHER INFORMATION: signal peptide

<400> SEQUENCE: 3 atg gcg ccc gtc gcc gtc tgg gcc gcg ctg gcc gtc gga ctg gag ctc      48
Met Ala Pro Val Ala Val Trp Ala Ala Leu Ala Val Gly Leu Glu Leu
  1               5                  10                  15 tgg gct gcg gcg cac gcc ttg ccc gcc cag gtg gca ttt aca ccc tac      96
Trp Ala Ala Ala His Ala Leu Pro Ala Gln Val Ala Phe Thr Pro Tyr
             20                  25                  30 gcc ccg gag ccc ggg agc aca tgc cgg ctc aga gaa tac tat gac cag     144
Ala Pro Glu Pro Gly Ser Thr Cys Arg Leu Arg Glu Tyr Tyr Asp Gln
         35                  40                  45 aca gct cag atg tgc tgc agc aaa tgc tcg ccg ggc caa cat gca aaa     192
Thr Ala Gln Met Cys Cys Ser Lys Cys Ser Pro Gly Gln His Ala Lys
     50                  55                  60 gtc ttc tgt acc aag acc tcg gac acc gtg tgt gac tcc tgt gag gac     240
Val Phe Cys Thr Lys Thr Ser Asp Thr Val Cys Asp Ser Cys Glu Asp
 65                  70                  75                  80 agc aca tac acc cag ctc tgg aac tgg gtt ccc gag tgc ttg agc tgt     288
Ser Thr Tyr Thr Gln Leu Trp Asn Trp Val Pro Glu Cys Leu Ser Cys
                 85                  90                  95 ggc tcc cgc tgt agc tct gac cag gtg gaa act caa gcc tgc act cgg     336
Gly Ser Arg Cys Ser Ser Asp Gln Val Glu Thr Gln Ala Cys Thr Arg
            100                 105                 110 gaa cag aac cgc atc tgc acc tgc agg ccc ggc tgg tac tgc gcg ctg     384
Glu Gln Asn Arg Ile Cys Thr Cys Arg Pro Gly Trp Tyr Cys Ala Leu
        115                 120                 125 agc aag cag gag ggg tgc cgg ctg tgc gcg ccg ctg cgc aag tgc cgc     432
Ser Lys Gln Glu Gly Cys Arg Leu Cys Ala Pro Leu Arg Lys Cys Arg
    130                 135                 140
```

```
ccg ggc ttc ggc gtg gcc aga cca gga act gaa aca tca gac gtg gtg      480
Pro Gly Phe Gly Val Ala Arg Pro Gly Thr Glu Thr Ser Asp Val Val
145                 150                 155                 160 tgc aag ccc tgt gcc ccg ggg acg ttc tcc aac acg act tca tcc acg      528
Cys Lys Pro Cys Ala Pro Gly Thr Phe Ser Asn Thr Thr Ser Ser Thr
                165                 170                 175 gat att tgc agg ccc cac cag atc tgt aac gtg gtg gcc atc cct ggg      576
Asp Ile Cys Arg Pro His Gln Ile Cys Asn Val Val Ala Ile Pro Gly
            180                 185                 190 aat gca agc atg gat gca gtc tgc acg tcc acg tcc ccc acc cgg agt      624
Asn Ala Ser Met Asp Ala Val Cys Thr Ser Thr Ser Pro Thr Arg Ser
        195                 200                 205 atg gcc cca ggg gca gta cac tta ccc cag cca gtg tcc aca cga tcc      672
Met Ala Pro Gly Ala Val His Leu Pro Gln Pro Val Ser Thr Arg Ser
    210                 215                 220 caa cac acg cag cca act cca gaa ccc agc act gct cca agc acc tcc      720
Gln His Thr Gln Pro Thr Pro Glu Pro Ser Thr Ala Pro Ser Thr Ser
225                 230                 235                 240 ttc ctg ctc cca atg ggc ccc agc ccc cca gct gaa ggg agc act ggc      768
Phe Leu Leu Pro Met Gly Pro Ser Pro Pro Ala Glu Gly Ser Thr Gly
                245                 250                 255 gac gca gag ccc aaa tct tgt gac aaa act cac aca tgc cca ccg tgc      816
Asp Ala Glu Pro Lys Ser Cys Asp Lys Thr His Thr Cys Pro Pro Cys
            260                 265                 270 cca gca cct gaa ctc ctg ggg gga ccg tca gtc ttc ctc ttc ccc cca      864
Pro Ala Pro Glu Leu Leu Gly Gly Pro Ser Val Phe Leu Phe Pro Pro
        275                 280                 285 aaa ccc aag gac acc ctc atg atc tcc cgg acc cct gag gtc aca tgc      912
Lys Pro Lys Asp Thr Leu Met Ile Ser Arg Thr Pro Glu Val Thr Cys
    290                 295                 300 gtg gtg gtg gac gtg agc cac gaa gac cct gag gtc aag ttc aac tgg      960
Val Val Val Asp Val Ser His Glu Asp Pro Glu Val Lys Phe Asn Trp
305                 310                 315                 320 tac gtg gac ggc gtg gag gtg cat aat gcc aag aca aag ccg cgg gag     1008
Tyr Val Asp Gly Val Glu Val His Asn Ala Lys Thr Lys Pro Arg Glu
                325                 330                 335 gag cag tac aac agc acg tac cgg gtg gtc agc gtc ctc acc gtc ctg     1056
Glu Gln Tyr Asn Ser Thr Tyr Arg Val Val Ser Val Leu Thr Val Leu
            340                 345                 350 cac cag gac tgg ctg aat ggc aag gag tac aag tgc aag gtc tcc aac     1104
His Gln Asp Trp Leu Asn Gly Lys Glu Tyr Lys Cys Lys Val Ser Asn
        355                 360                 365 aaa gcc ctc cca gcc ccc atc gag aaa acc atc tcc aaa gcc aaa ggg     1152
Lys Ala Leu Pro Ala Pro Ile Glu Lys Thr Ile Ser Lys Ala Lys Gly
    370                 375                 380 cag ccc cga gaa cca cag gtg tac acc ctg ccc cca tcc cgg gat gag     1200
Gln Pro Arg Glu Pro Gln Val Tyr Thr Leu Pro Pro Ser Arg Asp Glu
385                 390                 395                 400 ctg acc aag aac cag gtc agc ctg acc tgc ctg gtc aaa ggc ttc tat     1248
Leu Thr Lys Asn Gln Val Ser Leu Thr Cys Leu Val Lys Gly Phe Tyr
                405                 410                 415 ccc agc gac atc gcc gtg gag tgg gag agc aat ggg cag ccg gag aac     1296
Pro Ser Asp Ile Ala Val Glu Trp Glu Ser Asn Gly Gln Pro Glu Asn
            420                 425                 430 aac tac aag acc acg cct ccc gtg ctg gac tcc gac ggc tcc tcc ttc     1344
Asn Tyr Lys Thr Thr Pro Pro Val Leu Asp Ser Asp Gly Ser Ser Phe
        435                 440                 445 ctc tac agc aag ctc acc gtg gac aag agc agg tgg cag cag ggg aac     1392
Leu Tyr Ser Lys Leu Thr Val Asp Lys Ser Arg Trp Gln Gln Gly Asn
    450                 455                 460
```

```
gtc ttc tca tgc tcc gtg atg cat gag gct ctg cac aac cac tac acg     1440
Val Phe Ser Cys Ser Val Met His Glu Ala Leu His Asn His Tyr Thr
465                 470                 475                 480 cag aag agc ctc tcc ctg tct ccg ggt aaa      tga                    1473
Gln Lys Ser Leu Ser Leu Ser Pro Gly Lys
                485                 490
```

<210> SEQ ID NO 4
<211> LENGTH: 490
<212> TYPE: PRT
<213> ORGANISM: Homo sapiens

<400> SEQUENCE: 4

```
Met Ala Pro Val Ala Val Trp Ala Ala Leu Ala Val Gly Leu Glu Leu
  1               5                  10                  15

Trp Ala Ala His Ala Leu Pro Ala Gln Val Ala Phe Thr Pro Tyr
             20                  25                  30

Ala Pro Glu Pro Gly Ser Thr Cys Arg Leu Arg Glu Tyr Tyr Asp Gln
         35                  40                  45

Thr Ala Gln Met Cys Cys Ser Lys Cys Ser Pro Gly Gln His Ala Lys
     50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                 85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Ala Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335
```

```
Glu Gln Tyr Asn Ser Thr Tyr Arg Val Val Ser Val Leu Thr Val Leu
                    340                 345                 350

His Gln Asp Trp Leu Asn Gly Lys Glu Tyr Lys Cys Lys Val Ser Asn
                355                 360                 365

Lys Ala Leu Pro Ala Pro Ile Glu Lys Thr Ile Ser Lys Ala Lys Gly
            370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
                420                 425                 430

Asn Tyr Lys Thr Thr Pro Pro Val Leu Asp Ser Asp Gly Ser Ser Phe
                435                 440                 445

Leu Tyr Ser Lys Leu Thr Val Asp Lys Ser Arg Trp Gln Gln Gly Asn
            450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490

<210> SEQ ID NO 5
<211> LENGTH: 1887
<212> TYPE: DNA
<213> ORGANISM: Homo sapiens
<220> FEATURE:
<221> NAME/KEY: CDS
<222> LOCATION: (1)..(1884)
<223> OTHER INFORMATION: TNFR1-TNFR1-IgG
<220> FEATURE:
<221> NAME/KEY: C_region
<222> LOCATION: (1716)..(1887)
<223> OTHER INFORMATION: Hinge, CH2, CH3 region
<220> FEATURE:
<221> NAME/KEY: misc_signal
<222> LOCATION: (160)..(168)
<223> OTHER INFORMATION: N-linked glycosylation site
<220> FEATURE:
<221> NAME/KEY: misc_signal
<222> LOCATION: (433)..(441)
<223> OTHER INFORMATION: N-linked glycosylation site
<220> FEATURE:
<221> NAME/KEY: misc_signal
<222> LOCATION: (451)..(459)
<223> OTHER INFORMATION: N-linked glycosylation site
<220> FEATURE:
<221> NAME/KEY: misc_signal
<222> LOCATION: (631)..(639)
<223> OTHER INFORMATION: N-linked glycosylation site
<220> FEATURE:
<221> NAME/KEY: misc_signal
<222> LOCATION: (712)..(720)
<223> OTHER INFORMATION: N-linked glycosylation site
<220> FEATURE:
<221> NAME/KEY: misc_signal
<222> LOCATION: (985)..(993)
<223> OTHER INFORMATION: N-linked glycosylation site
<220> FEATURE:
<221> NAME/KEY: misc_signal
<222> LOCATION: (1003)..(1011)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 25 binding site
<220> FEATURE:
<221> NAME/KEY: primer_bind
<222> LOCATION: (592)..(628)
<223> OTHER INFORMATION: PCR primer SEQ ID : 33(antisense) binding site
```

```
<220> FEATURE:
<221> NAME/KEY: primer_bind
<222> LOCATION: (622)..(655)
<223> OTHER INFORMATION: PCR primer SEQ ID : 32 binding site
<220> FEATURE:
<221> NAME/KEY: primer_bind
<222> LOCATION: (1168)..(1204)
<223> OTHER INFORMATION: PCR primer SEQ ID : 26(antisense) binding site
<220> FEATURE:
<221> NAME/KEY: primer_bind
<222> LOCATION: (1168)..(1204)
<223> OTHER INFORMATION: PCR primer SEQ ID : 27 binding site
<220> FEATURE:
<221> NAME/KEY: primer_bind
<222> LOCATION: (1864)..(1887)
<223> OTHER INFORMATION: PCR primer SEQ ID : 28(antisense) binding site
<220> FEATURE:
<221> NAME/KEY: sig_peptide
<222> LOCATION: (1)..(60)
<223> OTHER INFORMATION: signal peptide

<400> SEQUENCE: 5 atg ggc ctc tcc acc gtg cct gac ctg ctg ctg ccg ctg gtg ctc ctg      48
Met Gly Leu Ser Thr Val Pro Asp Leu Leu Leu Pro Leu Val Leu Leu
  1               5                  10                  15 gag ctg ttg gtg gga ata tac ccc tca ggg gtt att gga ctg gtc cct      96
Glu Leu Leu Val Gly Ile Tyr Pro Ser Gly Val Ile Gly Leu Val Pro
             20                  25                  30 cac cta ggg gac agg gag aag aga gat agt gtg tgt ccc caa gga aaa     144
His Leu Gly Asp Arg Glu Lys Arg Asp Ser Val Cys Pro Gln Gly Lys
         35                  40                  45 tat atc cac cct caa aat aat tcg att tgc tgt acc aag tgc cac aaa     192
Tyr Ile His Pro Gln Asn Asn Ser Ile Cys Cys Thr Lys Cys His Lys
     50                  55                  60 gga acc tac ttg tac aat gac tgt cca ggc ccg ggg cag gat acg gac     240
Gly Thr Tyr Leu Tyr Asn Asp Cys Pro Gly Pro Gly Gln Asp Thr Asp
 65                  70                  75                  80 tgc agg gag tgt gag agc ggc tcc ttc acc gct tca gaa aac cac ctc     288
Cys Arg Glu Cys Glu Ser Gly Ser Phe Thr Ala Ser Glu Asn His Leu
                 85                  90                  95 aga cac tgc ctc agc tgc tcc aaa tgc cga aag gaa atg ggt cag gtg     336
Arg His Cys Leu Ser Cys Ser Lys Cys Arg Lys Glu Met Gly Gln Val
            100                 105                 110 gag atc tct tct tgc aca gtg gac cgg gac acc gtg tgt ggc tgc agg     384
Glu Ile Ser Ser Cys Thr Val Asp Arg Asp Thr Val Cys Gly Cys Arg
        115                 120                 125 aag aac cag tac cgg cat tat tgg agt gaa aac ctt ttc cag tgc ttc     432
Lys Asn Gln Tyr Arg His Tyr Trp Ser Glu Asn Leu Phe Gln Cys Phe
    130                 135                 140 aat tgc agc ctc tgc ctc aat ggg acc gtg cac ctc tcc tgc cag gag     480
Asn Cys Ser Leu Cys Leu Asn Gly Thr Val His Leu Ser Cys Gln Glu
145                 150                 155                 160 aaa cag aac acc gtg tgc acc tgc cat gca ggt ttc ttt cta aga gaa     528
Lys Gln Asn Thr Val Cys Thr Cys His Ala Gly Phe Phe Leu Arg Glu
                165                 170                 175 aac gag tgt gtc tcc tgt agt aac tgt aag aaa agc ctg gag tgc acg     576
Asn Glu Cys Val Ser Cys Ser Asn Cys Lys Lys Ser Leu Glu Cys Thr
            180                 185                 190 aag ttg tgc cta ccc cag att gag aat gtt aag ggc act gag gac gga     624
Lys Leu Cys Leu Pro Gln Ile Glu Asn Val Lys Gly Thr Glu Asp Gly
        195                 200                 205 tcc ggg aac att tca ctg gtc cct cac cta ggg gac agg gag aag aga     672
Ser Gly Asn Ile Ser Leu Val Pro His Leu Gly Asp Arg Glu Lys Arg
    210                 215                 220
```

```
gat agt gtg tgt ccc caa gga aaa tat atc cac cct caa aat aat tcg      720
Asp Ser Val Cys Pro Gln Gly Lys Tyr Ile His Pro Gln Asn Asn Ser
225                 230                 235                 240 att tgc tgt acc aag tgc cac aaa gga acc tac ttg tac aat gac tgt      768
Ile Cys Cys Thr Lys Cys His Lys Gly Thr Tyr Leu Tyr Asn Asp Cys
        245                 250                 255 cca ggc ccg ggg cag gat acg gac tgc agg gag tgt gag agc ggc tcc      816
Pro Gly Pro Gly Gln Asp Thr Asp Cys Arg Glu Cys Glu Ser Gly Ser
            260                 265                 270 ttc acc gct tca gaa aac cac ctc aga cac tgc ctc agc tgc tcc aaa      864
Phe Thr Ala Ser Glu Asn His Leu Arg His Cys Leu Ser Cys Ser Lys
                275                 280                 285 tgc cga aag gaa atg ggt cag gtg gag atc tct tct tgc aca gtg gac      912
Cys Arg Lys Glu Met Gly Gln Val Glu Ile Ser Ser Cys Thr Val Asp
290                 295                 300 cgg gac acc gtg tgt ggc tgc agg aag aac cag tac cgg cat tat tgg      960
Arg Asp Thr Val Cys Gly Cys Arg Lys Asn Gln Tyr Arg His Tyr Trp
305                 310                 315                 320 agt gaa aac ctt ttc cag tgc ttc aat tgc agc ctc tgc ctc aat ggg     1008
Ser Glu Asn Leu Phe Gln Cys Phe Asn Cys Ser Leu Cys Leu Asn Gly
            325                 330                 335 acc gtg cac ctc tcc tgc cag gag aaa cag aac acc gtg tgc acc tgc     1056
Thr Val His Leu Ser Cys Gln Glu Lys Gln Asn Thr Val Cys Thr Cys
                340                 345                 350 cat gca ggt ttc ttt cta aga gaa aac gag tgt gtc tcc tgt agt aac     1104
His Ala Gly Phe Phe Leu Arg Glu Asn Glu Cys Val Ser Cys Ser Asn
355                 360                 365 tgt aag aaa agc ctg gag tgc acg aag ttg tgc cta ccc cag att gag     1152
Cys Lys Lys Ser Leu Glu Cys Thr Lys Leu Cys Leu Pro Gln Ile Glu
370                 375                 380 aat gtt aag ggc act gag gac tca ggc acc aca gca gag ccc aaa tct     1200
Asn Val Lys Gly Thr Glu Asp Ser Gly Thr Thr Ala Glu Pro Lys Ser
385                 390                 395                 400 tgt gac aaa act cac aca tgc cca ccg tgc cca gca cct gaa ctc ctg     1248
Cys Asp Lys Thr His Thr Cys Pro Pro Cys Pro Ala Pro Glu Leu Leu
            405                 410                 415 ggg gga ccg tca gtc ttc ctc ttc ccc cca aaa ccc aag gac acc ctc     1296
Gly Gly Pro Ser Val Phe Leu Phe Pro Pro Lys Pro Lys Asp Thr Leu
                420                 425                 430 atg atc tcc cgg acc cct gag gtc aca tgc gtg gtg gtg gac gtg agc     1344
Met Ile Ser Arg Thr Pro Glu Val Thr Cys Val Val Val Asp Val Ser
                435                 440                 445 cac gaa gac cct gag gtc aag ttc aac tgg tac gtg gac ggc gtg gag     1392
His Glu Asp Pro Glu Val Lys Phe Asn Trp Tyr Val Asp Gly Val Glu
450                 455                 460 gtg cat aat gcc aag aca aag ccg cgg gag gag cag tac aac agc acg     1440
Val His Asn Ala Lys Thr Lys Pro Arg Glu Glu Gln Tyr Asn Ser Thr
465                 470                 475                 480 tac cgg gtg gtc agc gtc ctc acc gtc ctg cac cag gac tgg ctg aat     1488
Tyr Arg Val Val Ser Val Leu Thr Val Leu His Gln Asp Trp Leu Asn
            485                 490                 495 ggc aag gag tac aag tgc aag gtc tcc aac aaa gcc ctc cca gcc ccc     1536
Gly Lys Glu Tyr Lys Cys Lys Val Ser Asn Lys Ala Leu Pro Ala Pro
                500                 505                 510 atc gag aaa acc atc tcc aaa gcc aaa ggg cag ccc cga gaa cca cag     1584
Ile Glu Lys Thr Ile Ser Lys Ala Lys Gly Gln Pro Arg Glu Pro Gln
                515                 520                 525 gtg tac acc ctg ccc cca tcc cgg gat gag ctg acc aag aac cag gtc     1632
Val Tyr Thr Leu Pro Pro Ser Arg Asp Glu Leu Thr Lys Asn Gln Val
530                 535                 540
```

-continued

```
agc ctg acc tgc ctg gtc aaa ggc ttc tat ccc agc gac atc gcc gtg        1680
Ser Leu Thr Cys Leu Val Lys Gly Phe Tyr Pro Ser Asp Ile Ala Val
545                 550                 555                 560 gag tgg gag agc aat ggg cag ccg gag aac aac tac aag acc acg cct        1728
Glu Trp Glu Ser Asn Gly Gln Pro Glu Asn Asn Tyr Lys Thr Thr Pro
                565                 570                 575 ccc gtg ctg gac tcc gac ggc tcc tcc ttc ctc tac agc aag ctc acc        1776
Pro Val Leu Asp Ser Asp Gly Ser Ser Phe Leu Tyr Ser Lys Leu Thr
                580                 585                 590 gtg gac aag agc agg tgg cag cag ggg aac gtc ttc tca tgc tcc gtg        1824
Val Asp Lys Ser Arg Trp Gln Gln Gly Asn Val Phe Ser Cys Ser Val
                595                 600                 605 atg cat gag gct ctg cac aac cac tac acg cag aag agc ctc tcc ctg        1872
Met His Glu Ala Leu His Asn His Tyr Thr Gln Lys Ser Leu Ser Leu
610                 615                 620 tct ccg ggt aaa         tga                                            1887
Ser Pro Gly Lys
625

<210> SEQ ID NO 6
<211> LENGTH: 628
<212> TYPE: PRT
<213> ORGANISM: Homo sapiens

<400> SEQUENCE: 6

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Gly
        195                 200                 205

Ser Gly Asn Ile Ser Leu Val Pro His Leu Gly Asp Arg Glu Lys Arg
210                 215                 220

Asp Ser Val Cys Pro Gln Gly Lys Tyr Ile His Pro Gln Asn Asn Ser
225                 230                 235                 240

Ile Cys Cys Thr Lys Cys His Lys Gly Thr Tyr Leu Tyr Asn Asp Cys
                245                 250                 255
```

```
Pro Gly Pro Gly Gln Asp Thr Asp Cys Arg Glu Cys Glu Ser Gly Ser
            260                 265                 270
Phe Thr Ala Ser Glu Asn His Leu Arg His Cys Leu Ser Cys Ser Lys
        275                 280                 285
Cys Arg Lys Glu Met Gly Gln Val Glu Ile Ser Ser Cys Thr Val Asp
    290                 295                 300
Arg Asp Thr Val Cys Gly Cys Arg Lys Asn Gln Tyr Arg His Tyr Trp
305                 310                 315                 320
Ser Glu Asn Leu Phe Gln Cys Phe Asn Cys Ser Leu Cys Leu Asn Gly
                325                 330                 335
Thr Val His Leu Ser Cys Gln Glu Lys Gln Asn Thr Val Cys Thr Cys
            340                 345                 350
His Ala Gly Phe Phe Leu Arg Glu Asn Glu Cys Val Ser Cys Ser Asn
        355                 360                 365
Cys Lys Lys Ser Leu Glu Cys Thr Lys Leu Cys Leu Pro Gln Ile Glu
    370                 375                 380
Asn Val Lys Gly Thr Glu Asp Ser Gly Thr Thr Ala Glu Pro Lys Ser
385                 390                 395                 400
Cys Asp Lys Thr His Thr Cys Pro Pro Cys Pro Ala Pro Glu Leu Leu
                405                 410                 415
Gly Gly Pro Ser Val Phe Leu Phe Pro Pro Lys Pro Lys Asp Thr Leu
            420                 425                 430
Met Ile Ser Arg Thr Pro Glu Val Thr Cys Val Val Val Asp Val Ser
        435                 440                 445
His Glu Asp Pro Glu Val Lys Phe Asn Trp Tyr Val Asp Gly Val Glu
    450                 455                 460
Val His Asn Ala Lys Thr Lys Pro Arg Glu Glu Gln Tyr Asn Ser Thr
465                 470                 475                 480
Tyr Arg Val Val Ser Val Leu Thr Val Leu His Gln Asp Trp Leu Asn
                485                 490                 495
Gly Lys Glu Tyr Lys Cys Lys Val Ser Asn Lys Ala Leu Pro Ala Pro
            500                 505                 510
Ile Glu Lys Thr Ile Ser Lys Ala Lys Gly Gln Pro Arg Glu Pro Gln
        515                 520                 525
Val Tyr Thr Leu Pro Pro Ser Arg Asp Glu Leu Thr Lys Asn Gln Val
    530                 535                 540
Ser Leu Thr Cys Leu Val Lys Gly Phe Tyr Pro Ser Asp Ile Ala Val
545                 550                 555                 560
Glu Trp Glu Ser Asn Gly Gln Pro Glu Asn Asn Tyr Lys Thr Thr Pro
                565                 570                 575
Pro Val Leu Asp Ser Asp Gly Ser Ser Phe Leu Tyr Ser Lys Leu Thr
            580                 585                 590
Val Asp Lys Ser Arg Trp Gln Gln Gly Asn Val Phe Ser Cys Ser Val
        595                 600                 605
Met His Glu Ala Leu His Asn His Tyr Thr Gln Lys Ser Leu Ser Leu
    610                 615                 620
Ser Pro Gly Lys
625

<210> SEQ ID NO 7
<211> LENGTH: 2163
<212> TYPE: DNA
<213> ORGANISM: Homo sapiens
```

```
<220> FEATURE:
<221> NAME/KEY: CDS
<222> LOCATION: (1)..(2160)
<223> OTHER INFORMATION: TNFR2-TNFR2-IgG
<220> FEATURE:
<221> NAME/KEY: C_region
<222> LOCATION: (1462)..(2163)
<223> OTHER INFORMATION: Hinge, CH2, CH3 region
<220> FEATURE:
<221> NAME/KEY: misc_signal
<222> LOCATION: (511)..(519)
<223> OTHER INFORMATION: N-linked glycosylation site
<220> FEATURE:
<221> NAME/KEY: misc_signal
<222> LOCATION: (577)..(585)
<223> OTHER INFORMATION: N-linked glycosylation site
<220> FEATURE:
<221> NAME/KEY: misc_signal
<222> LOCATION: (769)..(777)
<223> OTHER INFORMATION: N-linked glycosylation site
<220> FEATURE:
<221> NAME/KEY: misc_signal
<222> LOCATION: (1201)..(1209)
<223> OTHER INFORMATION: N-linked glycosylation site
<220> FEATURE:
<221> NAME/KEY: misc_signal
<222> LOCATION: (1267)..(1275)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 29 binding site
<220> FEATURE:
<221> NAME/KEY: primer_bind
<222> LOCATION: (761)..(795)
<223> OTHER INFORMATION: PCR primer SEQ ID : 35(antisense) binding site
<220> FEATURE:
<221> NAME/KEY: primer_bind
<222> LOCATION: (741)..(768)
<223> OTHER INFORMATION: PCR primer SEQ ID : 34 binding site
<220> FEATURE:
<221> NAME/KEY: primer_bind
<222> LOCATION: (1444)..(1480)
<223> OTHER INFORMATION: PCR primer SEQ ID : 30(antisense) binding site
<220> FEATURE:
<221> NAME/KEY: primer_bind
<222> LOCATION: (1444)..(1480)
<223> OTHER INFORMATION: PCR primer SEQ ID : 31 binding site
<220> FEATURE:
<221> NAME/KEY: primer_bind
<222> LOCATION: (2141)..(2163)
<223> OTHER INFORMATION: PCR primer SEQ ID : 28(antisense) binding site
<220> FEATURE:
<221> NAME/KEY: sig_peptide
<222> LOCATION: (1)..(66)
<223> OTHER INFORMATION: signal peptide

<400> SEQUENCE: 7 atg gcg ccc gtc gcc gtc tgg gcc gcg ctg gcc gtc gga ctg gag ctc    48
Met Ala Pro Val Ala Val Trp Ala Ala Leu Ala Val Gly Leu Glu Leu
 1               5                  10                  15 tgg gct gcg gcg cac gcc ttg ccc gcc cag gtg gca ttt aca ccc tac    96
Trp Ala Ala Ala His Ala Leu Pro Ala Gln Val Ala Phe Thr Pro Tyr
            20                  25                  30 gcc ccg gag ccc ggg agc aca tgc cgg ctc aga gaa tac tat gac cag   144
Ala Pro Glu Pro Gly Ser Thr Cys Arg Leu Arg Glu Tyr Tyr Asp Gln
        35                  40                  45 aca gct cag atg tgc tgc agc aaa tgc tcg ccg ggc caa cat gca aaa   192
Thr Ala Gln Met Cys Cys Ser Lys Cys Ser Pro Gly Gln His Ala Lys
    50                  55                  60 gtc ttc tgt acc aag acc tcg gac acc gtg tgt gac tcc tgt gag gac   240
Val Phe Cys Thr Lys Thr Ser Asp Thr Val Cys Asp Ser Cys Glu Asp
65                  70                  75                  80
```

-continued

| | |
|---|---|
| agc aca tac acc cag ctc tgg aac tgg gtt ccc gag tgc ttg agc tgt<br>Ser Thr Tyr Thr Gln Leu Trp Asn Trp Val Pro Glu Cys Leu Ser Cys<br>                 85                       90                     95 | 288 |
| ggc tcc cgc tgt agc tct gac cag gtg gaa act caa gcc tgc act cgg<br>Gly Ser Arg Cys Ser Ser Asp Gln Val Glu Thr Gln Ala Cys Thr Arg<br>               100                    105                   110 | 336 |
| gaa cag aac cgc atc tgc acc tgc agg ccc ggc tgg tac tgc gcg ctg<br>Glu Gln Asn Arg Ile Cys Thr Cys Arg Pro Gly Trp Tyr Cys Ala Leu<br>         115                    120                    125 | 384 |
| agc aag cag gag ggg tgc cgg ctg tgc gcg ccg ctg cgc aag tgc cgc<br>Ser Lys Gln Glu Gly Cys Arg Leu Cys Ala Pro Leu Arg Lys Cys Arg<br>     130                    135                    140 | 432 |
| ccg ggc ttc ggc gtg gcc aga cca gga act gaa aca tca gac gtg gtg<br>Pro Gly Phe Gly Val Ala Arg Pro Gly Thr Glu Thr Ser Asp Val Val<br>145                   150                    155                    160 | 480 |
| tgc aag ccc tgt gcc ccg ggg acg ttc tcc aac act tca tcc acg<br>Cys Lys Pro Cys Ala Pro Gly Thr Phe Ser Asn Thr Thr Ser Ser Thr<br>               165                    170                    175 | 528 |
| gat att tgc agg ccc cac cag atc tgt aac gtg gtg gcc atc cct ggg<br>Asp Ile Cys Arg Pro His Gln Ile Cys Asn Val Val Ala Ile Pro Gly<br>         180                    185                    190 | 576 |
| aat gca agc atg gat gca gtc tgc acg tcc acg tcc ccc acc cgg agt<br>Asn Ala Ser Met Asp Ala Val Cys Thr Ser Thr Ser Pro Thr Arg Ser<br>     195                    200                    205 | 624 |
| atg gcc cca ggg gca gta cac tta ccc cag cca gtg tcc aca cga tcc<br>Met Ala Pro Gly Ala Val His Leu Pro Gln Pro Val Ser Thr Arg Ser<br>210                   215                    220 | 672 |
| caa cac acg cag cca act cca gaa ccc agc act gct cca agc acc tcc<br>Gln His Thr Gln Pro Thr Pro Glu Pro Ser Thr Ala Pro Ser Thr Ser<br>225                   230                    235                    240 | 720 |
| ttc ctg ctc cca atg ggc ccc agc ccc cca gct gaa ggg agc gga tcc<br>Phe Leu Leu Pro Met Gly Pro Ser Pro Pro Ala Glu Gly Ser Gly Ser<br>               245                    250                    255 | 768 |
| aac gca act aca ccc tac gcc ccg gag ccc ggg agc aca tgc cgg ctc<br>Asn Ala Thr Thr Pro Tyr Ala Pro Glu Pro Gly Ser Thr Cys Arg Leu<br>         260                    265                    270 | 816 |
| aga gaa tac tat gac cag aca gct cag atg tgc tgc agc aaa tgc tcg<br>Arg Glu Tyr Tyr Asp Gln Thr Ala Gln Met Cys Cys Ser Lys Cys Ser<br>     275                    280                    285 | 864 |
| ccg ggc caa cat gca aaa gtc ttc tgt acc aag acc tcg gac acc gtg<br>Pro Gly Gln His Ala Lys Val Phe Cys Thr Lys Thr Ser Asp Thr Val<br>290                     295                    300 | 912 |
| tgt gac tcc tgt gag gac agc aca tac acc cag ctc tgg aac tgg gtt<br>Cys Asp Ser Cys Glu Asp Ser Thr Tyr Thr Gln Leu Trp Asn Trp Val<br>305                   310                    315                    320 | 960 |
| ccc gag tgc ttg agc tgt ggc tcc cgc tgt agc tct gac cag gtg gaa<br>Pro Glu Cys Leu Ser Cys Gly Ser Arg Cys Ser Ser Asp Gln Val Glu<br>               325                    330                    335 | 1008 |
| act caa gcc tgc act cgg gaa cag aac cgc atc tgc acc tgc agg ccc<br>Thr Gln Ala Cys Thr Arg Glu Gln Asn Arg Ile Cys Thr Cys Arg Pro<br>         340                    345                    350 | 1056 |
| ggc tgg tac tgc gcg ctg agc aag cag gag ggg tgc cgg ctg tgc gcg<br>Gly Trp Tyr Cys Ala Leu Ser Lys Gln Glu Gly Cys Arg Leu Cys Ala<br>     355                    360                    365 | 1104 |
| ccg ctg cgc aag tgc cgc ccg ggc ttc ggc gtg gcc aga cca gga act<br>Pro Leu Arg Lys Cys Arg Pro Gly Phe Gly Val Ala Arg Pro Gly Thr<br>370                   375                    380 | 1152 |
| gaa aca tca gac gtg gtg tgc aag ccc tgt gcc ccg ggg acg ttc tcc<br>Glu Thr Ser Asp Val Val Cys Lys Pro Cys Ala Pro Gly Thr Phe Ser<br>385                   390                    395                    400 | 1200 |

```
aac acg act tca tcc acg gat att tgc agg ccc cac cag atc tgt aac   1248
Asn Thr Thr Ser Ser Thr Asp Ile Cys Arg Pro His Gln Ile Cys Asn
            405                 410                 415 gtg gtg gcc atc cct ggg aat gca agc atg gat gca gtc tgc acg tcc   1296
Val Val Ala Ile Pro Gly Asn Ala Ser Met Asp Ala Val Cys Thr Ser
        420                 425                 430 acg tcc ccc acc cgg agt atg gcc cca ggg gca gta cac tta ccc cag   1344
Thr Ser Pro Thr Arg Ser Met Ala Pro Gly Ala Val His Leu Pro Gln
        435                 440                 445 cca gtg tcc aca cga tcc caa cac acg cag cca act cca gaa ccc agc   1392
Pro Val Ser Thr Arg Ser Gln His Thr Gln Pro Thr Pro Glu Pro Ser
        450                 455                 460 act gct cca agc acc tcc ttc ctc ctc cca atg ggc ccc agc ccc cca   1440
Thr Ala Pro Ser Thr Ser Phe Leu Leu Pro Met Gly Pro Ser Pro Pro
465                 470                 475                 480 gct gaa ggg agc act ggc gac gca gag ccc aaa tct tgt gac aaa act   1488
Ala Glu Gly Ser Thr Gly Asp Ala Glu Pro Lys Ser Cys Asp Lys Thr
                485                 490                 495 cac aca tgc cca ccg tgc cca gca cct gaa ctc ctg ggg gga ccg tca   1536
His Thr Cys Pro Pro Cys Pro Ala Pro Glu Leu Leu Gly Gly Pro Ser
                500                 505                 510 gtc ttc ctc ttc ccc cca aaa ccc aag gac acc ctc atg atc tcc cgg   1584
Val Phe Leu Phe Pro Pro Lys Pro Lys Asp Thr Leu Met Ile Ser Arg
        515                 520                 525 acc cct gag gtc aca tgc gtg gtg gtg gac gtg agc cac gaa gac cct   1632
Thr Pro Glu Val Thr Cys Val Val Val Asp Val Ser His Glu Asp Pro
        530                 535                 540 gag gtc aag ttc aac tgg tac gtg gac ggc gtg gag gtg cat aat gcc   1680
Glu Val Lys Phe Asn Trp Tyr Val Asp Gly Val Glu Val His Asn Ala
545                 550                 555                 560 aag aca aag ccg cgg gag gag cag tac aac agc acg tac cgg gtg gtc   1728
Lys Thr Lys Pro Arg Glu Glu Gln Tyr Asn Ser Thr Tyr Arg Val Val
                565                 570                 575 agc gtc ctc acc gtc ctg cac cag gac tgg ctg aat ggc aag gag tac   1776
Ser Val Leu Thr Val Leu His Gln Asp Trp Leu Asn Gly Lys Glu Tyr
                580                 585                 590 aag tgc aag gtc tcc aac aaa gcc ctc cca gcc ccc atc gag aaa acc   1824
Lys Cys Lys Val Ser Asn Lys Ala Leu Pro Ala Pro Ile Glu Lys Thr
        595                 600                 605 atc tcc aaa gcc aaa ggg cag ccc cga gaa cca cag gtg tac acc ctg   1872
Ile Ser Lys Ala Lys Gly Gln Pro Arg Glu Pro Gln Val Tyr Thr Leu
        610                 615                 620 ccc cca tcc cgg gat gag ctg acc aag aac cag gtc agc ctg acc tgc   1920
Pro Pro Ser Arg Asp Glu Leu Thr Lys Asn Gln Val Ser Leu Thr Cys
625                 630                 635                 640 ctg gtc aaa ggc ttc tat ccc agc gac atc gcc gtg gag tgg gag agc   1968
Leu Val Lys Gly Phe Tyr Pro Ser Asp Ile Ala Val Glu Trp Glu Ser
                645                 650                 655 aat ggg cag ccg gag aac aac tac aag acc acg cct ccc gtg ctg gac   2016
Asn Gly Gln Pro Glu Asn Asn Tyr Lys Thr Thr Pro Pro Val Leu Asp
                660                 665                 670 tcc gac ggc tcc tcc ttc ctc tac agc aag ctc acc gtg gac aag agc   2064
Ser Asp Gly Ser Ser Phe Leu Tyr Ser Lys Leu Thr Val Asp Lys Ser
        675                 680                 685 agg tgg cag cag ggg aac gtc ttc tca tgc tcc gtg atg cat gag gct   2112
Arg Trp Gln Gln Gly Asn Val Phe Ser Cys Ser Val Met His Glu Ala
        690                 695                 700
```

```
ctg cac aac cac tac acg cag aag agc ctc tcc ctg tct ccg ggt aaa    2160
Leu His Asn His Tyr Thr Gln Lys Ser Leu Ser Leu Ser Pro Gly Lys
705                 710                 715                 720 tga                                                                2163
```

<210> SE NO 8
<211> LENGTH: 720
<212> TYPE: PRT
<213> ORGANISM: Homo sapiens

<400> SEQUENCE: 8

```
Met Ala Pro Val Ala Val Trp Ala Ala Leu Ala Val Gly Leu Glu Leu
  1               5                  10                  15

Trp Ala Ala His Ala Leu Pro Ala Gln Val Ala Phe Thr Pro Tyr
             20                  25                  30

Ala Pro Glu Pro Gly Ser Thr Cys Arg Leu Arg Glu Tyr Tyr Asp Gln
             35                  40                  45

Thr Ala Gln Met Cys Cys Ser Lys Cys Ser Pro Gly Gln His Ala Lys
 50                      55                      60

Val Phe Cys Thr Lys Thr Ser Asp Thr Val Cys Asp Ser Cys Glu Asp
 65                      70                      75              80

Ser Thr Tyr Thr Gln Leu Trp Asn Trp Val Pro Glu Cys Leu Ser Cys
                 85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Gly Ser
                245                 250                 255

Asn Ala Thr Thr Pro Tyr Ala Pro Glu Pro Gly Ser Thr Cys Arg Leu
            260                 265                 270

Arg Glu Tyr Tyr Asp Gln Thr Ala Gln Met Cys Cys Ser Lys Cys Ser
            275                 280                 285

Pro Gly Gln His Ala Lys Val Phe Cys Thr Lys Thr Ser Asp Thr Val
            290                 295                 300

Cys Asp Ser Cys Glu Asp Ser Thr Tyr Thr Gln Leu Trp Asn Trp Val
305                 310                 315                 320

Pro Glu Cys Leu Ser Cys Gly Ser Arg Cys Ser Ser Asp Gln Val Glu
                325                 330                 335

Thr Gln Ala Cys Thr Arg Glu Gln Asn Arg Ile Cys Thr Cys Arg Pro
            340                 345                 350
```

```
Gly Trp Tyr Cys Ala Leu Ser Lys Gln Glu Gly Cys Arg Leu Cys Ala
            355                 360                 365

Pro Leu Arg Lys Cys Arg Pro Gly Phe Gly Val Ala Arg Pro Gly Thr
    370                 375                 380

Glu Thr Ser Asp Val Val Cys Lys Pro Cys Ala Pro Gly Thr Phe Ser
385                 390                 395                 400

Asn Thr Thr Ser Ser Thr Asp Ile Cys Arg Pro His Gln Ile Cys Asn
                405                 410                 415

Val Val Ala Ile Pro Gly Asn Ala Ser Met Asp Ala Val Cys Thr Ser
            420                 425                 430

Thr Ser Pro Thr Arg Ser Met Ala Pro Gly Ala Val His Leu Pro Gln
        435                 440                 445

Pro Val Ser Thr Arg Ser Gln His Thr Gln Pro Thr Pro Glu Pro Ser
    450                 455                 460

Thr Ala Pro Ser Thr Ser Phe Leu Leu Pro Met Gly Pro Ser Pro Pro
465                 470                 475                 480

Ala Glu Gly Ser Thr Gly Asp Ala Glu Pro Lys Ser Cys Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Asp Glu Leu Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Ser Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 9
<211> LENGTH: 1827
<212> TYPE: DNA
<213> ORGANISM: Homo sapiens
<220> FEATURE:
<221> NAME/KEY: CDS
<222> LOCATION: (1)..(1824)
<223> OTHER INFORMATION: mgTNFR1-TNFR1-IgG
```

```
<220> FEATURE:
<221> NAME/KEY: C_region
<222> LOCATION: (1126)..(1827)
<223> OTHER INFORMATION: Hinge, CH2, CH3 region
<220> FEATURE:
<221> NAME/KEY: misc_signal
<222> LOCATION: (160)..(168)
<223> OTHER INFORMATION: N-linked glycosylation site
<220> FEATURE:
<221> NAME/KEY: misc_signal
<222> LOCATION: (433)..(441)
<223> OTHER INFORMATION: N-linked glycosylation site
<220> FEATURE:
<221> NAME/KEY: misc_signal
<222> LOCATION: (451)..(459)
<223> OTHER INFORMATION: N-linked glycosylation site
<220> FEATURE:
<221> NAME/KEY: misc_signal
<222> LOCATION: (565)..(573)
<223> OTHER INFORMATION: N-linked glycosylation site
<220> FEATURE:
<221> NAME/KEY: misc_signal
<222> LOCATION: (574)..(582)
<223> OTHER INFORMATION: N-linked glycosylation site
<220> FEATURE:
<221> NAME/KEY: misc_signal
<222> LOCATION: (592)..(600)
<223> OTHER INFORMATION: N-linked glycosylation site
<220> FEATURE:
<221> NAME/KEY: misc_signal
<222> LOCATION: (610)..(618)
<223> OTHER INFORMATION: N-linked glycosylation site
<220> FEATURE:
<221> NAME/KEY: misc_signal
<222> LOCATION: (925)..(933)
<223> OTHER INFORMATION: N-linked glycosylation site
<220> FEATURE:
<221> NAME/KEY: misc_signal
<222> LOCATION: (943)..(951)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 25 binding site
<220> FEATURE:
<221> NAME/KEY: primer_bind
<222> LOCATION: (545)..(606)
<223> OTHER INFORMATION: PCR primer SEQ ID : 37(antisense) binding site
<220> FEATURE:
<221> NAME/KEY: primer_bind
<222> LOCATION: (559)..(621)
<223> OTHER INFORMATION: PCR primer SEQ ID : 36 binding site
<220> FEATURE:
<221> NAME/KEY: primer_bind
<222> LOCATION: (1108)..(1144)
<223> OTHER INFORMATION: PCR primer SEQ ID : 26(antisense) binding site
<220> FEATURE:
<221> NAME/KEY: primer_bind
<222> LOCATION: (1108)..(1144)
<223> OTHER INFORMATION: PCR primer SEQ ID : 27 binding site
<220> FEATURE:
<221> NAME/KEY: primer_bind
<222> LOCATION: (1804)..(1827)
<223> OTHER INFORMATION: PCR primer SEQ ID : 28(antisense) binding site
<220> FEATURE:
<221> NAME/KEY: sig_peptide
<222> LOCATION: (1)..(60)
<223> OTHER INFORMATION: signal peptide

<400> SEQUENCE: 9 atg ggc ctc tcc acc gtg cct gac ctg ctg ctg ccg ctg gtg ctc ctg      48
Met Gly Leu Ser Thr Val Pro Asp Leu Leu Leu Pro Leu Val Leu Leu
 1               5                  10                  15 gag ctg ttg gtg gga ata tac ccc tca ggg gtt att gga ctg gtc cct      96
Glu Leu Leu Val Gly Ile Tyr Pro Ser Gly Val Ile Gly Leu Val Pro
             20                  25                  30
```

-continued

| | |
|---|---|
| cac cta ggg gac agg gag aag aga gat agt gtg tgt ccc caa gga aaa<br>His Leu Gly Asp Arg Glu Lys Arg Asp Ser Val Cys Pro Gln Gly Lys<br>35                                      40                           45 | 144 |
| tat atc cac cct caa aat aat tcg att tgc tgt acc aag tgc cac aaa<br>Tyr Ile His Pro Gln Asn Asn Ser Ile Cys Cys Thr Lys Cys His Lys<br>    50                              55                          60 | 192 |
| gga acc tac ttg tac aat gac tgt cca ggc ccg ggg cag gat acg gac<br>Gly Thr Tyr Leu Tyr Asn Asp Cys Pro Gly Pro Gly Gln Asp Thr Asp<br>65                                70                           75                    80 | 240 |
| tgc agg gag tgt gag agc ggc tcc ttc acc gct tca gaa aac cac ctc<br>Cys Arg Glu Cys Glu Ser Gly Ser Phe Thr Ala Ser Glu Asn His Leu<br>                              85                          90                           95 | 288 |
| aga cac tgc ctc agc tgc tcc aaa tgc cga aag gaa atg ggt cag gtg<br>Arg His Cys Leu Ser Cys Ser Lys Cys Arg Lys Glu Met Gly Gln Val<br>                        100                        105                        110 | 336 |
| gag atc tct tct tgc aca gtg gac cgg gac acc gtg tgt ggc tgc agg<br>Glu Ile Ser Ser Cys Thr Val Asp Arg Asp Thr Val Cys Gly Cys Arg<br>               115                        120                        125 | 384 |
| aag aac cag tac cgg cat tat tgg agt gaa aac ctt ttc cag tgc ttc<br>Lys Asn Gln Tyr Arg His Tyr Trp Ser Glu Asn Leu Phe Gln Cys Phe<br>130                                135                          140 | 432 |
| aat tgc agc ctc tgc ctc aat ggg acc gtg cac ctc tcc tgc cag gag<br>Asn Cys Ser Leu Cys Leu Asn Gly Thr Val His Leu Ser Cys Gln Glu<br>145                            150                        155                      160 | 480 |
| aaa cag aac acc gtg tgc acc tgc cat gca ggt ttc ttt cta aga gaa<br>Lys Gln Asn Thr Val Cys Thr Cys His Ala Gly Phe Phe Leu Arg Glu<br>                        165                        170                        175 | 528 |
| aac gag tgt gtc tcc tgt agt aac tgt aag aaa agc aac gag acc aac<br>Asn Glu Cys Val Ser Cys Ser Asn Cys Lys Lys Ser Asn Glu Thr Asn<br>               180                        185                        190 | 576 |
| aag acc tgc cta cac aac ggg tcc agg gag aag aac gat agt gtg tgt<br>Lys Thr Cys Leu His Asn Gly Ser Arg Glu Lys Asn Asp Ser Val Cys<br>                        195                        200                        205 | 624 |
| ccc caa gga aaa tat atc cac cct caa aat aat tcg att tgc tgt acc<br>Pro Gln Gly Lys Tyr Ile His Pro Gln Asn Asn Ser Ile Cys Cys Thr<br>210                                215                          220 | 672 |
| aag tgc cac aaa gga acc tac ttg tac aat gac tgt cca ggc ccg ggg<br>Lys Cys His Lys Gly Thr Tyr Leu Tyr Asn Asp Cys Pro Gly Pro Gly<br>225                              230                        235                      240 | 720 |
| cag gat acg gac tgc agg gag tgt gag agc ggc tcc ttc acc gct tca<br>Gln Asp Thr Asp Cys Arg Glu Cys Glu Ser Gly Ser Phe Thr Ala Ser<br>                        245                        250                        255 | 768 |
| gaa aac cac ctc aga cac tgc ctc agc tgc tcc aaa tgc cga aag gaa<br>Glu Asn His Leu Arg His Cys Leu Ser Cys Ser Lys Cys Arg Lys Glu<br>                      260                        265                        270 | 816 |
| atg ggt cag gtg gag atc tct tct tgc aca gtg gac cgg gac acc gtg<br>Met Gly Gln Val Glu Ile Ser Ser Cys Thr Val Asp Arg Asp Thr Val<br>               275                        280                        285 | 864 |
| tgt ggc tgc agg aag aac cag tac cgg cat tat tgg agt gaa aac ctt<br>Cys Gly Cys Arg Lys Asn Gln Tyr Arg His Tyr Trp Ser Glu Asn Leu<br>          290                        295                        300 | 912 |
| ttc cag tgc ttc aat tgc agc ctc tgc ctc aat ggg acc gtg cac ctc<br>Phe Gln Cys Phe Asn Cys Ser Leu Cys Leu Asn Gly Thr Val His Leu<br>305                                310                        315                      320 | 960 |
| tcc tgc cag gag aaa cag aac acc gtg tgc acc tgc cat gca ggt ttc<br>Ser Cys Gln Glu Lys Gln Asn Thr Val Cys Thr Cys His Ala Gly Phe<br>                        325                        330                        335 | 1008 |
| ttt cta aga gaa aac gag tgt gtc tcc tgt agt aac tgt aag aaa agc<br>Phe Leu Arg Glu Asn Glu Cys Val Ser Cys Ser Asn Cys Lys Lys Ser<br>                      340                        345                        350 | 1056 |

```
ctg gag tgc acg aag ttg tgc cta ccc cag att gag aat gtt aag ggc      1104
Leu Glu Cys Thr Lys Leu Cys Leu Pro Gln Ile Glu Asn Val Lys Gly
        355                 360                 365 act gag gac tca ggc acc aca gca gag ccc aaa tct tgt gac aaa act      1152
Thr Glu Asp Ser Gly Thr Thr Ala Glu Pro Lys Ser Cys Asp Lys Thr
370                 375                 380 cac aca tgc cca ccg tgc cca gca cct gaa ctc ctg ggg gga ccg tca      1200
His Thr Cys Pro Pro Cys Pro Ala Pro Glu Leu Leu Gly Gly Pro Ser
385                 390                 395                 400 gtc ttc ctc ttc ccc cca aaa ccc aag gac acc ctc atg atc tcc cgg      1248
Val Phe Leu Phe Pro Pro Lys Pro Lys Asp Thr Leu Met Ile Ser Arg
                405                 410                 415 acc cct gag gtc aca tgc gtg gtg gtg gac gtg agc cac gaa gac cct      1296
Thr Pro Glu Val Thr Cys Val Val Val Asp Val Ser His Glu Asp Pro
            420                 425                 430 gag gtc aag ttc aac tgg tac gtg gac ggc gtg gag gtg cat aat gcc      1344
Glu Val Lys Phe Asn Trp Tyr Val Asp Gly Val Glu Val His Asn Ala
        435                 440                 445 aag aca aag ccg cgg gag gag cag tac aac agc acg tac cgg gtg gtc      1392
Lys Thr Lys Pro Arg Glu Glu Gln Tyr Asn Ser Thr Tyr Arg Val Val
450                 455                 460 agc gtc ctc acc gtc ctg cac cag gac tgg ctg aat ggc aag gag tac      1440
Ser Val Leu Thr Val Leu His Gln Asp Trp Leu Asn Gly Lys Glu Tyr
465                 470                 475                 480 aag tgc aag gtc tcc aac aaa gcc ctc cca gcc ccc atc gag aaa acc      1488
Lys Cys Lys Val Ser Asn Lys Ala Leu Pro Ala Pro Ile Glu Lys Thr
                485                 490                 495 atc tcc aaa gcc aaa ggg cag ccc cga gaa cca cag gtg tac acc ctg      1536
Ile Ser Lys Ala Lys Gly Gln Pro Arg Glu Pro Gln Val Tyr Thr Leu
            500                 505                 510 ccc cca tcc cgg gat gag ctg acc aag aac cag gtc agc ctg acc tgc      1584
Pro Pro Ser Arg Asp Glu Leu Thr Lys Asn Gln Val Ser Leu Thr Cys
        515                 520                 525 ctg gtc aaa ggc ttc tat ccc agc gac atc gcc gtg gag tgg gag agc      1632
Leu Val Lys Gly Phe Tyr Pro Ser Asp Ile Ala Val Glu Trp Glu Ser
530                 535                 540 aat ggg cag ccg gag aac aac tac aag acc acg cct ccc gtg ctg gac      1680
Asn Gly Gln Pro Glu Asn Asn Tyr Lys Thr Thr Pro Pro Val Leu Asp
545                 550                 555                 560 tcc gac ggc tcc ttc ttc ctc tac agc aag ctc acc gtg gac aag agc      1728
Ser Asp Gly Ser Phe Phe Leu Tyr Ser Lys Leu Thr Val Asp Lys Ser
                565                 570                 575 agg tgg cag cag ggg aac gtc ttc tca tgc tcc gtg atg cat gag gct      1776
Arg Trp Gln Gln Gly Asn Val Phe Ser Cys Ser Val Met His Glu Ala
            580                 585                 590 ctg cac aac cac tac acg cag aag agc ctc tcc ctg tct ccg ggt aaa      1824
Leu His Asn His Tyr Thr Gln Lys Ser Leu Ser Leu Ser Pro Gly Lys
        595                 600                 605 tga                                                                  1827

<210> SEQ ID NO 10
<211> LENGTH: 608
<212> TYPE: PRT
<213> ORGANISM: Homo sapiens

<400> SEQUENCE: 10

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30
```

```
His Leu Gly Asp Arg Glu Lys Arg Asp Ser Val Cys Pro Gln Gly Lys
            35                  40                  45
Tyr Ile His Pro Gln Asn Asn Ser Ile Cys Cys Thr Lys Cys His Lys
        50                  55                  60
Gly Thr Tyr Leu Tyr Asn Asp Cys Pro Gly Pro Gly Gln Asp Thr Asp
 65                  70                  75                  80
Cys Arg Glu Cys Glu Ser Gly Ser Phe Thr Ala Ser Glu Asn His Leu
                85                  90                  95
Arg His Cys Leu Ser Cys Ser Lys Cys Arg Lys Glu Met Gly Gln Val
                100                 105                 110
Glu Ile Ser Ser Cys Thr Val Asp Arg Asp Thr Val Cys Gly Cys Arg
            115                 120                 125
Lys Asn Gln Tyr Arg His Tyr Trp Ser Glu Asn Leu Phe Gln Cys Phe
130                 135                 140
Asn Cys Ser Leu Cys Leu Asn Gly Thr Val His Leu Ser Cys Gln Glu
145                 150                 155                 160
Lys Gln Asn Thr Val Cys Thr Cys His Ala Gly Phe Phe Leu Arg Glu
                165                 170                 175
Asn Glu Cys Val Ser Cys Ser Asn Cys Lys Lys Ser Asn Glu Thr Asn
            180                 185                 190
Lys Thr Cys Leu His Asn Gly Ser Arg Glu Lys Asn Asp Ser Val Cys
        195                 200                 205
Pro Gln Gly Lys Tyr Ile His Pro Gln Asn Asn Ser Ile Cys Cys Thr
    210                 215                 220
Lys Cys His Lys Gly Thr Tyr Leu Tyr Asn Asp Cys Pro Gly Pro Gly
225                 230                 235                 240
Gln Asp Thr Asp Cys Arg Glu Cys Glu Ser Gly Ser Phe Thr Ala Ser
                245                 250                 255
Glu Asn His Leu Arg His Cys Leu Ser Cys Ser Lys Cys Arg Lys Glu
            260                 265                 270
Met Gly Gln Val Glu Ile Ser Ser Cys Thr Val Asp Arg Asp Thr Val
        275                 280                 285
Cys Gly Cys Arg Lys Asn Gln Tyr Arg His Tyr Trp Ser Glu Asn Leu
    290                 295                 300
Phe Gln Cys Phe Asn Cys Ser Leu Cys Leu Asn Gly Thr Val His Leu
305                 310                 315                 320
Ser Cys Gln Glu Lys Gln Asn Thr Val Cys Thr Cys His Ala Gly Phe
                325                 330                 335
Phe Leu Arg Glu Asn Glu Cys Val Ser Cys Ser Asn Cys Lys Lys Ser
            340                 345                 350
Leu Glu Cys Thr Lys Leu Cys Leu Pro Gln Ile Glu Asn Val Lys Gly
        355                 360                 365
Thr Glu Asp Ser Gly Thr Thr Ala Glu Pro Lys Ser Cys Asp Lys Thr
    370                 375                 380
His Thr Cys Pro Pro Cys Pro Ala Pro Glu Leu Leu Gly Gly Pro Ser
385                 390                 395                 400
Val Phe Leu Phe Pro Pro Lys Pro Lys Asp Thr Leu Met Ile Ser Arg
                405                 410                 415
Thr Pro Glu Val Thr Cys Val Val Val Asp Val Ser His Glu Asp Pro
            420                 425                 430
Glu Val Lys Phe Asn Trp Tyr Val Asp Gly Val Glu Val His Asn Ala
        435                 440                 445
```

-continued

```
Lys Thr Lys Pro Arg Glu Glu Gln Tyr Asn Ser Thr Tyr Arg Val Val
    450                 455                 460

Ser Val Leu Thr Val Leu His Gln Asp Trp Leu Asn Gly Lys Glu Tyr
465                 470                 475                 480

Lys Cys Lys Val Ser Asn Lys Ala Leu Pro Ala Pro Ile Glu Lys Thr
                485                 490                 495

Ile Ser Lys Ala Lys Gly Gln Pro Arg Glu Pro Gln Val Tyr Thr Leu
            500                 505                 510

Pro Pro Ser Arg Asp Glu Leu Thr Lys Asn Gln Val Ser Leu Thr Cys
        515                 520                 525

Leu Val Lys Gly Phe Tyr Pro Ser Asp Ile Ala Val Glu Trp Glu Ser
    530                 535                 540

Asn Gly Gln Pro Glu Asn Asn Tyr Lys Thr Thr Pro Pro Val Leu Asp
545                 550                 555                 560

Ser Asp Gly Ser Phe Phe Leu Tyr Ser Lys Leu Thr Val Asp Lys Ser
                565                 570                 575

Arg Trp Gln Gln Gly Asn Val Phe Ser Cys Ser Val Met His Glu Ala
            580                 585                 590

Leu His Asn His Tyr Thr Gln Lys Ser Leu Ser Leu Ser Pro Gly Lys
        595                 600                 605
```

```
<210> SEQ ID NO 11
<211> LENGTH: 1980
<212> TYPE: DNA
<213> ORGANISM: Homo sapiens
<220> FEATURE:
<221> NAME/KEY: CDS
<222> LOCATION: (1)..(1977)
<223> OTHER INFORMATION: mgTNFR2-TNFR2-IgG
<220> FEATURE:
<221> NAME/KEY: C_region
<222> LOCATION: (1279)..(1980)
<223> OTHER INFORMATION: Hinge, CH2, CH3 region
<220> FEATURE:
<221> NAME/KEY: misc_signal
<222> LOCATION: (511)..(519)
<223> OTHER INFORMATION: N-linked glycosylation site
<220> FEATURE:
<221> NAME/KEY: misc_signal
<222> LOCATION: (577)..(585)
<223> OTHER INFORMATION: N-linked glycosylation site
<220> FEATURE:
<221> NAME/KEY: misc_signal
<222> LOCATION: (595)..(603)
<223> OTHER INFORMATION: N-linked glycosylation site
<220> FEATURE:
<221> NAME/KEY: misc_signal
<222> LOCATION: (616)..(624)
<223> OTHER INFORMATION: N-linked glycosylation site
<220> FEATURE:
<221> NAME/KEY: misc_signal
<222> LOCATION: (1018)..(1026)
<223> OTHER INFORMATION: N-linked glycosylation site
<220> FEATURE:
<221> NAME/KEY: misc_signal
<222> LOCATION: (1084)..(1092)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 29 binding site
<220> FEATURE:
<221> NAME/KEY: primer_bind
<222> LOCATION: (586)..(627)
<223> OTHER INFORMATION: PCR primer SEQ ID : 39(antisense) binding site
<220> FEATURE:
<221> NAME/KEY: primer_bind
<222> LOCATION: (586)..(630)
<223> OTHER INFORMATION: PCR primer SEQ ID : 38 binding site
```

```
<220> FEATURE:
<221> NAME/KEY: primer_bind
<222> LOCATION: (1261)..(1296)
<223> OTHER INFORMATION: PCR primer SEQ ID : 30(antisense) binding site
<220> FEATURE:
<221> NAME/KEY: primer_bind
<222> LOCATION: (1261)..(1296)
<223> OTHER INFORMATION: PCR primer SEQ ID : 31 binding site
<220> FEATURE:
<221> NAME/KEY: primer_bind
<222> LOCATION: (1957)..(1980)
<223> OTHER INFORMATION: PCR primer SEQ ID : 28(antisense) binding site
<220> FEATURE:
<221> NAME/KEY: sig_peptide
<222> LOCATION: (1)..(66)
<223> OTHER INFORMATION: signal peptide

<400> SEQUENCE: 11
```

| | | | | | | | | | | | | | | | |
|---|---|---|---|---|---|---|---|---|---|---|---|---|---|---|---|
| atg | gcg | ccc | gtc | gcc | gtc | tgg | gcc | gcg | ctg | gcc | gtc | gga | ctg | gag | ctc | 48 |
| Met | Ala | Pro | Val | Ala | Val | Trp | Ala | Ala | Leu | Ala | Val | Gly | Leu | Glu | Leu | |
| 1 | | | | 5 | | | | | 10 | | | | | 15 | | |

| | | | | | | | | | | | |
|---|---|---|---|---|---|---|---|---|---|---|---|
| tgg | gct | gcg | gcg | cac | gcc | ttg | ccc | gcc | cag | gtg | gca | ttt | aca | ccc | tac | 96 |
| Trp | Ala | Ala | Ala | His | Ala | Leu | Pro | Ala | Gln | Val | Ala | Phe | Thr | Pro | Tyr | |
| | | | 20 | | | | | 25 | | | | | 30 | | | |

| | | | | | | | | | | | |
|---|---|---|---|---|---|---|---|---|---|---|---|
| gcc | ccg | gag | ccc | ggg | agc | aca | tgc | cgg | ctc | aga | gaa | tac | tat | gac | cag | 144 |
| Ala | Pro | Glu | Pro | Gly | Ser | Thr | Cys | Arg | Leu | Arg | Glu | Tyr | Tyr | Asp | Gln | |
| | | 35 | | | | | 40 | | | | | 45 | | | | |

| | | | | | | | | | | | |
|---|---|---|---|---|---|---|---|---|---|---|---|
| aca | gct | cag | atg | tgc | tgc | agc | aaa | tgc | tcg | ccg | ggc | caa | cat | gca | aaa | 192 |
| Thr | Ala | Gln | Met | Cys | Cys | Ser | Lys | Cys | Ser | Pro | Gly | Gln | His | Ala | Lys | |
| 50 | | | | | 55 | | | | | 60 | | | | | | |

| | | | | | | | | | | | |
|---|---|---|---|---|---|---|---|---|---|---|---|
| gtc | ttc | tgt | acc | aag | acc | tcg | gac | acc | gtg | tgt | gac | tcc | tgt | gag | gac | 240 |
| Val | Phe | Cys | Thr | Lys | Thr | Ser | Asp | Thr | Val | Cys | Asp | Ser | Cys | Glu | Asp | |
| 65 | | | | 70 | | | | | 75 | | | | | 80 | | |

| | | | | | | | | | | | |
|---|---|---|---|---|---|---|---|---|---|---|---|
| agc | aca | tac | acc | cag | ctc | tgg | aac | tgg | gtt | ccc | gag | tgc | ttg | agc | tgt | 288 |
| Ser | Thr | Tyr | Thr | Gln | Leu | Trp | Asn | Trp | Val | Pro | Glu | Cys | Leu | Ser | Cys | |
| | | | | 85 | | | | | 90 | | | | | 95 | | |

| | | | | | | | | | | | |
|---|---|---|---|---|---|---|---|---|---|---|---|
| ggc | tcc | cgc | tgt | agc | tct | gac | cag | gtg | gaa | act | caa | gcc | tgc | act | cgg | 336 |
| Gly | Ser | Arg | Cys | Ser | Ser | Asp | Gln | Val | Glu | Thr | Gln | Ala | Cys | Thr | Arg | |
| | | | 100 | | | | | 105 | | | | | 110 | | | |

| | | | | | | | | | | | |
|---|---|---|---|---|---|---|---|---|---|---|---|
| gaa | cag | aac | cgc | atc | tgc | acc | tgc | agg | ccc | ggc | tgg | tac | tgc | gcg | ctg | 384 |
| Glu | Gln | Asn | Arg | Ile | Cys | Thr | Cys | Arg | Pro | Gly | Trp | Tyr | Cys | Ala | Leu | |
| | | 115 | | | | | 120 | | | | | 125 | | | | |

| | | | | | | | | | | | |
|---|---|---|---|---|---|---|---|---|---|---|---|
| agc | aag | cag | gag | ggg | tgc | cgg | ctg | tgc | gcg | ccg | ctg | cgc | aag | tgc | cgc | 432 |
| Ser | Lys | Gln | Glu | Gly | Cys | Arg | Leu | Cys | Ala | Pro | Leu | Arg | Lys | Cys | Arg | |
| | 130 | | | | | 135 | | | | | 140 | | | | | |

| | | | | | | | | | | | |
|---|---|---|---|---|---|---|---|---|---|---|---|
| ccg | ggc | ttc | ggc | gtg | gcc | aga | cca | gga | act | gaa | aca | tca | gac | gtg | gtg | 480 |
| Pro | Gly | Phe | Gly | Val | Ala | Arg | Pro | Gly | Thr | Glu | Thr | Ser | Asp | Val | Val | |
| 145 | | | | 150 | | | | | 155 | | | | | 160 | | |

| | | | | | | | | | | | |
|---|---|---|---|---|---|---|---|---|---|---|---|
| tgc | aag | ccc | tgt | gcc | ccg | ggg | acg | ttc | tcc | aac | acg | act | tca | tcc | acg | 528 |
| Cys | Lys | Pro | Cys | Ala | Pro | Gly | Thr | Phe | Ser | Asn | Thr | Thr | Ser | Ser | Thr | |
| | | | | 165 | | | | | 170 | | | | | 175 | | |

| | | | | | | | | | | | |
|---|---|---|---|---|---|---|---|---|---|---|---|
| gat | att | tgc | agg | ccc | cac | cag | atc | tgt | aac | gtg | gtg | gcc | atc | cct | ggg | 576 |
| Asp | Ile | Cys | Arg | Pro | His | Gln | Ile | Cys | Asn | Val | Val | Ala | Ile | Pro | Gly | |
| | | | 180 | | | | | 185 | | | | | 190 | | | |

| | | | | | | | | | | | |
|---|---|---|---|---|---|---|---|---|---|---|---|
| aat | gca | agc | atg | gat | gca | aac | tgc | acg | tcc | ccg | gag | ccc | aac | agc | aca | 624 |
| Asn | Ala | Ser | Met | Asp | Ala | Asn | Cys | Thr | Ser | Pro | Glu | Pro | Asn | Ser | Thr | |
| | | 195 | | | | | 200 | | | | | 205 | | | | |

| | | | | | | | | | | | |
|---|---|---|---|---|---|---|---|---|---|---|---|
| tgc | cgg | ctc | aga | gaa | tac | tat | gac | cag | aca | gct | cag | atg | tgc | tgc | agc | 672 |
| Cys | Arg | Leu | Arg | Glu | Tyr | Tyr | Asp | Gln | Thr | Ala | Gln | Met | Cys | Cys | Ser | |
| | 210 | | | | | 215 | | | | | 220 | | | | | |

| | | | | | | | | | | | |
|---|---|---|---|---|---|---|---|---|---|---|---|
| aaa | tgc | tcg | ccg | ggc | caa | cat | gca | aaa | gtc | ttc | tgt | acc | aag | acc | tcg | 720 |
| Lys | Cys | Ser | Pro | Gly | Gln | His | Ala | Lys | Val | Phe | Cys | Thr | Lys | Thr | Ser | |
| 225 | | | | 230 | | | | | 235 | | | | | 240 | | |

-continued

| | | |
|---|---|---|
| gac acc gtg tgt gac tcc tgt gag gac agc aca tac acc cag ctc tgg<br>Asp Thr Val Cys Asp Ser Cys Glu Asp Ser Thr Tyr Thr Gln Leu Trp<br>                245                      250                    255 | 768 |
| aac tgg gtt ccc gag tgc ttg agc tgt ggc tcc cgc tgt agc tct gac<br>Asn Trp Val Pro Glu Cys Leu Ser Cys Gly Ser Arg Cys Ser Ser Asp<br>                260                      265                    270 | 816 |
| cag gtg gaa act caa gcc tgc act cgg gaa cag aac cgc atc tgc acc<br>Gln Val Glu Thr Gln Ala Cys Thr Arg Glu Gln Asn Arg Ile Cys Thr<br>275                      280                      285 | 864 |
| tgc agg ccc ggc tgg tac tgc gcg ctg agc aag cag gag ggg tgc cgg<br>Cys Arg Pro Gly Trp Tyr Cys Ala Leu Ser Lys Gln Glu Gly Cys Arg<br>                290                      295                    300 | 912 |
| ctg tgc gcg ccg ctg cgc aag tgc cgc ccg ggc ttc ggc gtg gcc aga<br>Leu Cys Ala Pro Leu Arg Lys Cys Arg Pro Gly Phe Gly Val Ala Arg<br>305                      310                      315                    320 | 960 |
| cca gga act gaa aca tca gac gtg gtg tgc aag ccc tgt gcc ccg ggg<br>Pro Gly Thr Glu Thr Ser Asp Val Val Cys Lys Pro Cys Ala Pro Gly<br>                      325                      330                    335 | 1008 |
| acg ttc tcc aac acg act tca tcc acg gat att tgc agg ccc cac cag<br>Thr Phe Ser Asn Thr Thr Ser Ser Thr Asp Ile Cys Arg Pro His Gln<br>                340                      345                    350 | 1056 |
| atc tgt aac gtg gtg gcc atc cct ggg aat gca agc atg gat gca gtc<br>Ile Cys Asn Val Val Ala Ile Pro Gly Asn Ala Ser Met Asp Ala Val<br>                355                      360                    365 | 1104 |
| tgc acg tcc acg tcc ccc acc cgg agt atg gcc cca ggg gca gta cac<br>Cys Thr Ser Thr Ser Pro Thr Arg Ser Met Ala Pro Gly Ala Val His<br>                370                      375                    380 | 1152 |
| tta ccc cag cca gtg tcc aca cga tcc caa cac acg cag cca act cca<br>Leu Pro Gln Pro Val Ser Thr Arg Ser Gln His Thr Gln Pro Thr Pro<br>385                      390                      395                    400 | 1200 |
| gaa ccc agc act gct cca agc acc tcc ttc ctg ctc cca atg ggc ccc<br>Glu Pro Ser Thr Ala Pro Ser Thr Ser Phe Leu Leu Pro Met Gly Pro<br>                      405                      410                    415 | 1248 |
| agc ccc cca gct gaa ggg agc act ggc gac gca gag ccc aaa tct tgt<br>Ser Pro Pro Ala Glu Gly Ser Thr Gly Asp Ala Glu Pro Lys Ser Cys<br>                420                      425                    430 | 1296 |
| gac aaa act cac aca tgc cca ccg tgc cca gca cct gaa ctc ctg ggg<br>Asp Lys Thr His Thr Cys Pro Pro Cys Pro Ala Pro Glu Leu Leu Gly<br>                435                      440                    445 | 1344 |
| gga ccg tca gtc ttc ctc ttc ccc cca aaa ccc aag gac acc ctc atg<br>Gly Pro Ser Val Phe Leu Phe Pro Pro Lys Pro Lys Asp Thr Leu Met<br>450                      455                      460 | 1392 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>465                      470                      475                    480 | 1440 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>                      485                      490                    495 | 1488 |
| cat aat gcc aag aca aag ccg cgg gag gag cag tac aac agc acg tac<br>His Asn Ala Lys Thr Lys Pro Arg Glu Glu Gln Tyr Asn Ser Thr Tyr<br>                500                      505                    510 | 1536 |
| cgg gtg gtc agc gtc ctc acc gtc ctg cac cag gac tgg ctg aat ggc<br>Arg Val Val Ser Val Leu Thr Val Leu His Gln Asp Trp Leu Asn Gly<br>                515                      520                    525 | 1584 |
| aag gag tac aag tgc aag gtc tcc aac aaa gcc ctc cca gcc ccc atc<br>Lys Glu Tyr Lys Cys Lys Val Ser Asn Lys Ala Leu Pro Ala Pro Ile<br>                530                      535                    540 | 1632 |
| gag aaa acc atc tcc aaa gcc aaa ggg cag ccc cga gaa cca cag gtg<br>Glu Lys Thr Ile Ser Lys Ala Lys Gly Gln Pro Arg Glu Pro Gln Val<br>545                      550                      555                    560 | 1680 |

|  |  |  |  |  |  |  |  |  |  |  |  |  |  |  |  |  |
|---|---|---|---|---|---|---|---|---|---|---|---|---|---|---|---|---|
| tac | acc | ctg | ccc | cca | tcc | cgg | gat | gag | ctg | acc | aag | aac | cag | gtc | agc | 1728 |
| Tyr | Thr | Leu | Pro | Pro | Ser | Arg | Asp | Glu | Leu | Thr | Lys | Asn | Gln | Val | Ser | |
|  |  |  | 565 |  |  |  |  | 570 |  |  |  |  | 575 |  |  | |
| ctg | acc | tgc | ctg | gtc | aaa | ggc | ttc | tat | ccc | agc | gac | atc | gcc | gtg | gag | 1776 |
| Leu | Thr | Cys | Leu | Val | Lys | Gly | Phe | Tyr | Pro | Ser | Asp | Ile | Ala | Val | Glu | |
|  |  | 580 |  |  |  |  | 585 |  |  |  |  | 590 |  |  |  | |
| tgg | gag | agc | aat | ggg | cag | ccg | gag | aac | aac | tac | aag | acc | acg | cct | ccc | 1824 |
| Trp | Glu | Ser | Asn | Gly | Gln | Pro | Glu | Asn | Asn | Tyr | Lys | Thr | Thr | Pro | Pro | |
|  | 595 |  |  |  |  | 600 |  |  |  |  | 605 |  |  |  |  | |
| gtg | ctg | gac | tcc | gac | ggc | tcc | ttc | ttc | ctc | tac | agc | aag | ctc | acc | gtg | 1872 |
| Val | Leu | Asp | Ser | Asp | Gly | Ser | Phe | Phe | Leu | Tyr | Ser | Lys | Leu | Thr | Val | |
| 610 |  |  |  |  | 615 |  |  |  |  | 620 |  |  |  |  |  | |
| gac | aag | agc | agg | tgg | cag | cag | ggg | aac | gtc | ttc | tca | tgc | tcc | gtg | atg | 1920 |
| Asp | Lys | Ser | Arg | Trp | Gln | Gln | Gly | Asn | Val | Phe | Ser | Cys | Ser | Val | Met | |
| 625 |  |  |  | 630 |  |  |  |  | 635 |  |  |  |  | 640 |  | |
| cat | gag | gct | ctg | cac | aac | cac | tac | acg | cag | aag | agc | ctc | tcc | ctg | tct | 1968 |
| His | Glu | Ala | Leu | His | Asn | His | Tyr | Thr | Gln | Lys | Ser | Leu | Ser | Leu | Ser | |
|  |  |  |  | 645 |  |  |  |  | 650 |  |  |  |  | 655 |  | |
| ccg | ggt | aaa |  | tga |  |  |  |  |  |  |  |  |  |  |  | 1980 |
| Pro | Gly | Lys |  |  |  |  |  |  |  |  |  |  |  |  |  | |

<210> SEQ ID NO 12
<211> LENGTH: 659
<212> TYPE: PRT
<213> ORGANISM: Homo sapiens

<400> SEQUENCE: 12

| Met | Ala | Pro | Val | Ala | Val | Trp | Ala | Ala | Leu | Ala | Val | Gly | Leu | Glu | Leu |
|---|---|---|---|---|---|---|---|---|---|---|---|---|---|---|---|
| 1 |  |  |  | 5 |  |  |  |  | 10 |  |  |  |  | 15 |  |

| Trp | Ala | Ala | Ala | His | Ala | Leu | Pro | Ala | Gln | Val | Ala | Phe | Thr | Pro | Tyr |
|---|---|---|---|---|---|---|---|---|---|---|---|---|---|---|---|
|  |  |  | 20 |  |  |  |  | 25 |  |  |  |  | 30 |  |  |

| Ala | Pro | Glu | Pro | Gly | Ser | Thr | Cys | Arg | Leu | Arg | Glu | Tyr | Tyr | Asp | Gln |
|---|---|---|---|---|---|---|---|---|---|---|---|---|---|---|---|
|  |  | 35 |  |  |  |  | 40 |  |  |  |  | 45 |  |  |  |

| Thr | Ala | Gln | Met | Cys | Cys | Ser | Lys | Cys | Ser | Pro | Gly | Gln | His | Ala | Lys |
|---|---|---|---|---|---|---|---|---|---|---|---|---|---|---|---|
|  | 50 |  |  |  |  | 55 |  |  |  |  | 60 |  |  |  |  |

| Val | Phe | Cys | Thr | Lys | Thr | Ser | Asp | Thr | Val | Cys | Asp | Ser | Cys | Glu | Asp |
|---|---|---|---|---|---|---|---|---|---|---|---|---|---|---|---|
| 65 |  |  |  |  | 70 |  |  |  |  | 75 |  |  |  |  | 80 |

| Ser | Thr | Tyr | Thr | Gln | Leu | Trp | Asn | Trp | Val | Pro | Glu | Cys | Leu | Ser | Cys |
|---|---|---|---|---|---|---|---|---|---|---|---|---|---|---|---|
|  |  |  |  | 85 |  |  |  |  | 90 |  |  |  |  | 95 |  |

| Gly | Ser | Arg | Cys | Ser | Ser | Asp | Gln | Val | Glu | Thr | Gln | Ala | Cys | Thr | Arg |
|---|---|---|---|---|---|---|---|---|---|---|---|---|---|---|---|
|  |  |  | 100 |  |  |  |  | 105 |  |  |  |  | 110 |  |  |

| Glu | Gln | Asn | Arg | Ile | Cys | Thr | Cys | Arg | Pro | Gly | Trp | Tyr | Cys | Ala | Leu |
|---|---|---|---|---|---|---|---|---|---|---|---|---|---|---|---|
|  |  | 115 |  |  |  |  | 120 |  |  |  |  | 125 |  |  |  |

| Ser | Lys | Gln | Glu | Gly | Cys | Arg | Leu | Cys | Ala | Pro | Leu | Arg | Lys | Cys | Arg |
|---|---|---|---|---|---|---|---|---|---|---|---|---|---|---|---|
|  | 130 |  |  |  |  | 135 |  |  |  |  | 140 |  |  |  |  |

| Pro | Gly | Phe | Gly | Val | Ala | Arg | Pro | Gly | Thr | Glu | Thr | Ser | Asp | Val | Val |
|---|---|---|---|---|---|---|---|---|---|---|---|---|---|---|---|
| 145 |  |  |  |  | 150 |  |  |  |  | 155 |  |  |  |  | 160 |

| Cys | Lys | Pro | Cys | Ala | Pro | Gly | Thr | Phe | Ser | Asn | Thr | Thr | Ser | Ser | Thr |
|---|---|---|---|---|---|---|---|---|---|---|---|---|---|---|---|
|  |  |  |  | 165 |  |  |  |  | 170 |  |  |  |  | 175 |  |

| Asp | Ile | Cys | Arg | Pro | His | Gln | Ile | Cys | Asn | Val | Val | Ala | Ile | Pro | Gly |
|---|---|---|---|---|---|---|---|---|---|---|---|---|---|---|---|
|  |  |  | 180 |  |  |  |  | 185 |  |  |  |  | 190 |  |  |

| Asn | Ala | Ser | Met | Asp | Ala | Asn | Cys | Thr | Ser | Pro | Glu | Pro | Asn | Ser | Thr |
|---|---|---|---|---|---|---|---|---|---|---|---|---|---|---|---|
|  |  | 195 |  |  |  |  | 200 |  |  |  |  | 205 |  |  |  |

| Cys | Arg | Leu | Arg | Glu | Tyr | Tyr | Asp | Gln | Thr | Ala | Gln | Met | Cys | Cys | Ser |
|---|---|---|---|---|---|---|---|---|---|---|---|---|---|---|---|
|  | 210 |  |  |  |  | 215 |  |  |  |  | 220 |  |  |  |  |

| Lys | Cys | Ser | Pro | Gly | Gln | His | Ala | Lys | Val | Phe | Cys | Thr | Lys | Thr | Ser |
|---|---|---|---|---|---|---|---|---|---|---|---|---|---|---|---|
| 225 |  |  |  |  | 230 |  |  |  |  | 235 |  |  |  |  | 240 |

-continued

```
Asp Thr Val Cys Asp Ser Cys Glu Asp Ser Thr Tyr Thr Gln Leu Trp
                245                 250                 255

Asn Trp Val Pro Glu Cys Leu Ser Cys Gly Ser Arg Cys Ser Ser Asp
            260                 265                 270

Gln Val Glu Thr Gln Ala Cys Thr Arg Glu Gln Asn Arg Ile Cys Thr
        275                 280                 285

Cys Arg Pro Gly Trp Tyr Cys Ala Leu Ser Lys Gln Glu Gly Cys Arg
    290                 295                 300

Leu Cys Ala Pro Leu Arg Lys Cys Arg Pro Gly Phe Gly Val Ala Arg
305                 310                 315                 320

Pro Gly Thr Glu Thr Ser Asp Val Val Cys Lys Pro Cys Ala Pro Gly
                325                 330                 335

Thr Phe Ser Asn Thr Thr Ser Ser Thr Asp Ile Cys Arg Pro His Gln
            340                 345                 350

Ile Cys Asn Val Val Ala Ile Pro Gly Asn Ala Ser Met Asp Ala Val
        355                 360                 365

Cys Thr Ser Thr Ser Pro Thr Arg Ser Met Ala Pro Gly Ala Val His
    370                 375                 380

Leu Pro Gln Pro Val Ser Thr Arg Ser Gln His Thr Gln Pro Thr Pro
385                 390                 395                 400

Glu Pro Ser Thr Ala Pro Ser Thr Ser Phe Leu Leu Pro Met Gly Pro
                405                 410                 415

Ser Pro Pro Ala Glu Gly Ser Thr Gly Asp Ala Glu Pro Lys Ser Cys
            420                 425                 430

Asp Lys Thr His Thr Cys Pro Pro Cys Pro Ala Pro Glu Leu Leu Gly
        435                 440                 445

Gly Pro Ser Val Phe Leu Phe Pro Pro Lys Pro Lys Asp Thr Leu Met
    450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Ala Leu Pro Ala Pro Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Asp Glu Leu Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
        595                 600                 605

Val Leu Asp Ser Asp Gly Ser Phe Phe Leu Tyr Ser Lys Leu Thr Val
    610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys
```

<210> SEQ ID NO 13
<211> LENGTH: 1314
<212> TYPE: DNA
<213> ORGANISM: Homo sapiens
<220> FEATURE:
<221> NAME/KEY: CDS
<222> LOCATION: (1)..(1311)
<223> OTHER INFORMATION: CD2-IgG
<220> FEATURE:
<221> NAME/KEY: C_region
<222> LOCATION: (613)..(1314)
<223> OTHER INFORMATION: Hinge, CH2, CH3 region
<220> FEATURE:
<221> NAME/KEY: misc_signal
<222> LOCATION: (265)..(273)
<223> OTHER INFORMATION: N-linked glycosylation site
<220> FEATURE:
<221> NAME/KEY: misc_signal
<222> LOCATION: (421)..(429)
<223> OTHER INFORMATION: N-linked glycosylation site
<220> FEATURE:
<221> NAME/KEY: misc_signal
<222> LOCATION: (448)..(456)
<223> OTHER INFORMATION: N-linked glycosylation site
<220> FEATURE:
<221> NAME/KEY: primer_bind
<222> LOCATION: (1)..(27)
<223> OTHER INFORMATION: PCR primer SEQ ID : 40 binding site
<220> FEATURE:
<221> NAME/KEY: primer_bind
<222> LOCATION: (589)..(618)
<223> OTHER INFORMATION: PCR primer SEQ ID : 41(antisense) binding site
<220> FEATURE:
<221> NAME/KEY: primer_bind
<222> LOCATION: (611)..(633)
<223> OTHER INFORMATION: PCR primer SEQ ID : 42 binding site
<220> FEATURE:
<221> NAME/KEY: primer_bind
<222> LOCATION: (1292)..(1314)
<223> OTHER INFORMATION: PCR primer SEQ ID : 28(antisense) binding site
<220> FEATURE:
<221> NAME/KEY: sig_peptide
<222> LOCATION: (1)..(72)
<223> OTHER INFORMATION: signal peptide

<400> SEQUENCE: 13

```
atg agc ttt cca tgt aaa ttt gta gcc agc ttc ctt ctg att ttc aat        48
Met Ser Phe Pro Cys Lys Phe Val Ala Ser Phe Leu Leu Ile Phe Asn
 1               5                  10                  15 gtt tct tcc aaa ggt gca gtc tcc aaa gag att acg aat gcc ttg gaa        96
Val Ser Ser Lys Gly Ala Val Ser Lys Glu Ile Thr Asn Ala Leu Glu
                20                  25                  30 acc tgg ggt gcc ttg ggt cag gac atc aac ttg gac att cct agt ttt       144
Thr Trp Gly Ala Leu Gly Gln Asp Ile Asn Leu Asp Ile Pro Ser Phe
            35                  40                  45 caa atg agt gat gat att gac gat ata aaa tgg gaa aaa act tca gac       192
Gln Met Ser Asp Asp Ile Asp Asp Ile Lys Trp Glu Lys Thr Ser Asp
        50                  55                  60 aag aaa aag att gca caa ttc aga aaa gag aaa gag act ttc aag gaa       240
Lys Lys Lys Ile Ala Gln Phe Arg Lys Glu Lys Glu Thr Phe Lys Glu
    65                  70                  75                  80 aaa gat aca tat aag cta ttt aaa aat gga act ctg aaa att aag cat       288
Lys Asp Thr Tyr Lys Leu Phe Lys Asn Gly Thr Leu Lys Ile Lys His
                85                  90                  95 ctg aag acc gat gat cag gat atc tac aag gta tca ata tat gat aca       336
Leu Lys Thr Asp Asp Gln Asp Ile Tyr Lys Val Ser Ile Tyr Asp Thr
               100                 105                 110 aaa gga aaa aat gtg ttg gaa aaa ata ttt gat ttg aag att caa gag       384
Lys Gly Lys Asn Val Leu Glu Lys Ile Phe Asp Leu Lys Ile Gln Glu
           115                 120                 125
```

```
agg gtc tca aaa cca aag atc tcc tgg act tgt atc aac aca acc ctg        432
Arg Val Ser Lys Pro Lys Ile Ser Trp Thr Cys Ile Asn Thr Thr Leu
    130             135                 140 acc tgt gag gta atg aat gga act gac ccc gaa tta aac ctg tat caa        480
Thr Cys Glu Val Met Asn Gly Thr Asp Pro Glu Leu Asn Leu Tyr Gln
145             150                 155                 160 gat ggg aaa cat cta aaa ctt tct cag agg gtc atc aca cac aag tgg        528
Asp Gly Lys His Leu Lys Leu Ser Gln Arg Val Ile Thr His Lys Trp
                165                 170                 175 acc acc agc ctg agt gca aaa ttc aag tgc aca gca ggg aac aaa gtc        576
Thr Thr Ser Leu Ser Ala Lys Phe Lys Cys Thr Ala Gly Asn Lys Val
            180                 185                 190 agc aag gaa tcc agt gtc gag cct gtc agc tgt cct gca gag ccc aaa        624
Ser Lys Glu Ser Ser Val Glu Pro Val Ser Cys Pro Ala Glu Pro Lys
        195                 200                 205 tct tgt gac aaa act cac aca tgc cca ccg tgc cca gca cct gaa ctc        672
Ser Cys Asp Lys Thr His Thr Cys Pro Pro Cys Pro Ala Pro Glu Leu
    210                 215                 220 ctg ggg gga ccg tca gtc ttc ctc ttc ccc cca aaa ccc aag gac acc        720
Leu Gly Gly Pro Ser Val Phe Leu Phe Pro Pro Lys Pro Lys Asp Thr
225             230                 235                 240 ctc atg atc tcc cgg acc cct gag gtc aca tgc gtg gtg gtg gac gtg        768
Leu Met Ile Ser Arg Thr Pro Glu Val Thr Cys Val Val Val Asp Val
                245                 250                 255 agc cac gaa gac cct gag gtc aag ttc aac tgg tac gtg gac ggc gtg        816
Ser His Glu Asp Pro Glu Val Lys Phe Asn Trp Tyr Val Asp Gly Val
                260                 265                 270 gag gtg cat aat gcc aag aca aag ccg cgg gag gag cag tac aac agc        864
Glu Val His Asn Ala Lys Thr Lys Pro Arg Glu Glu Gln Tyr Asn Ser
            275                 280                 285 acg tac cgg gtg gtc agc gtc ctc acc gtc ctg cac cag gac tgg ctg        912
Thr Tyr Arg Val Val Ser Val Leu Thr Val Leu His Gln Asp Trp Leu
        290                 295                 300 aat ggc aag gag tac aag tgc aag gtc tcc aac aaa gcc ctc cca gcc        960
Asn Gly Lys Glu Tyr Lys Cys Lys Val Ser Asn Lys Ala Leu Pro Ala
305             310                 315                 320 ccc atc gag aaa acc atc tcc aaa gcc aaa ggg cag ccc cga gaa cca       1008
Pro Ile Glu Lys Thr Ile Ser Lys Ala Lys Gly Gln Pro Arg Glu Pro
                325                 330                 335 cag gtg tac acc ctg ccc cca tcc cgg gat gag ctg acc aag aac cag       1056
Gln Val Tyr Thr Leu Pro Pro Ser Arg Asp Glu Leu Thr Lys Asn Gln
                340                 345                 350 gtc agc ctg acc tgc ctg gtc aaa ggc ttc tat ccc agc gac atc gcc       1104
Val Ser Leu Thr Cys Leu Val Lys Gly Phe Tyr Pro Ser Asp Ile Ala
            355                 360                 365 gtg gag tgg gag agc aat ggg cag ccg gag aac aac tac aag acc acg       1152
Val Glu Trp Glu Ser Asn Gly Gln Pro Glu Asn Asn Tyr Lys Thr Thr
        370                 375                 380 cct ccc gtg ctg gac tcc gac ggc tcc ttc ttc ctc tac agc aag ctc       1200
Pro Pro Val Leu Asp Ser Asp Gly Ser Phe Phe Leu Tyr Ser Lys Leu
385             390                 395                 400 acc gtg gac aag agc agg tgg cag cag ggg aac gtc ttc tca tgc tcc       1248
Thr Val Asp Lys Ser Arg Trp Gln Gln Gly Asn Val Phe Ser Cys Ser
                405                 410                 415 gtg atg cat gag gct ctg cac aac cac tac acg cag aag agc ctc tcc       1296
Val Met His Glu Ala Leu His Asn His Tyr Thr Gln Lys Ser Leu Ser
                420                 425                 430 ctg tct ccg ggt aaa     tga                                           1314
Leu Ser Pro Gly Lys
                435
```

<210> SEQ ID NO 14
<211> LENGTH: 437
<212> TYPE: PRT
<213> ORGANISM: Homo sapiens

<400> SEQUENCE: 14

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Ala Glu Pro Lys
        195                 200                 205

Ser Cys Asp Lys Thr His Thr Cys Pro Pro Cys Pro Ala Pro Glu Leu
210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Asp Glu Leu Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
370                 375                 380

```
Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
            405                 410                 415

Val Met His Glu Ala Leu His Asn His Tyr Thr Gln Lys Ser Leu Ser
        420                 425                 430

Leu Ser Pro Gly Lys
        435

<210> SEQ ID NO 15
<211> LENGTH: 1134
<212> TYPE: DNA
<213> ORGANISM: Homo sapiens
<220> FEATURE:
<221> NAME/KEY: CDS
<222> LOCATION: (1)..(1131)
<223> OTHER INFORMATION: CTLA4-IgG
<220> FEATURE:
<221> NAME/KEY: C_region
<222> LOCATION: (433)..(1134)
<223> OTHER INFORMATION: Hinge, CH2, CH3 region
<220> FEATURE:
<221> NAME/KEY: misc_signal
<222> LOCATION: (289)..(297)
<223> OTHER INFORMATION: N-linked glycosylation site
<220> FEATURE:
<221> NAME/KEY: misc_signal
<222> LOCATION: (385)..(393)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 43 binding site
<220> FEATURE:
<221> NAME/KEY: primer_bind
<222> LOCATION: (409)..(438)
<223> OTHER INFORMATION: PCR primer SEQ ID : 44(antisense) binding site
<220> FEATURE:
<221> NAME/KEY: primer_bind
<222> LOCATION: (430)..(453)
<223> OTHER INFORMATION: PCR primer SEQ ID : 42 binding site
<220> FEATURE:
<221> NAME/KEY: primer_bind
<222> LOCATION: (1111)..(1134)
<223> OTHER INFORMATION: PCR primer SEQ ID : 28(antisense) binding site
<220> FEATURE:
<221> NAME/KEY: sig_peptide
<222> LOCATION: (1)..(63)
<223> OTHER INFORMATION: signal peptide

<400> SEQUENCE: 15 atg agg acc tgg ccc tgc act ctc ctg ttt ttt ctt ctc ttc atc cct      48
Met Arg Thr Trp Pro Cys Thr Leu Leu Phe Phe Leu Leu Phe Ile Pro
1               5                   10                  15 gtc ttc tgc aaa gca atg cac gtg gcc cag cct gct gtg gta ctg gcc     96
Val Phe Cys Lys Ala Met His Val Ala Gln Pro Ala Val Val Leu Ala
            20                  25                  30 agc agc cga ggc atc gcc agc ttt gtg tgt gag tat gca tct cca ggc    144
Ser Ser Arg Gly Ile Ala Ser Phe Val Cys Glu Tyr Ala Ser Pro Gly
        35                  40                  45 aaa gcc act gag gtc cgg gtg aca gtg ctt cgg cag gct gac agc cag    192
Lys Ala Thr Glu Val Arg Val Thr Val Leu Arg Gln Ala Asp Ser Gln
    50                  55                  60 gtg act gaa gtc tgt gcg gca acc tac atg atg ggg aat gag ttg acc    240
Val Thr Glu Val Cys Ala Ala Thr Tyr Met Met Gly Asn Glu Leu Thr
65                  70                  75                  80 ttc cta gat gat tcc atc tgc acg ggc acc tcc agt gga aat caa gtg    288
Phe Leu Asp Asp Ser Ile Cys Thr Gly Thr Ser Ser Gly Asn Gln Val
                85                  90                  95
```

```
aac ctc act atc caa gga ctg agg gcc atg gac acg gga ctc tac atc      336
Asn Leu Thr Ile Gln Gly Leu Arg Ala Met Asp Thr Gly Leu Tyr Ile
        100                 105                 110 tgc aag gtg gag ctc atg tac cca ccg cca tac tac ctg ggc ata ggc      384
Cys Lys Val Glu Leu Met Tyr Pro Pro Pro Tyr Tyr Leu Gly Ile Gly
    115                 120                 125 aac gga acc cag att tat gta att gat cca gaa ccg tgc cca gat tct      432
Asn Gly Thr Gln Ile Tyr Val Ile Asp Pro Glu Pro Cys Pro Asp Ser
130                 135                 140 gca gag ccc aaa tct tgt gac aaa act cac aca tgc cca ccg tgc cca      480
Ala Glu Pro Lys Ser Cys Asp Lys Thr His Thr Cys Pro Pro Cys Pro
145                 150                 155                 160 gca cct gaa ctc ctg ggg gga ccg tca gtc ttc ctc ttc ccc cca aaa      528
Ala Pro Glu Leu Leu Gly Gly Pro Ser Val Phe Leu Phe Pro Pro Lys
                165                 170                 175 ccc aag gac acc ctc atg atc tcc cgg acc cct gag gtc aca tgc gtg      576
Pro Lys Asp Thr Leu Met Ile Ser Arg Thr Pro Glu Val Thr Cys Val
                180                 185                 190 gtg gtg gac gtg agc cac gaa gac cct gag gtc aag ttc aac tgg tac      624
Val Val Asp Val Ser His Glu Asp Pro Glu Val Lys Phe Asn Trp Tyr
            195                 200                 205 gtg gac ggc gtg gag gtg cat aat gcc aag aca aag ccg cgg gag gag      672
Val Asp Gly Val Glu Val His Asn Ala Lys Thr Lys Pro Arg Glu Glu
210                 215                 220 cag tac aac agc acg tac cgg gtg gtc agc gtc ctc acc gtc ctg cac      720
Gln Tyr Asn Ser Thr Tyr Arg Val Val Ser Val Leu Thr Val Leu His
225                 230                 235                 240 cag gac tgg ctg aat ggc aag gag tac aag tgc aag gtc tcc aac aaa      768
Gln Asp Trp Leu Asn Gly Lys Glu Tyr Lys Cys Lys Val Ser Asn Lys
                245                 250                 255 gcc ctc cca gcc ccc atc gag aaa acc atc tcc aaa gcc aaa ggg cag      816
Ala Leu Pro Ala Pro Ile Glu Lys Thr Ile Ser Lys Ala Lys Gly Gln
                260                 265                 270 ccc cga gaa cca cag gtg tac acc ctg ccc cca tcc cgg gat gag ctg      864
Pro Arg Glu Pro Gln Val Tyr Thr Leu Pro Pro Ser Arg Asp Glu Leu
            275                 280                 285 acc aag aac cag gtc agc ctg acc tgc ctg gtc aaa ggc ttc tat ccc      912
Thr Lys Asn Gln Val Ser Leu Thr Cys Leu Val Lys Gly Phe Tyr Pro
290                 295                 300 agc gac atc gcc gtg gag tgg gag agc aat ggg cag ccg gag aac aac      960
Ser Asp Ile Ala Val Glu Trp Glu Ser Asn Gly Gln Pro Glu Asn Asn
305                 310                 315                 320 tac aag acc acg cct ccc gtg ctg gac tcc gac ggc tcc ttc ttc ctc     1008
Tyr Lys Thr Thr Pro Pro Val Leu Asp Ser Asp Gly Ser Phe Phe Leu
                325                 330                 335 tac agc aag ctc acc gtg gac aag agc agg tgg cag cag ggg aac gtc     1056
Tyr Ser Lys Leu Thr Val Asp Lys Ser Arg Trp Gln Gln Gly Asn Val
                340                 345                 350 ttc tca tgc tcc gtg atg cat gag gct ctg cac aac cac tac acg cag     1104
Phe Ser Cys Ser Val Met His Glu Ala Leu His Asn His Tyr Thr Gln
            355                 360                 365 aag agc ctc tcc ctg tct ccg ggt aaa           tga                   1134
Lys Ser Leu Ser Leu Ser Pro Gly Lys
370                 375
```

<210> SEQ ID NO 16
<211> LENGTH: 377
<212> TYPE: PRT
<213> ORGANISM: Homo sapiens

<400> SEQUENCE: 16

```
Met Arg Thr Trp Pro Cys Thr Leu Leu Phe Phe Leu Leu Phe Ile Pro
 1               5                  10                  15

Val Phe Cys Lys Ala Met His Val Ala Gln Pro Ala Val Val Leu Ala
             20                  25                  30

Ser Ser Arg Gly Ile Ala Ser Phe Val Cys Glu Tyr Ala Ser Pro Gly
         35                  40                  45

Lys Ala Thr Glu Val Arg Val Thr Val Leu Arg Gln Ala Asp Ser Gln
     50                  55                  60

Val Thr Glu Val Cys Ala Ala Thr Tyr Met Met Gly Asn Glu Leu Thr
 65                  70                  75                  80

Phe Leu Asp Asp Ser Ile Cys Thr Gly Thr Ser Ser Gly Asn Gln Val
                 85                  90                  95

Asn Leu Thr Ile Gln Gly Leu Arg Ala Met Asp Thr Gly Leu Tyr Ile
             100                 105                 110

Cys Lys Val Glu Leu Met Tyr Pro Pro Pro Tyr Leu Gly Ile Gly
         115                 120                 125

Asn Gly Thr Gln Ile Tyr Val Ile Asp Pro Glu Pro Cys Pro Asp Ser
    130                 135                 140

Ala Glu Pro Lys Ser Cys Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys
    370                 375
```

<210> SEQ ID NO 17
<211> LENGTH: 1854
<212> TYPE: DNA
<213> ORGANISM: Homo sapiens

```
<220> FEATURE:
<221> NAME/KEY: CDS
<222> LOCATION: (1)..(1851)
<223> OTHER INFORMATION: CD2-CD2-IgG
<220> FEATURE:
<221> NAME/KEY: C_region
<222> LOCATION: (1153)..(1854)
<223> OTHER INFORMATION: Hinge, CH2, CH3 region
<220> FEATURE:
<221> NAME/KEY: misc_signal
<222> LOCATION: (265)..(273)
<223> OTHER INFORMATION: N-linked glycosylation site
<220> FEATURE:
<221> NAME/KEY: misc_signal
<222> LOCATION: (421)..(429)
<223> OTHER INFORMATION: N-linked glycosylation site
<220> FEATURE:
<221> NAME/KEY: misc_signal
<222> LOCATION: (448)..(456)
<223> OTHER INFORMATION: N-linked glycosylation site
<220> FEATURE:
<221> NAME/KEY: misc_signal
<222> LOCATION: (805)..(813)
<223> OTHER INFORMATION: N-linked glycosylation site
<220> FEATURE:
<221> NAME/KEY: misc_signal
<222> LOCATION: (961)..(969)
<223> OTHER INFORMATION: N-linked glycosylation site
<220> FEATURE:
<221> NAME/KEY: misc_signal
<222> LOCATION: (988)..(996)
<223> OTHER INFORMATION: N-linked glycosylation site
<220> FEATURE:
<221> NAME/KEY: primer_bind
<222> LOCATION: (1)..(27)
<223> OTHER INFORMATION: PCR primer SEQ ID : 40 binding site
<220> FEATURE:
<221> NAME/KEY: primer_bind
<222> LOCATION: (598)..(612)
<223> OTHER INFORMATION: PCR primer SEQ ID : 46(antisense) binding site
<220> FEATURE:
<221> NAME/KEY: primer_bind
<222> LOCATION: (612)..(630)
<223> OTHER INFORMATION: PCR primer SEQ ID : 45 binding site
<220> FEATURE:
<221> NAME/KEY: primer_bind
<222> LOCATION: (1128)..(1158)
<223> OTHER INFORMATION: PCR primer SEQ ID : 41(antisense) binding site
<220> FEATURE:
<221> NAME/KEY: primer_bind
<222> LOCATION: (1151)..(1173)
<223> OTHER INFORMATION: PCR primer SEQ ID : 42 binding site
<220> FEATURE:
<221> NAME/KEY: primer_bind
<222> LOCATION: (1832)..(1854)
<223> OTHER INFORMATION: PCR primer SEQ ID : 28(antisense) binding site
<220> FEATURE:
<221> NAME/KEY: sig_peptide
<222> LOCATION: (1)..(72)
<223> OTHER INFORMATION: signal peptide

<400> SEQUENCE: 17 atg agc ttt cca tgt aaa ttt gta gcc agc ttc ctt ctg att ttc aat        48
Met Ser Phe Pro Cys Lys Phe Val Ala Ser Phe Leu Leu Ile Phe Asn
 1               5                  10                  15 gtt tct tcc aaa ggt gca gtc tcc aaa gag att acg aat gcc ttg gaa        96
Val Ser Ser Lys Gly Ala Val Ser Lys Glu Ile Thr Asn Ala Leu Glu
             20                  25                  30 acc tgg ggt gcc ttg ggt cag gac atc aac ttg gac att cct agt ttt       144
Thr Trp Gly Ala Leu Gly Gln Asp Ile Asn Leu Asp Ile Pro Ser Phe
         35                  40                  45 caa atg agt gat gat att gac gat ata aaa tgg gaa aaa act tca gac       192
Gln Met Ser Asp Asp Ile Asp Asp Ile Lys Trp Glu Lys Thr Ser Asp
     50                  55                  60
```

-continued

| | | |
|---|---|---|
| aag aaa aag att gca caa ttc aga aaa gag aaa gag act ttc aag gaa<br>Lys Lys Lys Ile Ala Gln Phe Arg Lys Glu Lys Glu Thr Phe Lys Glu<br>65                           70                       75                    80 | 240 |
| aaa gat aca tat aag cta ttt aaa aat gga act ctg aaa att aag cat<br>Lys Asp Thr Tyr Lys Leu Phe Lys Asn Gly Thr Leu Lys Ile Lys His<br>                     85                       90                       95 | 288 |
| ctg aag acc gat gat cag gat atc tac aag gta tca ata tat gat aca<br>Leu Lys Thr Asp Asp Gln Asp Ile Tyr Lys Val Ser Ile Tyr Asp Thr<br>                 100                   105                 110 | 336 |
| aaa gga aaa aat gtg ttg gaa aaa ata ttt gat ttg aag att caa gag<br>Lys Gly Lys Asn Val Leu Glu Lys Ile Phe Asp Leu Lys Ile Gln Glu<br>             115                   120                 125 | 384 |
| agg gtc tca aaa cca aag atc tcc tgg act tgt atc aac aca acc ctg<br>Arg Val Ser Lys Pro Lys Ile Ser Trp Thr Cys Ile Asn Thr Thr Leu<br>130                       135                   140 | 432 |
| acc tgt gag gta atg aat gga act gac ccc gaa tta aac ctg tat caa<br>Thr Cys Glu Val Met Asn Gly Thr Asp Pro Glu Leu Asn Leu Tyr Gln<br>145                       150                   155                160 | 480 |
| gat ggg aaa cat cta aaa ctt tct cag agg gtc atc aca cac aag tgg<br>Asp Gly Lys His Leu Lys Leu Ser Gln Arg Val Ile Thr His Lys Trp<br>                 165                   170                 175 | 528 |
| acc acc agc ctg agt gca aaa ttc aag tgc aca gca ggg aac aaa gtc<br>Thr Thr Ser Leu Ser Ala Lys Phe Lys Cys Thr Ala Gly Asn Lys Val<br>             180                   185                 190 | 576 |
| agc aag gaa tcc agt gtc gag cct gtc agc tgt cct aaa gag att acg<br>Ser Lys Glu Ser Ser Val Glu Pro Val Ser Cys Pro Lys Glu Ile Thr<br>             195                   200                 205 | 624 |
| aat gcc ttg gaa acc tgg ggt gcc ttg ggt cag gac atc aac ttg gac<br>Asn Ala Leu Glu Thr Trp Gly Ala Leu Gly Gln Asp Ile Asn Leu Asp<br>210                       215                   220 | 672 |
| att cct agt ttt caa atg agt gat gat att gac gat ata aaa tgg gaa<br>Ile Pro Ser Phe Gln Met Ser Asp Asp Ile Asp Asp Ile Lys Trp Glu<br>225                       230                   235                240 | 720 |
| aaa act tca gac aag aaa aag att gca caa ttc aga aaa gag aaa gag<br>Lys Thr Ser Asp Lys Lys Lys Ile Ala Gln Phe Arg Lys Glu Lys Glu<br>                 245                   250                 255 | 768 |
| act ttc aag gaa aaa gat aca tat aag cta ttt aaa aat gga act ctg<br>Thr Phe Lys Glu Lys Asp Thr Tyr Lys Leu Phe Lys Asn Gly Thr Leu<br>             260                   265                 270 | 816 |
| aaa att aag cat ctg aag acc gat gat cag gat atc tac aag gta tca<br>Lys Ile Lys His Leu Lys Thr Asp Asp Gln Asp Ile Tyr Lys Val Ser<br>             275                   280                 285 | 864 |
| ata tat gat aca aaa gga aaa aat gtg ttg gaa aaa ata ttt gat ttg<br>Ile Tyr Asp Thr Lys Gly Lys Asn Val Leu Glu Lys Ile Phe Asp Leu<br>290                       295                   300 | 912 |
| aag att caa gag agg gtc tca aaa cca aag atc tcc tgg act tgt atc<br>Lys Ile Gln Glu Arg Val Ser Lys Pro Lys Ile Ser Trp Thr Cys Ile<br>305                       310                   315                320 | 960 |
| aac aca acc ctg acc tgt gag gta atg aat gga act gac ccc gaa tta<br>Asn Thr Thr Leu Thr Cys Glu Val Met Asn Gly Thr Asp Pro Glu Leu<br>                 325                   330                 335 | 1008 |
| aac ctg tat caa gat ggg aaa cat cta aaa ctt tct cag agg gtc atc<br>Asn Leu Tyr Gln Asp Gly Lys His Leu Lys Leu Ser Gln Arg Val Ile<br>             340                   345                 350 | 1056 |
| aca cac aag tgg acc acc agc ctg agt gca aaa ttc aag tgc aca gca<br>Thr His Lys Trp Thr Thr Ser Leu Ser Ala Lys Phe Lys Cys Thr Ala<br>             355                   360                 365 | 1104 |
| ggg aac aaa gtc agc aag gaa tcc agt gtc gag cct gtc agc tgt cct<br>Gly Asn Lys Val Ser Lys Glu Ser Ser Val Glu Pro Val Ser Cys Pro<br>370                       375                   380 | 1152 |

```
gca gag ccc aaa tct tgt gac aaa act cac aca tgc cca ccg tgc cca    1200
Ala Glu Pro Lys Ser Cys Asp Lys Thr His Thr Cys Pro Pro Cys Pro
385                 390                 395                 400 gca cct gaa ctc ctg ggg gga ccg tca gtc ttc ctc ttc ccc cca aaa    1248
Ala Pro Glu Leu Leu Gly Gly Pro Ser Val Phe Leu Phe Pro Pro Lys
            405                 410                 415 ccc aag gac acc ctc atg atc tcc cgg acc cct gag gtc aca tgc gtg    1296
Pro Lys Asp Thr Leu Met Ile Ser Arg Thr Pro Glu Val Thr Cys Val
        420                 425                 430 gtg gtg gac gtg agc cac gaa gac cct gag gtc aag ttc aac tgg tac    1344
Val Val Asp Val Ser His Glu Asp Pro Glu Val Lys Phe Asn Trp Tyr
    435                 440                 445 gtg gac ggc gtg gag gtg cat aat gcc aag aca aag ccg cgg gag gag    1392
Val Asp Gly Val Glu Val His Asn Ala Lys Thr Lys Pro Arg Glu Glu
450                 455                 460 cag tac aac agc acg tac cgg gtg gtc agc gtc ctc acc gtc tgt cac    1440
Gln Tyr Asn Ser Thr Tyr Arg Val Val Ser Val Leu Thr Val Cys His
465                 470                 475                 480 cag gac tgg ctg aat ggc aag gag tac aag tgc aag gtc tcc aac aaa    1488
Gln Asp Trp Leu Asn Gly Lys Glu Tyr Lys Cys Lys Val Ser Asn Lys
            485                 490                 495 gcc ctc cca gcc ccc atc gag aaa acc atc tcc aaa gcc aaa ggg cag    1536
Ala Leu Pro Ala Pro Ile Glu Lys Thr Ile Ser Lys Ala Lys Gly Gln
        500                 505                 510 ccc cga gaa cca cag gtg tac acc ctg ccc cca tcc cgg gat gag ctg    1584
Pro Arg Glu Pro Gln Val Tyr Thr Leu Pro Pro Ser Arg Asp Glu Leu
    515                 520                 525 acc aag aac cag gtc agc ctg acc tgc ctg gtc aaa ggc ttc tat ccc    1632
Thr Lys Asn Gln Val Ser Leu Thr Cys Leu Val Lys Gly Phe Tyr Pro
530                 535                 540 agc gac atc gcc gtg gag tgg gag agc aat ggg cag ccg gag aac aac    1680
Ser Asp Ile Ala Val Glu Trp Glu Ser Asn Gly Gln Pro Glu Asn Asn
545                 550                 555                 560 tac aag acc acg cct ccc gtg ctg gac tcc gac ggc tcc ttc ttc ctc    1728
Tyr Lys Thr Thr Pro Pro Val Leu Asp Ser Asp Gly Ser Phe Phe Leu
            565                 570                 575 tac agc aag ctc acc gtg gac aag agc agg tgg cag cag ggg aac gtc    1776
Tyr Ser Lys Leu Thr Val Asp Lys Ser Arg Trp Gln Gln Gly Asn Val
        580                 585                 590 ttc tca tgc tcc gtg atg cat gag gct ctg cac aac cac tac acg cag    1824
Phe Ser Cys Ser Val Met His Glu Ala Leu His Asn His Tyr Thr Gln
    595                 600                 605 aag agc ctc tcc ctg tct ccg ggt aaa           tga                  1854
Lys Ser Leu Ser Leu Ser Pro Gly Lys
610                 615

<210> SEQ ID NO 18
<211> LENGTH: 617
<212> TYPE: PRT
<213> ORGANISM: Homo sapiens

<400> SEQUENCE: 18

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60
```

```
Lys Lys Lys Ile Ala Gln Phe Arg Lys Glu Lys Glu Thr Phe Lys Glu
 65                  70                  75                  80

Lys Asp Thr Tyr Lys Leu Phe Lys Asn Gly Thr Leu Lys Ile Lys His
             85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
            115                 120                 125

Arg Val Ser Lys Pro Lys Ile Ser Trp Thr Cys Ile Asn Thr Thr Leu
130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Lys Glu Ile Thr
        195                 200                 205

Asn Ala Leu Glu Thr Trp Gly Ala Leu Gly Gln Asp Ile Asn Leu Asp
210                 215                 220

Ile Pro Ser Phe Gln Met Ser Asp Asp Ile Asp Asp Ile Lys Trp Glu
225                 230                 235                 240

Lys Thr Ser Asp Lys Lys Ile Ala Gln Phe Arg Lys Glu Lys Glu
            245                 250                 255

Thr Phe Lys Glu Lys Asp Thr Tyr Lys Leu Phe Lys Asn Gly Thr Leu
        260                 265                 270

Lys Ile Lys His Leu Lys Thr Asp Asp Gln Asp Ile Tyr Lys Val Ser
        275                 280                 285

Ile Tyr Asp Thr Lys Gly Lys Asn Val Leu Glu Lys Ile Phe Asp Leu
290                 295                 300

Lys Ile Gln Glu Arg Val Ser Lys Pro Lys Ile Ser Trp Thr Cys Ile
305                 310                 315                 320

Asn Thr Thr Leu Thr Cys Glu Val Met Asn Gly Thr Asp Pro Glu Leu
            325                 330                 335

Asn Leu Tyr Gln Asp Gly Lys His Leu Lys Leu Ser Gln Arg Val Ile
            340                 345                 350

Thr His Lys Trp Thr Thr Ser Leu Ser Ala Lys Phe Lys Cys Thr Ala
        355                 360                 365

Gly Asn Lys Val Ser Lys Glu Ser Ser Val Glu Pro Val Ser Cys Pro
    370                 375                 380

Ala Glu Pro Lys Ser Cys Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
        450                 455                 460

Gln Tyr Asn Ser Thr Tyr Arg Val Val Ser Val Leu Thr Val Cys His
465                 470                 475                 480
```

```
Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Asp Glu Leu
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615
```

<210> SEQ ID NO 19
<211> LENGTH: 1509
<212> TYPE: DNA
<213> ORGANISM: Homo sapiens
<220> FEATURE:
<221> NAME/KEY: CDS
<222> LOCATION: (1)..(1506)
<223> OTHER INFORMATION: CTLA4-CTLA4-IgG
<220> FEATURE:
<221> NAME/KEY: C_region
<222> LOCATION: (808)..(1509)
<223> OTHER INFORMATION: Hinge, CH2, CH3 region
<220> FEATURE:
<221> NAME/KEY: misc_signal
<222> LOCATION: (289)..(297)
<223> OTHER INFORMATION: N-linked glycosylation site
<220> FEATURE:
<221> NAME/KEY: misc_signal
<222> LOCATION: (385)..(393)
<223> OTHER INFORMATION: N-linked glycosylation site
<220> FEATURE:
<221> NAME/KEY: misc_signal
<222> LOCATION: (664)..(672)
<223> OTHER INFORMATION: N-linked glycosylation site
<220> FEATURE:
<221> NAME/KEY: misc_signal
<222> LOCATION: (760)..(768)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 43 binding site
<220> FEATURE:
<221> NAME/KEY: primer_bind
<222> LOCATION: (418)..(431)
<223> OTHER INFORMATION: PCR primer SEQ ID : 48(antisense) binding site
<220> FEATURE:
<221> NAME/KEY: primer_bind
<222> LOCATION: (432)..(453)
<223> OTHER INFORMATION: PCR primer SEQ ID : 47 binding site
<220> FEATURE:
<221> NAME/KEY: primer_bind
<222> LOCATION: (784)..(813)
<223> OTHER INFORMATION: PCR primer SEQ ID : 44(antisense) binding site
<220> FEATURE:
<221> NAME/KEY: primer_bind
<222> LOCATION: (805)..(826)
<223> OTHER INFORMATION: PCR primer SEQ ID : 42 binding site

```
<220> FEATURE:
<221> NAME/KEY: primer_bind
<222> LOCATION: (1486)..(1509)
<223> OTHER INFORMATION: PCR primer SEQ ID : 28(antisense) binding site
<220> FEATURE:
<221> NAME/KEY: sig_peptide
<222> LOCATION: (1)..(63)
<223> OTHER INFORMATION: signal peptide

<400> SEQUENCE: 19 atg agg acc tgg ccc tgc act ctc ctg ttt ttt ctt ctc ttc atc cct        48
Met Arg Thr Trp Pro Cys Thr Leu Leu Phe Phe Leu Leu Phe Ile Pro
 1               5                  10                  15 gtc ttc tgc aaa gca atg cac gtg gcc cag cct gct gta ctg gcc            96
Val Phe Cys Lys Ala Met His Val Ala Gln Pro Ala Val Leu Ala
             20                  25                  30 agc agc cga ggc atc gcc agc ttt gtg tgt gag tat gca tct cca ggc       144
Ser Ser Arg Gly Ile Ala Ser Phe Val Cys Glu Tyr Ala Ser Pro Gly
         35                  40                  45 aaa gcc act gag gtc cgg gtg aca gtg ctt cgg cag gct gac agc cag       192
Lys Ala Thr Glu Val Arg Val Thr Val Leu Arg Gln Ala Asp Ser Gln
 50                  55                  60 gtg act gaa gtc tgt gcg gca acc tac atg atg ggg aat gag ttg acc       240
Val Thr Glu Val Cys Ala Ala Thr Tyr Met Met Gly Asn Glu Leu Thr
 65                  70                  75                  80 ttc cta gat gat tcc atc tgc acg ggc acc tcc agt gga aat caa gtg       288
Phe Leu Asp Asp Ser Ile Cys Thr Gly Thr Ser Ser Gly Asn Gln Val
             85                  90                  95 aac ctc act atc caa gga ctg agg gcc atg gac acg gga ctc tac atc       336
Asn Leu Thr Ile Gln Gly Leu Arg Ala Met Asp Thr Gly Leu Tyr Ile
        100                 105                 110 tgc aag gtg gag ctc atg tac cca ccg cca tac tac ctg ggc ata ggc       384
Cys Lys Val Glu Leu Met Tyr Pro Pro Pro Tyr Tyr Leu Gly Ile Gly
        115                 120                 125 aac gga acc cag att tat gta att gat cca gaa ccg tgc cca gat tcg       432
Asn Gly Thr Gln Ile Tyr Val Ile Asp Pro Glu Pro Cys Pro Asp Ser
    130                 135                 140 gat aac atg cac gtg gcc cag cct gct gtg gta ctg gcc agc agc cga       480
Asp Asn Met His Val Ala Gln Pro Ala Val Val Leu Ala Ser Ser Arg
145                 150                 155                 160 ggc atc gcc agc ttt gtg tgt gag tat gca tct cca ggc aaa gcc act       528
Gly Ile Ala Ser Phe Val Cys Glu Tyr Ala Ser Pro Gly Lys Ala Thr
                165                 170                 175 gag gtc cgg gtg aca gtg ctt cgg cag gct gac agc cag gtg act gaa       576
Glu Val Arg Val Thr Val Leu Arg Gln Ala Asp Ser Gln Val Thr Glu
            180                 185                 190 gtc tgt gcg gca acc tac atg atg ggg aat gag ttg acc ttc cta gat       624
Val Cys Ala Ala Thr Tyr Met Met Gly Asn Glu Leu Thr Phe Leu Asp
        195                 200                 205 gat tcc atc tgc acg ggc acc tcc agt gga aat caa gtg aac ctc act       672
Asp Ser Ile Cys Thr Gly Thr Ser Ser Gly Asn Gln Val Asn Leu Thr
    210                 215                 220 atc caa gga ctg agg gcc atg gac acg gga ctc tac atc tgc aag gtg       720
Ile Gln Gly Leu Arg Ala Met Asp Thr Gly Leu Tyr Ile Cys Lys Val
225                 230                 235                 240 gag ctc atg tac cca ccg cca tac tac ctg ggc ata ggc aac gga acc       768
Glu Leu Met Tyr Pro Pro Pro Tyr Tyr Leu Gly Ile Gly Asn Gly Thr
                245                 250                 255 cag att tat gta att gat cca gaa ccg tgc cca gat tct gca gag ccc       816
Gln Ile Tyr Val Ile Asp Pro Glu Pro Cys Pro Asp Ser Ala Glu Pro
            260                 265                 270
```

```
aaa tct tgt gac aaa act cac aca tgc cca ccg tgc cca gca cct gaa      864
Lys Ser Cys Asp Lys Thr His Thr Cys Pro Pro Cys Pro Ala Pro Glu
            275                 280                 285 ctc ctg ggg gga ccg tca gtc ttc ctc ttc ccc cca aaa ccc aag gac      912
Leu Leu Gly Gly Pro Ser Val Phe Leu Phe Pro Pro Lys Pro Lys Asp
    290                 295                 300 acc ctc atg atc tcc cgg acc cct gag gtc aca tgc gtg gtg gtg gac      960
Thr Leu Met Ile Ser Arg Thr Pro Glu Val Thr Cys Val Val Val Asp
305                 310                 315                 320 gtg agc cac gaa gac cct gag gtc aag ttc aac tgg tac gtg gac ggc     1008
Val Ser His Glu Asp Pro Glu Val Lys Phe Asn Trp Tyr Val Asp Gly
                325                 330                 335 gtg gag gtg cat aat gcc aag aca aag ccg cgg gag gag cag tac aac     1056
Val Glu Val His Asn Ala Lys Thr Lys Pro Arg Glu Glu Gln Tyr Asn
            340                 345                 350 agc acg tac cgg gtg gtc agc gtc ctc acc gtc tgt cac cag gac tgg     1104
Ser Thr Tyr Arg Val Val Ser Val Leu Thr Val Cys His Gln Asp Trp
    355                 360                 365 ctg aat ggc aag gag tac aag tgc aag gtc tcc aac aaa gcc ctc cca     1152
Leu Asn Gly Lys Glu Tyr Lys Cys Lys Val Ser Asn Lys Ala Leu Pro
370                 375                 380 gcc ccc atc gag aaa acc atc tcc aaa gcc aaa ggg cag ccc cga gaa     1200
Ala Pro Ile Glu Lys Thr Ile Ser Lys Ala Lys Gly Gln Pro Arg Glu
385                 390                 395                 400 cca cag gtg tac acc ctg ccc cca tcc cgg gat gag ctg acc aag aac     1248
Pro Gln Val Tyr Thr Leu Pro Pro Ser Arg Asp Glu Leu Thr Lys Asn
                405                 410                 415 cag gtc agc ctg acc tgc ctg gtc aaa ggc ttc tat ccc agc gac atc     1296
Gln Val Ser Leu Thr Cys Leu Val Lys Gly Phe Tyr Pro Ser Asp Ile
            420                 425                 430 gcc gtg gag tgg gag agc aat ggg cag ccg gag aac aac tac aag acc     1344
Ala Val Glu Trp Glu Ser Asn Gly Gln Pro Glu Asn Asn Tyr Lys Thr
    435                 440                 445 acg cct ccc gtg ctg gac tcc gac ggc tcc ttc ttc ctc tac agc aag     1392
Thr Pro Pro Val Leu Asp Ser Asp Gly Ser Phe Phe Leu Tyr Ser Lys
450                 455                 460 ctc acc gtg gac aag agc agg tgg cag cag ggg aac gtc ttc tca tgc     1440
Leu Thr Val Asp Lys Ser Arg Trp Gln Gln Gly Asn Val Phe Ser Cys
465                 470                 475                 480 tcc gtg atg cat gag gct ctg cac aac cac tac acg cag aag agc ctc     1488
Ser Val Met His Glu Ala Leu His Asn His Tyr Thr Gln Lys Ser Leu
                485                 490                 495 tcc ctg tct ccg ggt aaa     tga                                      1509
Ser Leu Ser Pro Gly Lys
            500
```

<210> SEQ ID NO 20
<211> LENGTH: 502
<212> TYPE: PRT
<213> ORGANISM: Homo sapiens

<400> SEQUENCE: 20

```
Met Arg Thr Trp Pro Cys Thr Leu Leu Phe Phe Leu Leu Phe Ile Pro
1               5                   10                  15

Val Phe Cys Lys Ala Met His Val Ala Gln Pro Ala Val Val Leu Ala
            20                  25                  30

Ser Ser Arg Gly Ile Ala Ser Phe Val Cys Glu Tyr Ala Ser Pro Gly
        35                  40                  45

Lys Ala Thr Glu Val Arg Val Thr Val Leu Arg Gln Ala Asp Ser Gln
    50                  55                  60
```

```
Val Thr Glu Val Cys Ala Ala Thr Tyr Met Met Gly Asn Glu Leu Thr
 65                  70                  75                  80

Phe Leu Asp Asp Ser Ile Cys Thr Gly Thr Ser Ser Gly Asn Gln Val
             85                  90                  95

Asn Leu Thr Ile Gln Gly Leu Arg Ala Met Asp Thr Gly Leu Tyr Ile
            100                 105                 110

Cys Lys Val Glu Leu Met Tyr Pro Pro Pro Tyr Leu Gly Ile Gly
            115                 120                 125

Asn Gly Thr Gln Ile Tyr Val Ile Asp Pro Glu Pro Cys Pro Asp Ser
130                 135                 140

Asp Asn Met His Val Ala Gln Pro Ala Val Val Leu Ala Ser Ser Arg
145                 150                 155                 160

Gly Ile Ala Ser Phe Val Cys Glu Tyr Ala Ser Pro Gly Lys Ala Thr
                165                 170                 175

Glu Val Arg Val Thr Val Leu Arg Gln Ala Asp Ser Gln Val Thr Glu
            180                 185                 190

Val Cys Ala Ala Thr Tyr Met Met Gly Asn Glu Leu Thr Phe Leu Asp
            195                 200                 205

Asp Ser Ile Cys Thr Gly Thr Ser Ser Gly Asn Gln Val Asn Leu Thr
210                 215                 220

Ile Gln Gly Leu Arg Ala Met Asp Thr Gly Leu Tyr Ile Cys Lys Val
225                 230                 235                 240

Glu Leu Met Tyr Pro Pro Pro Tyr Leu Gly Ile Gly Asn Gly Thr
                245                 250                 255

Gln Ile Tyr Val Ile Asp Pro Glu Pro Cys Pro Asp Ser Ala Glu Pro
            260                 265                 270

Lys Ser Cys Asp Lys Thr His Thr Cys Pro Pro Cys Pro Ala Pro Glu
            275                 280                 285

Leu Leu Gly Gly Pro Ser Val Phe Leu Phe Pro Pro Lys Pro Lys Asp
            290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Cys His Gln Asp Trp
            355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Lys
            450                 455                 460

Leu Thr Val Asp Lys Ser Arg Trp Gln Gln Gly Asn Val Phe Ser Cys
465                 470                 475                 480
```

```
Ser Val Met His Glu Ala Leu His Asn His Tyr Thr Gln Lys Ser Leu
            485                 490                 495
Ser Leu Ser Pro Gly Lys
            500

<210> SEQ ID NO 21
<211> LENGTH: 1854
<212> TYPE: DNA
<213> ORGANISM: Homo sapiens
<220> FEATURE:
<221> NAME/KEY: CDS
<222> LOCATION: (1)..(1851)
<223> OTHER INFORMATION: mgCD2-CD2-IgG
<220> FEATURE:
<221> NAME/KEY: C_region
<222> LOCATION: (1153)..(1854)
<223> OTHER INFORMATION: Hinge, CH2, CH3 region
<220> FEATURE:
<221> NAME/KEY: misc_signal
<222> LOCATION: (265)..(273)
<223> OTHER INFORMATION: N-linked glycosylation site
<220> FEATURE:
<221> NAME/KEY: misc_signal
<222> LOCATION: (421)..(429)
<223> OTHER INFORMATION: N-linked glycosylation site
<220> FEATURE:
<221> NAME/KEY: misc_signal
<222> LOCATION: (448)..(456)
<223> OTHER INFORMATION: N-linked glycosylation site
<220> FEATURE:
<221> NAME/KEY: misc_signal
<222> LOCATION: (598)..(606)
<223> OTHER INFORMATION: N-linked glycosylation site
<220> FEATURE:
<221> NAME/KEY: misc_signal
<222> LOCATION: (616)..(624)
<223> OTHER INFORMATION: N-linked glycosylation site
<220> FEATURE:
<221> NAME/KEY: misc_signal
<222> LOCATION: (805)..(813)
<223> OTHER INFORMATION: N-linked glycosylation site
<220> FEATURE:
<221> NAME/KEY: misc_signal
<222> LOCATION: (961)..(969)
<223> OTHER INFORMATION: N-linked glycosylation site
<220> FEATURE:
<221> NAME/KEY: misc_signal
<222> LOCATION: (988)..(996)
<223> OTHER INFORMATION: N-linked glycosylation site
<220> FEATURE:
<221> NAME/KEY: primer_bind
<222> LOCATION: (1)..(27)
<223> OTHER INFORMATION: PCR primer SEQ ID : 40 binding site
<220> FEATURE:
<221> NAME/KEY: primer_bind
<222> LOCATION: (588)..(630)
<223> OTHER INFORMATION: PCR primer SEQ ID : 50(antisense) binding site
<220> FEATURE:
<221> NAME/KEY: primer_bind
<222> LOCATION: (588)..(630)
<223> OTHER INFORMATION: PCR primer SEQ ID : 49 binding site
<220> FEATURE:
<221> NAME/KEY: primer_bind
<222> LOCATION: (1128)..(1158)
<223> OTHER INFORMATION: PCR primer SEQ ID : 41(antisense) binding site
<220> FEATURE:
<221> NAME/KEY: primer_bind
<222> LOCATION: (1151)..(1173)
<223> OTHER INFORMATION: PCR primer SEQ ID : 42 binding site
<220> FEATURE:
<221> NAME/KEY: primer_bind
<222> LOCATION: (1832)..(1854)
<223> OTHER INFORMATION: PCR primer SEQ ID : 28(antisense) binding site
<220> FEATURE:
<221> NAME/KEY: sig_peptide
<222> LOCATION: (1)..(72)
<223> OTHER INFORMATION: signal peptide
```

<400> SEQUENCE: 21

```
atg agc ttt cca tgt aaa ttt gta gcc agc ttc ctt ctg att ttc aat      48
Met Ser Phe Pro Cys Lys Phe Val Ala Ser Phe Leu Leu Ile Phe Asn
 1               5                  10                  15 gtt tct tcc aaa ggt gca gtc tcc aaa gag att acg aat gcc ttg gaa      96
Val Ser Ser Lys Gly Ala Val Ser Lys Glu Ile Thr Asn Ala Leu Glu
             20                  25                  30 acc tgg ggt gcc ttg ggt cag gac atc aac ttg gac att cct agt ttt     144
Thr Trp Gly Ala Leu Gly Gln Asp Ile Asn Leu Asp Ile Pro Ser Phe
         35                  40                  45 caa atg agt gat gat att gac gat ata aaa tgg gaa aaa act tca gac     192
Gln Met Ser Asp Asp Ile Asp Asp Ile Lys Trp Glu Lys Thr Ser Asp
     50                  55                  60 aag aaa aag att gca caa ttc aga aaa gag aaa gag act ttc aag gaa     240
Lys Lys Lys Ile Ala Gln Phe Arg Lys Glu Lys Glu Thr Phe Lys Glu
 65                  70                  75                  80 aaa gat aca tat aag cta ttt aaa aat gga act ctg aaa att aag cat     288
Lys Asp Thr Tyr Lys Leu Phe Lys Asn Gly Thr Leu Lys Ile Lys His
                 85                  90                  95 ctg aag acc gat gat cag gat atc tac aag gta tca ata tat gat aca     336
Leu Lys Thr Asp Asp Gln Asp Ile Tyr Lys Val Ser Ile Tyr Asp Thr
            100                 105                 110 aaa gga aaa aat gtg ttg gaa aaa ata ttt gat ttg aag att caa gag     384
Lys Gly Lys Asn Val Leu Glu Lys Ile Phe Asp Leu Lys Ile Gln Glu
        115                 120                 125 agg gtc tca aaa cca aag atc tcc tgg act tgt atc aac aca acc ctg     432
Arg Val Ser Lys Pro Lys Ile Ser Trp Thr Cys Ile Asn Thr Thr Leu
    130                 135                 140 acc tgt gag gta atg aat gga act gac ccc gaa tta aac ctg tat caa     480
Thr Cys Glu Val Met Asn Gly Thr Asp Pro Glu Leu Asn Leu Tyr Gln
145                 150                 155                 160 gat ggg aaa cat cta aaa ctt tct cag agg gtc atc aca cac aag tgg     528
Asp Gly Lys His Leu Lys Leu Ser Gln Arg Val Ile Thr His Lys Trp
                165                 170                 175 acc acc agc ctg agt gca aaa ttc aag tgc aca gca ggg aac aaa gtc     576
Thr Thr Ser Leu Ser Ala Lys Phe Lys Cys Thr Ala Gly Asn Lys Val
            180                 185                 190 agc aag gaa tcc agt gtc gag aat gtc agc tgt cct aaa aat att acg     624
Ser Lys Glu Ser Ser Val Glu Asn Val Ser Cys Pro Lys Asn Ile Thr
        195                 200                 205 aat gcc ttg gaa acc tgg ggt gcc ttg ggt cag gac atc aac ttg gac     672
Asn Ala Leu Glu Thr Trp Gly Ala Leu Gly Gln Asp Ile Asn Leu Asp
    210                 215                 220 att cct agt ttt caa atg agt gat gat att gac gat ata aaa tgg gaa     720
Ile Pro Ser Phe Gln Met Ser Asp Asp Ile Asp Asp Ile Lys Trp Glu
225                 230                 235                 240 aaa act tca gac aag aaa aag att gca caa ttc aga aaa gag aaa gag     768
Lys Thr Ser Asp Lys Lys Lys Ile Ala Gln Phe Arg Lys Glu Lys Glu
                245                 250                 255 act ttc aag gaa aaa gat aca tat aag cta ttt aaa aat gga act ctg     816
Thr Phe Lys Glu Lys Asp Thr Tyr Lys Leu Phe Lys Asn Gly Thr Leu
            260                 265                 270 aaa att aag cat ctg aag acc gat gat cag gat atc tac aag gta tca     864
Lys Ile Lys His Leu Lys Thr Asp Asp Gln Asp Ile Tyr Lys Val Ser
        275                 280                 285 ata tat gat aca aaa gga aaa aat gtg ttg gaa aaa ata ttt gat ttg     912
Ile Tyr Asp Thr Lys Gly Lys Asn Val Leu Glu Lys Ile Phe Asp Leu
    290                 295                 300
```

```
aag att caa gag agg gtc tca aaa cca aag atc tcc tgg act tgt atc      960
Lys Ile Gln Glu Arg Val Ser Lys Pro Lys Ile Ser Trp Thr Cys Ile
305                 310                 315                 320 aac aca acc ctg acc tgt gag gta atg aat gga act gac ccc gaa tta     1008
Asn Thr Thr Leu Thr Cys Glu Val Met Asn Gly Thr Asp Pro Glu Leu
                325                 330                 335 aac ctg tat caa gat ggg aaa cat cta aaa ctt tct cag agg gtc atc     1056
Asn Leu Tyr Gln Asp Gly Lys His Leu Lys Leu Ser Gln Arg Val Ile
            340                 345                 350 aca cac aag tgg acc acc agc ctg agt gca aaa ttc aag tgc aca gca     1104
Thr His Lys Trp Thr Thr Ser Leu Ser Ala Lys Phe Lys Cys Thr Ala
        355                 360                 365 ggg aac aaa gtc agc aag gaa tcc agt gtc gag cct gtc agc tgt cct     1152
Gly Asn Lys Val Ser Lys Glu Ser Ser Val Glu Pro Val Ser Cys Pro
370                 375                 380 gca gag ccc aaa tct tgt gac aaa act cac aca tgc cca ccg tgc cca     1200
Ala Glu Pro Lys Ser Cys Asp Lys Thr His Thr Cys Pro Pro Cys Pro
385                 390                 395                 400 gca cct gaa ctc ctg ggg gga ccg tca gtc ttc ctc ttc ccc cca aaa     1248
Ala Pro Glu Leu Leu Gly Gly Pro Ser Val Phe Leu Phe Pro Pro Lys
                405                 410                 415 ccc aag gac acc ctc atg atc tcc cgg acc cct gag gtc aca tgc gtg     1296
Pro Lys Asp Thr Leu Met Ile Ser Arg Thr Pro Glu Val Thr Cys Val
            420                 425                 430 gtg gtg gac gtg agc cac gaa gac cct gag gtc aag ttc aac tgg tac     1344
Val Val Asp Val Ser His Glu Asp Pro Glu Val Lys Phe Asn Trp Tyr
        435                 440                 445 gtg gac ggc gtg gag gtg cat aat gcc aag aca aag ccg cgg gag gag     1392
Val Asp Gly Val Glu Val His Asn Ala Lys Thr Lys Pro Arg Glu Glu
450                 455                 460 cag tac aac agc acg tac cgg gtg gtc agc gtc ctc acc gtc tgt cac     1440
Gln Tyr Asn Ser Thr Tyr Arg Val Val Ser Val Leu Thr Val Cys His
465                 470                 475                 480 cag gac tgg ctg aat ggc aag gag tac aag tgc aag gtc tcc aac aaa     1488
Gln Asp Trp Leu Asn Gly Lys Glu Tyr Lys Cys Lys Val Ser Asn Lys
                485                 490                 495 gcc ctc cca gcc ccc atc gag aaa acc atc tcc aaa gcc aaa ggg cag     1536
Ala Leu Pro Ala Pro Ile Glu Lys Thr Ile Ser Lys Ala Lys Gly Gln
            500                 505                 510 ccc cga gaa cca cag gtg tac acc ctg ccc cca tcc cgg gat gag ctg     1584
Pro Arg Glu Pro Gln Val Tyr Thr Leu Pro Pro Ser Arg Asp Glu Leu
        515                 520                 525 acc aag aac cag gtc agc ctg acc tgc ctg gtc aaa ggc ttc tat ccc     1632
Thr Lys Asn Gln Val Ser Leu Thr Cys Leu Val Lys Gly Phe Tyr Pro
530                 535                 540 agc gac atc gcc gtg gag tgg gag agc aat ggg cag ccg gag aac aac     1680
Ser Asp Ile Ala Val Glu Trp Glu Ser Asn Gly Gln Pro Glu Asn Asn
545                 550                 555                 560 tac aag acc acg cct ccc gtg ctg gac tcc gac ggc tcc ttc ttc ctc     1728
Tyr Lys Thr Thr Pro Pro Val Leu Asp Ser Asp Gly Ser Phe Phe Leu
                565                 570                 575 tac agc aag ctc acc gtg gac aag agc agg tgg cag cag ggg aac gtc     1776
Tyr Ser Lys Leu Thr Val Asp Lys Ser Arg Trp Gln Gln Gly Asn Val
            580                 585                 590 ttc tca tgc tcc gtg atg cat gag gct ctg cac aac cac tac acg cag     1824
Phe Ser Cys Ser Val Met His Glu Ala Leu His Asn His Tyr Thr Gln
        595                 600                 605
```

```
aag agc ctc tcc ctg tct ccg ggt aaa         tga                    1854
Lys Ser Leu Ser Leu Ser Pro Gly Lys
    610             615
```

<210> SEQ ID NO 22
<211> LENGTH: 617
<212> TYPE: PRT
<213> ORGANISM: Homo sapiens

<400> SEQUENCE: 22

```
Met Ser Phe Pro Cys Lys Phe Val Ala Ser Phe Leu Leu Ile Phe Asn
 1               5                  10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Asn Val Ser Cys Pro Lys Asn Ile Thr
        195                 200                 205

Asn Ala Leu Glu Thr Trp Gly Ala Leu Gly Gln Asp Ile Asn Leu Asp
    210                 215                 220

Ile Pro Ser Phe Gln Met Ser Asp Asp Ile Asp Asp Ile Lys Trp Glu
225                 230                 235                 240

Lys Thr Ser Asp Lys Lys Lys Ile Ala Gln Phe Arg Lys Glu Lys Glu
                245                 250                 255

Thr Phe Lys Glu Lys Asp Thr Tyr Lys Leu Phe Lys Asn Gly Thr Leu
            260                 265                 270

Lys Ile Lys His Leu Lys Thr Asp Asp Gln Asp Ile Tyr Lys Val Ser
        275                 280                 285

Ile Tyr Asp Thr Lys Gly Lys Asn Val Leu Glu Lys Ile Phe Asp Leu
    290                 295                 300

Lys Ile Gln Glu Arg Val Ser Lys Pro Lys Ile Ser Trp Thr Cys Ile
305                 310                 315                 320

Asn Thr Thr Leu Thr Cys Glu Val Met Asn Gly Thr Asp Pro Glu Leu
                325                 330                 335

Asn Leu Tyr Gln Asp Gly Lys His Leu Lys Leu Ser Gln Arg Val Ile
            340                 345                 350
```

-continued

```
Thr His Lys Trp Thr Thr Ser Leu Ser Ala Lys Phe Lys Cys Thr Ala
        355                 360                 365
Gly Asn Lys Val Ser Lys Glu Ser Ser Val Glu Pro Val Ser Cys Pro
    370                 375                 380
Ala Glu Pro Lys Ser Cys Asp Lys Thr His Thr Cys Pro Pro Cys Pro
385                 390                 395                 400
Ala Pro Glu Leu Leu Gly Gly Pro Ser Val Phe Leu Phe Pro Pro Lys
                405                 410                 415
Pro Lys Asp Thr Leu Met Ile Ser Arg Thr Pro Glu Val Thr Cys Val
            420                 425                 430
Val Val Asp Val Ser His Glu Asp Pro Glu Val Lys Phe Asn Trp Tyr
        435                 440                 445
Val Asp Gly Val Glu Val His Asn Ala Lys Thr Lys Pro Arg Glu Glu
    450                 455                 460
Gln Tyr Asn Ser Thr Tyr Arg Val Val Ser Val Leu Thr Val Cys His
465                 470                 475                 480
Gln Asp Trp Leu Asn Gly Lys Glu Tyr Lys Cys Lys Val Ser Asn Lys
                485                 490                 495
Ala Leu Pro Ala Pro Ile Glu Lys Thr Ile Ser Lys Ala Lys Gly Gln
            500                 505                 510
Pro Arg Glu Pro Gln Val Tyr Thr Leu Pro Pro Ser Arg Asp Glu Leu
        515                 520                 525
Thr Lys Asn Gln Val Ser Leu Thr Cys Leu Val Lys Gly Phe Tyr Pro
    530                 535                 540
Ser Asp Ile Ala Val Glu Trp Glu Ser Asn Gly Gln Pro Glu Asn Asn
545                 550                 555                 560
Tyr Lys Thr Thr Pro Pro Val Leu Asp Ser Asp Gly Ser Phe Phe Leu
                565                 570                 575
Tyr Ser Lys Leu Thr Val Asp Lys Ser Arg Trp Gln Gln Gly Asn Val
            580                 585                 590
Phe Ser Cys Ser Val Met His Glu Ala Leu His Asn His Tyr Thr Gln
        595                 600                 605
Lys Ser Leu Ser Leu Ser Pro Gly Lys
    610                 615
```

<210> SEQ ID NO 23
<211> LENGTH: 1509
<212> TYPE: DNA
<213> ORGANISM: Homo sapiens
<220> FEATURE:
<221> NAME/KEY: CDS
<222> LOCATION: (1)..(1506)
<223> OTHER INFORMATION: mgCTLA4-CTLA4-IgG
<220> FEATURE:
<221> NAME/KEY: C_region
<222> LOCATION: (808)..(1509)
<223> OTHER INFORMATION: Hinge, CH2, CH3 region
<220> FEATURE:
<221> NAME/KEY: misc_signal
<222> LOCATION: (289)..(297)
<223> OTHER INFORMATION: N-linked glycosylation site
<220> FEATURE:
<221> NAME/KEY: misc_signal
<222> LOCATION: (385)..(393)
<223> OTHER INFORMATION: N-linked glycosylation site
<220> FEATURE:
<221> NAME/KEY: misc_signal
<222> LOCATION: (403)..(411)
<223> OTHER INFORMATION: N-linked glycosylation site

```
<220> FEATURE:
<221> NAME/KEY: misc_signal
<222> LOCATION: (424)..(432)
<223> OTHER INFORMATION: N-linked glycosylation site
<220> FEATURE:
<221> NAME/KEY: misc_signal
<222> LOCATION: (439)..(447)
<223> OTHER INFORMATION: N-linked glycosylation site
<220> FEATURE:
<221> NAME/KEY: misc_signal
<222> LOCATION: (664)..(672)
<223> OTHER INFORMATION: N-linked glycosylation site
<220> FEATURE:
<221> NAME/KEY: misc_signal
<222> LOCATION: (760)..(768)
<223> OTHER INFORMATION: N-linked glycosylation site
<220> FEATURE:
<221> NAME/KEY: primer_bind
<222> LOCATION: (1)..(15)
<223> OTHER INFORMATION: PCR primer SEQ ID : 43 binding site
<220> FEATURE:
<221> NAME/KEY: primer_bind
<222> LOCATION: (394)..(456)
<223> OTHER INFORMATION: PCR primer SEQ ID : 52(antisense) binding site
<220> FEATURE:
<221> NAME/KEY: primer_bind
<222> LOCATION: (397)..(460)
<223> OTHER INFORMATION: PCR primer SEQ ID : 51 binding site
<220> FEATURE:
<221> NAME/KEY: primer_bind
<222> LOCATION: (784)..(813)
<223> OTHER INFORMATION: PCR primer SEQ ID : 44(antisense) binding site
<220> FEATURE:
<221> NAME/KEY: primer_bind
<222> LOCATION: (805)..(826)
<223> OTHER INFORMATION: PCR primer SEQ ID : 42 binding site
<220> FEATURE:
<221> NAME/KEY: primer_bind
<222> LOCATION: (1486)..(1509)
<223> OTHER INFORMATION: PCR primer SEQ ID : 28(antisense) binding site
<220> FEATURE:
<221> NAME/KEY: sig_peptide
<222> LOCATION: (1)..(63)
<223> OTHER INFORMATION: signal peptide

<400> SEQUENCE: 23 atg agg acc tgg ccc tgc act ctc ctg ttt ttt ctt ctc ttc atc cct      48
Met Arg Thr Trp Pro Cys Thr Leu Leu Phe Phe Leu Leu Phe Ile Pro
 1               5                  10                  15 gtc ttc tgc aaa gca atg cac gtg gcc cag cct gct gtg gta ctg gcc      96
Val Phe Cys Lys Ala Met His Val Ala Gln Pro Ala Val Val Leu Ala
             20                  25                  30 agc agc cga ggc atc gcc agc ttt gtg tgt gag tat gca tct cca ggc     144
Ser Ser Arg Gly Ile Ala Ser Phe Val Cys Glu Tyr Ala Ser Pro Gly
         35                  40                  45 aaa gcc act gag gtc cgg gtg aca gtg ctt cgg cag gct gac agc cag     192
Lys Ala Thr Glu Val Arg Val Thr Val Leu Arg Gln Ala Asp Ser Gln
     50                  55                  60 gtg act gaa gtc tgt gcg gca acc tac atg atg ggg aat gag ttg acc     240
Val Thr Glu Val Cys Ala Ala Thr Tyr Met Met Gly Asn Glu Leu Thr
 65                  70                  75                  80 ttc cta gat gat tcc atc tgc acg ggc acc tcc agt gga aat caa gtg     288
Phe Leu Asp Asp Ser Ile Cys Thr Gly Thr Ser Ser Gly Asn Gln Val
                 85                  90                  95 aac ctc act atc caa gga ctg agg gcc atg gac acg gga ctc tac atc     336
Asn Leu Thr Ile Gln Gly Leu Arg Ala Met Asp Thr Gly Leu Tyr Ile
            100                 105                 110 tgc aag gtg gag ctc atg tac cca ccg cca tac tac ctg ggc ata ggc     384
Cys Lys Val Glu Leu Met Tyr Pro Pro Pro Tyr Tyr Leu Gly Ile Gly
        115                 120                 125
```

```
aac gga acc cag att tat gta aat gat aca gaa ccg tgc aat gat tcg         432
Asn Gly Thr Gln Ile Tyr Val Asn Asp Thr Glu Pro Cys Asn Asp Ser
        130             135                 140 gat aac aat cac acg gcc cag cct gct gta ctg gcc agc agc cga             480
Asp Asn Asn His Thr Ala Gln Pro Ala Val Leu Ala Ser Ser Arg
145             150                 155                 160 ggc atc gcc agc ttt gtg tgt gag tat gca tct cca ggc aaa gcc act         528
Gly Ile Ala Ser Phe Val Cys Glu Tyr Ala Ser Pro Gly Lys Ala Thr
                165                 170                 175 gag gtc cgg gtg aca gtg ctt cgg cag gct gac agc cag gtg act gaa         576
Glu Val Arg Val Thr Val Leu Arg Gln Ala Asp Ser Gln Val Thr Glu
            180                 185                 190 gtc tgt gcg gca acc tac atg atg ggg aat gag ttg acc ttc cta gat         624
Val Cys Ala Ala Thr Tyr Met Met Gly Asn Glu Leu Thr Phe Leu Asp
        195                 200                 205 gat tcc atc tgc acg ggc acc tcc agt gga aat caa gtg aac ctc act         672
Asp Ser Ile Cys Thr Gly Thr Ser Ser Gly Asn Gln Val Asn Leu Thr
    210                 215                 220 atc caa gga ctg agg gcc atg gac acg gga ctc tac atc tgc aag gtg         720
Ile Gln Gly Leu Arg Ala Met Asp Thr Gly Leu Tyr Ile Cys Lys Val
225                 230                 235                 240 gag ctc atg tac cca ccg cca tac tac ctg ggc ata ggc aac gga acc         768
Glu Leu Met Tyr Pro Pro Pro Tyr Tyr Leu Gly Ile Gly Asn Gly Thr
                245                 250                 255 cag att tat gta att gat cca gaa ccg tgc cca gat tct gca gag ccc         816
Gln Ile Tyr Val Ile Asp Pro Glu Pro Cys Pro Asp Ser Ala Glu Pro
            260                 265                 270 aaa tct tgt gac aaa act cac aca tgc cca ccg tgc cca gca cct gaa         864
Lys Ser Cys Asp Lys Thr His Thr Cys Pro Pro Cys Pro Ala Pro Glu
        275                 280                 285 ctc ctg ggg gga ccg tca gtc ttc ctc ttc ccc cca aaa ccc aag gac         912
Leu Leu Gly Gly Pro Ser Val Phe Leu Phe Pro Pro Lys Pro Lys Asp
    290                 295                 300 acc ctc atg atc tcc cgg acc cct gag gtc aca tgc gtg gtg gtg gac         960
Thr Leu Met Ile Ser Arg Thr Pro Glu Val Thr Cys Val Val Val Asp
305                 310                 315                 320 gtg agc cac gaa gac cct gag gtc aag ttc aac tgg tac gtg gac ggc        1008
Val Ser His Glu Asp Pro Glu Val Lys Phe Asn Trp Tyr Val Asp Gly
                325                 330                 335 gtg gag gtg cat aat gcc aag aca aag ccg cgg gag gag cag tac aac        1056
Val Glu Val His Asn Ala Lys Thr Lys Pro Arg Glu Glu Gln Tyr Asn
            340                 345                 350 agc acg tac cgg gtg gtc agc gtc ctc acc gtc tgt cac cag gac tgg        1104
Ser Thr Tyr Arg Val Val Ser Val Leu Thr Val Cys His Gln Asp Trp
        355                 360                 365 ctg aat ggc aag gag tac aag tgc aag gtc tcc aac aaa gcc ctc cca        1152
Leu Asn Gly Lys Glu Tyr Lys Cys Lys Val Ser Asn Lys Ala Leu Pro
    370                 375                 380 gcc ccc atc gag aaa acc atc tcc aaa gcc aaa ggg cag ccc cga gaa        1200
Ala Pro Ile Glu Lys Thr Ile Ser Lys Ala Lys Gly Gln Pro Arg Glu
385                 390                 395                 400 cca cag gtg tac acc ctg ccc cca tcc cgg gat gag ctg acc aag aac        1248
Pro Gln Val Tyr Thr Leu Pro Pro Ser Arg Asp Glu Leu Thr Lys Asn
                405                 410                 415 cag gtc agc ctg acc tgc ctg gtc aaa ggc ttc tat ccc agc gac atc        1296
Gln Val Ser Leu Thr Cys Leu Val Lys Gly Phe Tyr Pro Ser Asp Ile
            420                 425                 430 gcc gtg gag tgg gag agc aat ggg cag ccg gag aac aac tac aag acc        1344
Ala Val Glu Trp Glu Ser Asn Gly Gln Pro Glu Asn Asn Tyr Lys Thr
        435                 440                 445
```

```
acg cct ccc gtg ctg gac tcc gac ggc tcc ttc ttc ctc tac agc aag    1392
Thr Pro Pro Val Leu Asp Ser Asp Gly Ser Phe Phe Leu Tyr Ser Lys
450                 455                 460 ctc acc gtg gac aag agc agg tgg cag cag ggg aac gtc ttc tca tgc    1440
Leu Thr Val Asp Lys Ser Arg Trp Gln Gln Gly Asn Val Phe Ser Cys
465                 470                 475                 480 tcc gtg atg cat gag gct ctg cac aac cac tac acg cag aag agc ctc    1488
Ser Val Met His Glu Ala Leu His Asn His Tyr Thr Gln Lys Ser Leu
            485                 490                 495 tcc ctg tct ccg ggt aaa     tga                                    1509
Ser Leu Ser Pro Gly Lys
            500
```

<210> SEQ ID NO 24
<211> LENGTH: 502
<212> TYPE: PRT
<213> ORGANISM: Homo sapiens

<400> SEQUENCE: 24

```
Met Arg Thr Trp Pro Cys Thr Leu Leu Phe Leu Leu Phe Ile Pro
 1               5                  10                  15

Val Phe Cys Lys Ala Met His Val Ala Gln Pro Ala Val Leu Ala
                20                  25                  30

Ser Ser Arg Gly Ile Ala Ser Phe Val Cys Glu Tyr Ala Ser Pro Gly
            35                  40                  45

Lys Ala Thr Glu Val Arg Val Thr Val Leu Arg Gln Ala Asp Ser Gln
50                  55                  60

Val Thr Glu Val Cys Ala Ala Thr Tyr Met Met Gly Asn Glu Leu Thr
65                  70                  75                  80

Phe Leu Asp Asp Ser Ile Cys Thr Gly Thr Ser Ser Gly Asn Gln Val
                85                  90                  95

Asn Leu Thr Ile Gln Gly Leu Arg Ala Met Asp Thr Gly Leu Tyr Ile
            100                 105                 110

Cys Lys Val Glu Leu Met Tyr Pro Pro Pro Tyr Tyr Leu Gly Ile Gly
        115                 120                 125

Asn Gly Thr Gln Ile Tyr Val Asn Asp Thr Glu Pro Cys Asn Asp Ser
130                 135                 140

Asp Asn Asn His Thr Ala Gln Pro Ala Val Leu Ala Ser Ser Arg
145                 150                 155                 160

Gly Ile Ala Ser Phe Val Cys Glu Tyr Ala Ser Pro Gly Lys Ala Thr
                165                 170                 175

Glu Val Arg Val Thr Val Leu Arg Gln Ala Asp Ser Gln Val Thr Glu
            180                 185                 190

Val Cys Ala Ala Thr Tyr Met Met Gly Asn Glu Leu Thr Phe Leu Asp
        195                 200                 205

Asp Ser Ile Cys Thr Gly Thr Ser Ser Gly Asn Gln Val Asn Leu Thr
210                 215                 220

Ile Gln Gly Leu Arg Ala Met Asp Thr Gly Leu Tyr Ile Cys Lys Val
225                 230                 235                 240

Glu Leu Met Tyr Pro Pro Pro Tyr Tyr Leu Gly Ile Gly Asn Gly Thr
                245                 250                 255

Gln Ile Tyr Val Ile Asp Pro Glu Pro Cys Pro Asp Ser Ala Glu Pro
            260                 265                 270

Lys Ser Cys Asp Lys Thr His Thr Cys Pro Pro Cys Pro Ala Pro Glu
        275                 280                 285
```

```
Leu Leu Gly Gly Pro Ser Val Phe Leu Phe Pro Pro Lys Pro Lys Asp
    290                 295                 300
Thr Leu Met Ile Ser Arg Thr Pro Glu Val Thr Cys Val Val Val Asp
305                 310                 315                 320
Val Ser His Glu Asp Pro Glu Val Lys Phe Asn Trp Tyr Val Asp Gly
                325                 330                 335
Val Glu Val His Asn Ala Lys Thr Lys Pro Arg Glu Glu Gln Tyr Asn
            340                 345                 350
Ser Thr Tyr Arg Val Val Ser Val Leu Thr Val Cys His Gln Asp Trp
        355                 360                 365
Leu Asn Gly Lys Glu Tyr Lys Cys Lys Val Ser Asn Lys Ala Leu Pro
    370                 375                 380
Ala Pro Ile Glu Lys Thr Ile Ser Lys Ala Lys Gly Gln Pro Arg Glu
385                 390                 395                 400
Pro Gln Val Tyr Thr Leu Pro Pro Ser Arg Asp Glu Leu Thr Lys Asn
                405                 410                 415
Gln Val Ser Leu Thr Cys Leu Val Lys Gly Phe Tyr Pro Ser Asp Ile
            420                 425                 430
Ala Val Glu Trp Glu Ser Asn Gly Gln Pro Glu Asn Asn Tyr Lys Thr
        435                 440                 445
Thr Pro Pro Val Leu Asp Ser Asp Gly Ser Phe Phe Leu Tyr Ser Lys
    450                 455                 460
Leu Thr Val Asp Lys Ser Arg Trp Gln Gln Gly Asn Val Phe Ser Cys
465                 470                 475                 480
Ser Val Met His Glu Ala Leu His Asn His Tyr Thr Gln Lys Ser Leu
                485                 490                 495
Ser Leu Ser Pro Gly Lys
            500

<210> SEQ ID NO 25
<211> LENGTH: 33
<212> TYPE: DNA
<213> ORGANISM: Artificial Sequence
<220> FEATURE:
<223> OTHER INFORMATION: PCR primer, oligonucleotide TNFR1-EDF-EcoRI

<400> SEQUENCE: 25
ccggaattcc ggtctggcat gggcctctcc acc                              33

<210> SEQ ID NO 26
<211> LENGTH: 37
<212> TYPE: DNA
<213> ORGANISM: Artificial Sequence
<220> FEATURE:
<223> OTHER INFORMATION: PCR primer, oligonucleotide TNFR1-EDR-IgGh

<400> SEQUENCE: 26
cacaagattt gggctctgct gtggtgcctg agtcctc                          37

<210> SEQ ID NO 27
<211> LENGTH: 37
<212> TYPE: DNA
<213> ORGANISM: Artificial Sequence
<220> FEATURE:
<223> OTHER INFORMATION: PCR primer, oligonucleotide IgG1-T1F

<400> SEQUENCE: 27
gaggactcag gcaccacagc agagcccaaa tcttgtg                          37
```

<210> SEQ ID NO 28
<211> LENGTH: 34
<212> TYPE: DNA
<213> ORGANISM: Artificial Sequence
<220> FEATURE:
<223> OTHER INFORMATION: PCR primer, oligonucleotide IgG1-R-XbaI

<400> SEQUENCE: 28
gctctagagc tcatttaccc ggagacaggg agag                          34

<210> SEQ ID NO 29
<211> LENGTH: 33
<212> TYPE: DNA
<213> ORGANISM: Artificial Sequence
<220> FEATURE:
<223> OTHER INFORMATION: PCR primer, oligonucleotide TNFR2-EDF-EcoRI

<400> SEQUENCE: 29
ccggaattcc gggcacccat ggcgcccgtc gcc                           33

<210> SEQ ID NO 30
<211> LENGTH: 37
<212> TYPE: DNA
<213> ORGANISM: Artificial Sequence
<220> FEATURE:
<223> OTHER INFORMATION: PCR primer, oligonucleotide TNFR2-EDR-IgGh

<400> SEQUENCE: 30
cacaagattt gggctctgcg tcgccagtgc tcccttc                       37

<210> SEQ ID NO 31
<211> LENGTH: 37
<212> TYPE: DNA
<213> ORGANISM: Artificial Sequence
<220> FEATURE:
<223> OTHER INFORMATION: PCR primer, oligonucleotide IgG-T2F

<400> SEQUENCE: 31
gaagggagca ctggcgacgc agagcccaaa tcttgtg                       37

<210> SEQ ID NO 32
<211> LENGTH: 37
<212> TYPE: DNA
<213> ORGANISM: Artificial Sequence
<220> FEATURE:
<223> OTHER INFORMATION: PCR primer, oligonucleotide TNFR1-CF-BamHI

<400> SEQUENCE: 32
cgcggatccg ggaacatttc actggtccct cacctag                       37

<210> SEQ ID NO 33
<211> LENGTH: 39
<212> TYPE: DNA
<213> ORGANISM: Artificial Sequence
<220> FEATURE:
<223> OTHER INFORMATION: PCR primer, oligonucleotide TNFR1-NR-BamHI

<400> SEQUENCE: 33
cgcggatccg tcctcagtgc ccttaacatt ctcaatctg                     39

<210> SEQ ID NO 34
<211> LENGTH: 36
<212> TYPE: DNA
<213> ORGANISM: Artificial Sequence -continued

```
<220> FEATURE:
<223> OTHER INFORMATION: PCR primer, oligonucleotide TNFR2-CF-BamHI

<400> SEQUENCE: 34
cgcggatcca acgcaactac accctacgcc ccggag                              36

<210> SEQ ID NO 35
<211> LENGTH: 31
<212> TYPE: DNA
<213> ORGANISM: Artificial Sequence
<220> FEATURE:
<223> OTHER INFORMATION: PCR primer, oligonucleotide TNFR2-NR-BamHI

<400> SEQUENCE: 35
cgcggatccg ctcccttcag ctgggggct g                                    31

<210> SEQ ID NO 36
<211> LENGTH: 63
<212> TYPE: DNA
<213> ORGANISM: Artificial Sequence
<220> FEATURE:
<223> OTHER INFORMATION: PCR primer, oligonucleotide mgTNFR1-TNFR1-IgG-F

<400> SEQUENCE: 36
aaaagcaacg agaccaacaa gacctgccta cacaacgggt ccagggagaa gaacgatagt    60
gtg                                                                 63

<210> SEQ ID NO 37
<211> LENGTH: 62
<212> TYPE: DNA
<213> ORGANISM: Artificial Sequence
<220> FEATURE:
<223> OTHER INFORMATION: PCR primer, oligonucleotide mgTNFR1-TNFR1-IgG-R

<400> SEQUENCE: 37
ctccctggac ccgttgtgta ggcaggtctt gttggtctcg ttgcttttct tacagttact    60
ac                                                                  62

<210> SEQ ID NO 38
<211> LENGTH: 45
<212> TYPE: DNA
<213> ORGANISM: Artificial Sequence
<220> FEATURE:
<223> OTHER INFORMATION: PCR primer, oligonucleotide mgTNFR2-TNFR2-IgG-F

<400> SEQUENCE: 38
atggatgcaa actgcacgtc cccggagccc aacagcacat gccgg                    45

<210> SEQ ID NO 39
<211> LENGTH: 42
<212> TYPE: DNA
<213> ORGANISM: Artificial Sequence
<220> FEATURE:
<223> OTHER INFORMATION: PCR primer, oligonucleotide mgTNFR2-TNFR2-IgG-R

<400> SEQUENCE: 39
gcatgtgctg ttgggctccg gggacgtgca gtttgcatcc at                       42

<210> SEQ ID NO 40
<211> LENGTH: 36
<212> TYPE: DNA
<213> ORGANISM: Artificial Sequence
```

```
<220> FEATURE:
<223> OTHER INFORMATION: PCR primer, oligonucleotide CD2F-EcoRI

<400> SEQUENCE: 40
ccggaattca tgagctttcc atgtaaattt gtagcc                              36

<210> SEQ ID NO 41
<211> LENGTH: 30
<212> TYPE: DNA
<213> ORGANISM: Artificial Sequence
<220> FEATURE:
<223> OTHER INFORMATION: PCR primer, oligonucleotide CD2R-PstI

<400> SEQUENCE: 41
ctctgcagga cagctgacag gctcgacact                                     30

<210> SEQ ID NO 42
<211> LENGTH: 25
<212> TYPE: DNA
<213> ORGANISM: Artificial Sequence
<220> FEATURE:
<223> OTHER INFORMATION: PCR primer, oligonucleotide IgG-F-PstI

<400> SEQUENCE: 42
atctgcagag cccaaatctt gtgac                                          25

<210> SEQ ID NO 43
<211> LENGTH: 24
<212> TYPE: DNA
<213> ORGANISM: Artificial Sequence
<220> FEATURE:
<223> OTHER INFORMATION: PCR primer, oligonucleotide CTLA4F-EcoRI

<400> SEQUENCE: 43
ccggaattca tgaggacctg gccc                                           24

<210> SEQ ID NO 44
<211> LENGTH: 30
<212> TYPE: DNA
<213> ORGANISM: Artificial Sequence
<220> FEATURE:
<223> OTHER INFORMATION: PCR primer, oligonucleotide CTLA4R-PstI

<400> SEQUENCE: 44
ctctgcagaa tctgggcacg gttcaggatc                                     30

<210> SEQ ID NO 45
<211> LENGTH: 19
<212> TYPE: DNA
<213> ORGANISM: Artificial Sequence
<220> FEATURE:
<223> OTHER INFORMATION: PCR primer, oligonucleotide CD2-NT-F

<400> SEQUENCE: 45
taaagagatt acgaatgcc                                                 19

<210> SEQ ID NO 46
<211> LENGTH: 18
<212> TYPE: DNA
<213> ORGANISM: Artificial Sequence
<220> FEATURE:
<223> OTHER INFORMATION: PCR primer, oligonucleotide CD2-CT-R

<400> SEQUENCE: 46
tgcaggacag ctgacagg                                                  18
```

<210> SEQ ID NO 47
<211> LENGTH: 23
<212> TYPE: DNA
<213> ORGANISM: Artificial Sequence
<220> FEATURE:
<223> OTHER INFORMATION: PCR primer, oligonucleotide CTLA4-NT-F

<400> SEQUENCE: 47
ggataatcat gcacgtggcc cag                                           23

<210> SEQ ID NO 48
<211> LENGTH: 18
<212> TYPE: DNA
<213> ORGANISM: Artificial Sequence
<220> FEATURE:
<223> OTHER INFORMATION: PCR primer, oligonucleotide CTLA4-CT-R

<400> SEQUENCE: 48
tgcagaatct gggcacgg                                                 18

<210> SEQ ID NO 49
<211> LENGTH: 43
<212> TYPE: DNA
<213> ORGANISM: Artificial Sequence
<220> FEATURE:
<223> OTHER INFORMATION: PCR primer, oligonucleotide mgCD2-CD2-IgG-F

<400> SEQUENCE: 49
cagtgtcgag aatgtcagct gtcctaaaaa tattacgaat gcc                     43

<210> SEQ ID NO 50
<211> LENGTH: 43
<212> TYPE: DNA
<213> ORGANISM: Artificial Sequence
<220> FEATURE:
<223> OTHER INFORMATION: PCR primer, oligonucleotide mgCD2-CD2-IgG-R

<400> SEQUENCE: 50
ggcattcgta atattttag gacagctgac attctcgaca ctg                      43

<210> SEQ ID NO 51
<211> LENGTH: 64
<212> TYPE: DNA
<213> ORGANISM: Artificial Sequence
<220> FEATURE:
<223> OTHER INFORMATION: PCR primer, oligonucleotide mgCTLA4-CTLA4-IgG-F

<400> SEQUENCE: 51
atttatgtaa acgatacaga accgtgcaat gattcggata caaccacac agcccagcct    60 gctg                                                                64

<210> SEQ ID NO 52
<211> LENGTH: 63
<212> TYPE: DNA
<213> ORGANISM: Artificial Sequence
<220> FEATURE:
<223> OTHER INFORMATION: PCR primer, oligonucleotide mgCTLA4-CTLA4-IgG-R

<400> SEQUENCE: 52
aggctgggct gtgtggttgt tatccgaatc attgcacggt tctgtatcgt ttacataaat   60
ctg                                                                 63